US012714688B2

(12) United States Patent
Chesler et al.

(10) Patent No.: US 12,714,688 B2
(45) Date of Patent: Aug. 25, 2026

(54) MARGARIC ACID DECREASES PIEZ02-MEDIATED PAIN

(71) Applicants: The United States of America, as represented by The Secretary, Dept. of Health And Human Services, Bethesda, MD (US); University of Tennessee Research Foundation, Knoxville, TN (US)

(72) Inventors: Alexander Theodore Chesler, Bethesda, MD (US); Valeria Vasquez, Germantown, TN (US); Julio Francisco Cordero-Morales, Germantown, TN (US); Luis Octavio Romero, Memphis, TN (US); Kaining Zhi, Memphis, TN (US); Harry Kochat, Piperton, TN (US)

(73) Assignees: The United States of Americas, as represented by The Secretary, Dept. of Health and Human Services, Bethesda, MD (US); University of Tennessee Research Foundation, Knoxville, TN (US)

( * ) Notice: Subject to any disclaimer, the term of this patent is extended or adjusted under 35 U.S.C. 154(b) by 931 days.

(21) Appl. No.: 17/799,500

(22) PCT Filed: Feb. 12, 2021

(86) PCT No.: PCT/US2021/017780

§ 371 (c)(1),
(2) Date: Aug. 12, 2022

(87) PCT Pub. No.: WO2021/163425

PCT Pub. Date: Aug. 19, 2021

(65) Prior Publication Data

US 2023/0092870 A1 Mar. 23, 2023

Related U.S. Application Data

(60) Provisional application No. 62/976,014, filed on Feb. 13, 2020.

(51) Int. Cl.

| | |
|---|---|
| ***A61K 31/20*** | (2006.01) |
| ***A61K 31/557*** | (2006.01) |
| ***A61K 47/44*** | (2017.01) |
| ***A61P 29/00*** | (2006.01) |

(52) U.S. Cl.
CPC ............ *A61K 31/20* (2013.01); *A61K 31/557* (2013.01); *A61K 47/44* (2013.01); *A61P 29/00* (2018.01)

(58) Field of Classification Search
CPC ........ A61K 31/20; A61K 31/557; A61P 29/00
See application file for complete search history.

(56) References Cited

U.S. PATENT DOCUMENTS 3,646,215 A 2/1972 Phillips

FOREIGN PATENT DOCUMENTS

| | | | |
|---|---|---|---|
| CN | 101933932 | A | 1/2011 |
| EP | 2801369 | A1 | 11/2014 |
| JP | 2007-246469 | A | 9/2007 |
| JP | 2013-538058 | A | 10/2013 |
| JP | 2016-088885 | A | 5/2016 |
| JP | 2021-525249 | A | 9/2021 |
| WO | WO2019146735 | A1 | 8/2019 |
| WO | WO2019/226572 | | 11/2019 |

OTHER PUBLICATIONS

Romero L.O., et al., "Dietary Fatty Acids Fine-tune Piezo1 Mechanical Response", Nature Communications, vol. 10, No. 01, Mar. 13, 2019, p. 1-14.
First Office action corresponding to Chinese patent application. 202180015900.1, dated Sep. 27, 2024, 11 Pages.
Second Office action corresponding to Chinese patent application. 202180015900.1, dated May 26, 2025, 9 Pages.
Notice of Reasons for Refusal corresponding to Japanese patent application. 2022-548411, dated Jan. 15, 2025, 10 Pages.
Nakamoto, K., "Hypothalamic GPR40 signaling activated by free long chain fatty acids suppresses CFA-induced inflammatory chronic pain," PLoS One, vol. 8, Issue 12, Dec. 12, 2013, pp. 1-11.
International Preliminary Report on Patentability Corresponding to International Application No. PCT/US2021/017780, dated Aug. 11, 2022, 7 Pages.
Pietra, A.D., "The Emerging Role of Mechanosensitive Piezo Channels in Migraine Pain," Int. J. Mol. Sci. 2020, 21, 696, pp. 1-10.
Jenkins, B.J., "Odd Chain Fatty Acids; New Insights of the Relationship Between the Gut Microbiota, Dietary Intake, Biosynthesis and Glucose Intolerance," Scientific Reports, pp. 1-8, 2017.
Venn-Watson, S.K., "Increased Dietary Intake of Saturated Fatty Acid Heptadecanoic Acid (C17:0) Associated with Decreasing Ferritin and Alleviated Metabolic Syndrome in Dolphins," PLoS ONE 10(7), pp. 1-17, 2015.
Romero L.O., et al., "A dietary fatty acid counteracts neuronal mechanical sensitization," Nature communications, 11, 2997, pp. 1-12, 2020.
Yamaguchi, T., "PIEZO2 deficiency is a recognizable arthrogryposis syndrome: A new case and literature review," American Journal of Medical genetics, Wiley Periodicals, Inc., pp. 1-11, 2019.
EP Office action (Communication pursuant) corresponding to European patent application. 2171 0729.1-1112, dated Sep. 22, 2022, 3 Pages.
EP Office action (Communication pursuant) corresponding to European patent application. 2171 0729.1-1109, dated Dec. 20, 2024, 6 Pages.

(Continued)

*Primary Examiner* — Kevin E Weddington
(74) *Attorney, Agent, or Firm* — Jenkins, Taylor & Hunt, P.A.

(57) ABSTRACT

Described herein is a method of treating pain by administering to a subject in need of treatment for pain a pharmaceutical composition including a therapeutically effective amount of margaric acid. Also described are pharmaceutical compositions such as topical and transdermal compositions including margaric acid and a pharmaceutically acceptable excipient. Further described is a composition for the treatment of pain including margaric acid, eicosapentaenoic acid, and a pharmaceutically acceptable excipient.

24 Claims, 36 Drawing Sheets

(56) References Cited

OTHER PUBLICATIONS

International Search Report of the International Searching Authority corresponding to International Application No. PCT/US 2021/017780 dated May 21, 2021.
Written Opinion of the International Searching Authority corresponding to International Application No. PCT/US 2021/017780 dated May 21, 2021.
Romero et al., "Margaric Acid Decreases Sensory Neurons Mechanical Excitability by Inhibiting PIEZ02 Channels", Biophysical Journal, vol. 118, No. 3, Suppl. 1, pp. 397A-398A (Feb. 7, 2020).
Szczot et al., "PIEZ02 mediates injury-induced tactile pain in mice and humans", Science Translational Medicine, vol. 10, No. 462, pp. 5-6 abstract (Oct. 10, 2018).
Morin et al., "Eicosapentaenoic acid and docosapentaenoic acid monoglycerides are more potent than docosahexaenoic acid monoglyceride to resolve inflammation in a rheumatoid arthritis model", Arthritis Research & Therapy, vol. 17, No. 1, p. 142 (Dec. 2015).
"1-Heptadecanol Material Safety Data Sheet—Sigma-Aldrich 241695," pp. 2, Oct. 24, 2025.

N2A Piezo-/- + MOUSE PIEZO2
[MARGARIC ACID, MA] (μM)
CONTROL
1
50
200
300
400
600
10μm
0.5 nA
100 ms

NORMALIZED CURRENT DENSITY
1.0
0.8
0.6
0.4
0.2
0
1
25
50
100
300
600
[MA] (μM)

THRESHOLD (μm)
21
14
7
0
ns
***
11
5
6
0
1
25
50
100
200
300
400
600
[MA] (μM)

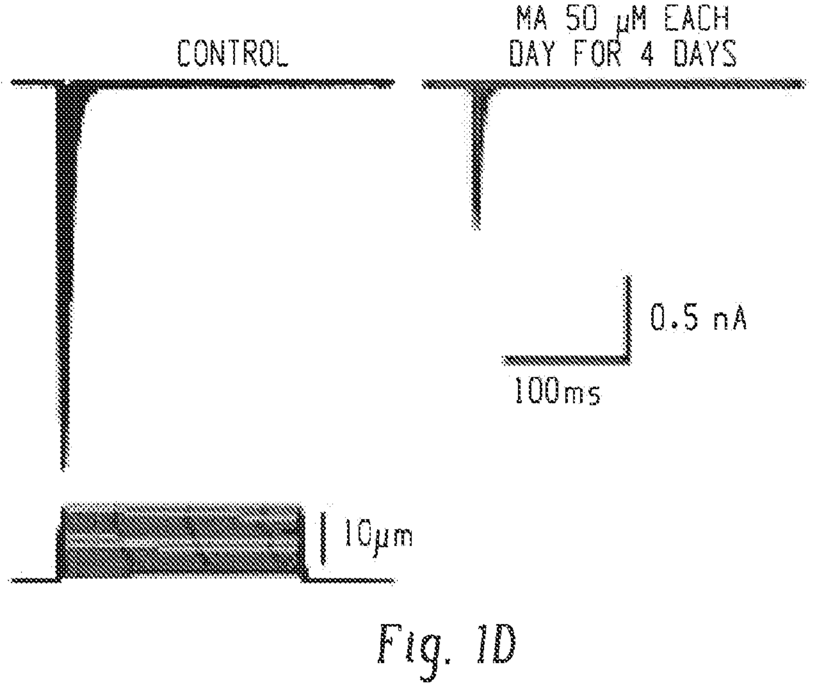
Fig. 1D
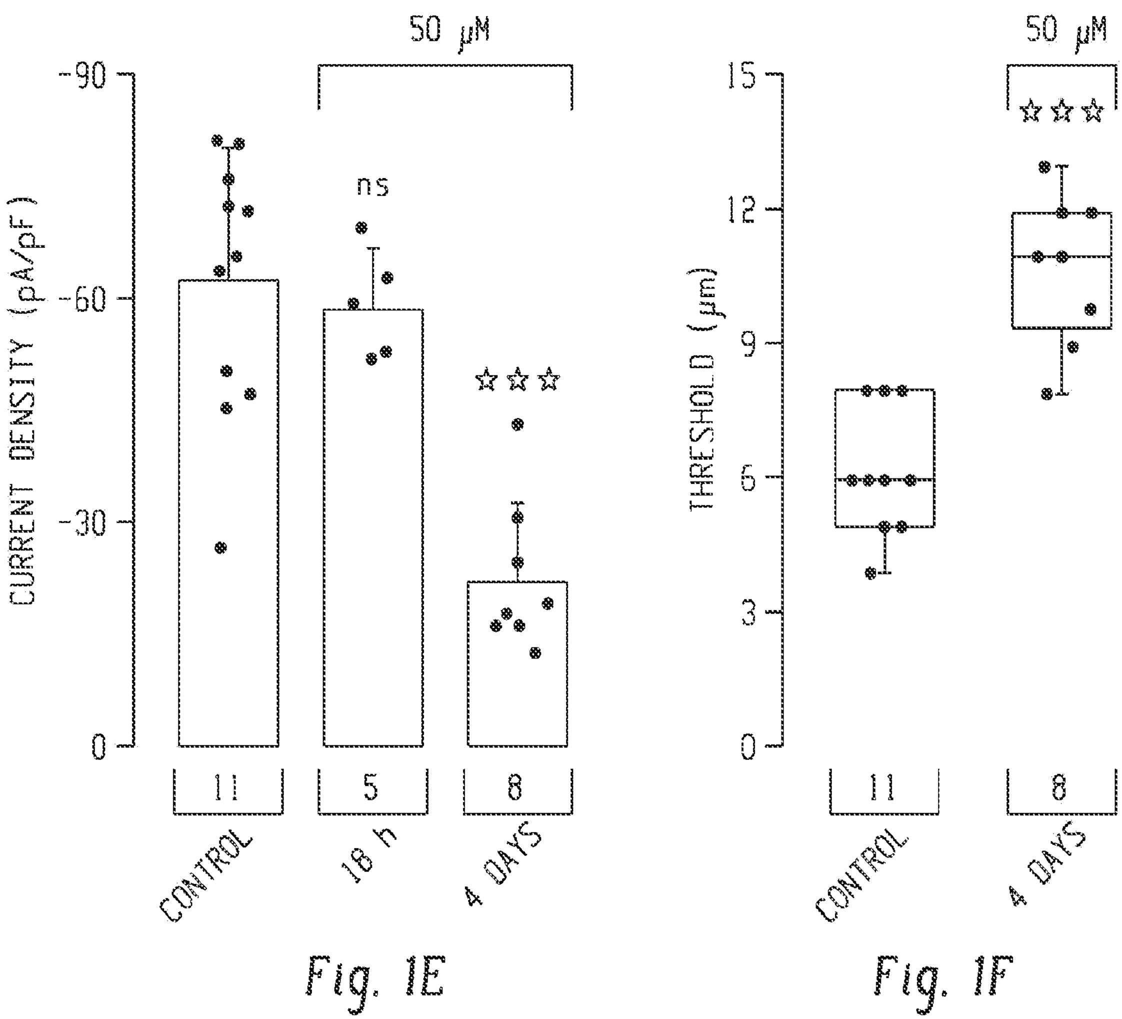
Fig. 1E
Fig. 1F

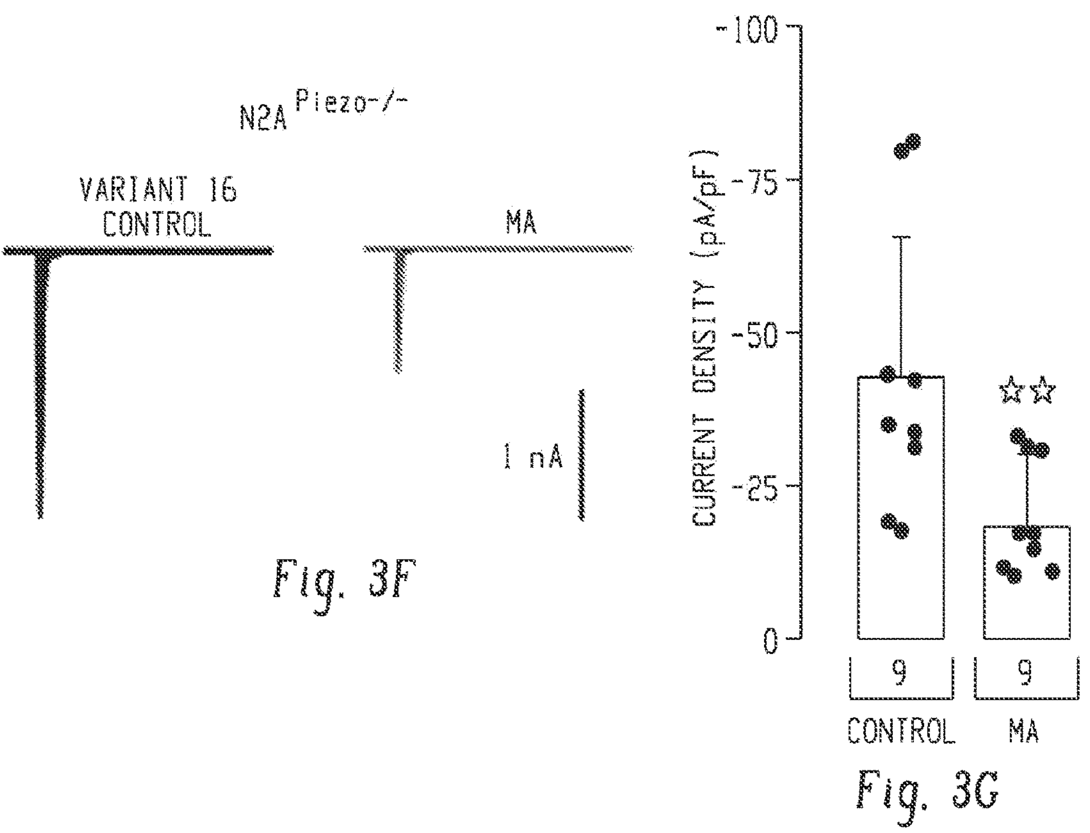
Fig. 3F
Fig. 3G
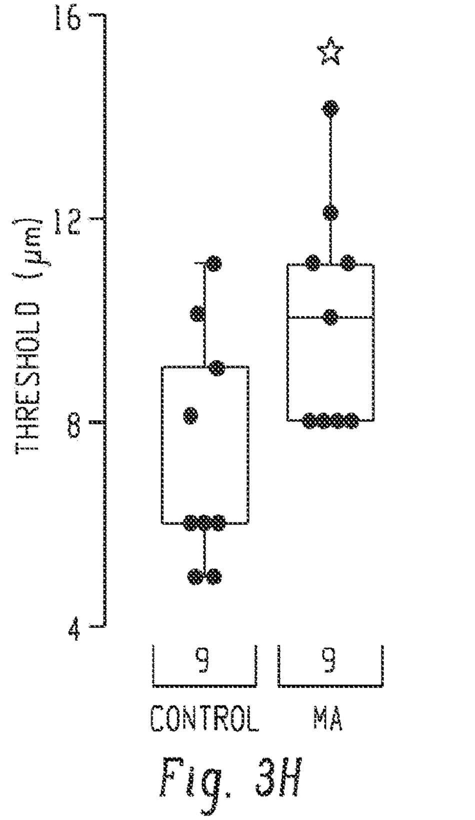
Fig. 3H
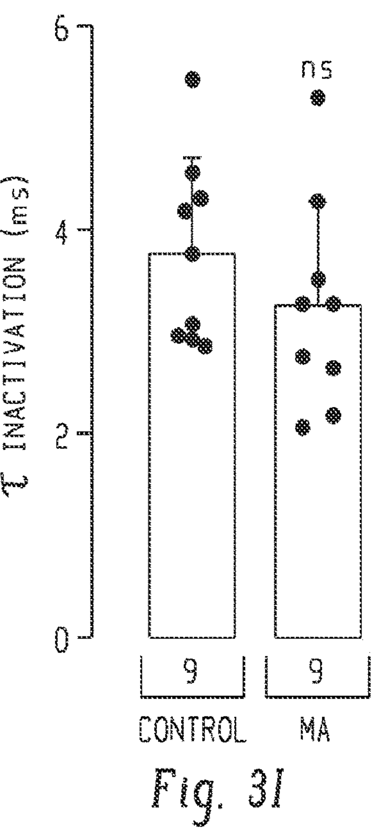
Fig. 3I ns
☆☆
☆☆☆
% OF INHIBITION BY MA 100μM
100
80
60
40
20
0
13
6
9
Piezo1
Piezo2
Piezo2-Piezo1

[MA] (100 μM)
Piezo1
Piezo2
Piezo2-Piezo1
☆☆
ns
ns
NORMALIZED CURRENT DENSITY
1.2
0.9
0.6
0.3
0
13
6
6
5
9
5
CONTROL
LatA
CONTROL
LatA
CONTROL
LatA

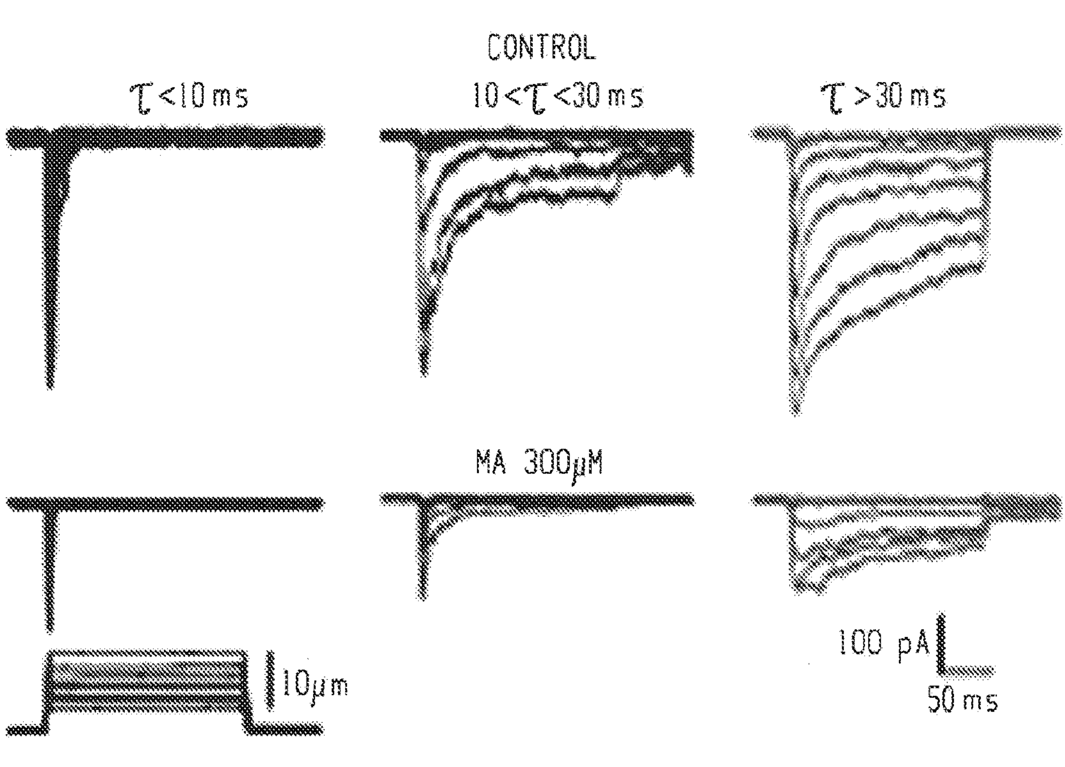
Fig. 7D
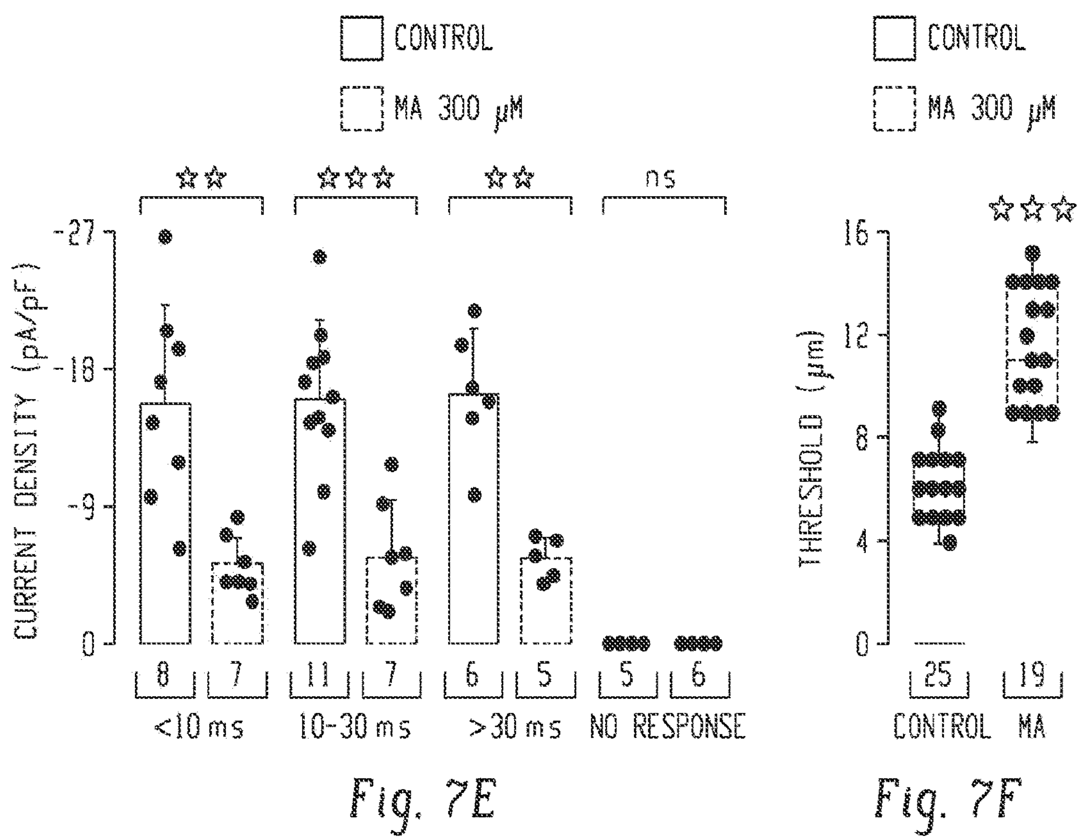
Fig. 7E
Fig. 7F

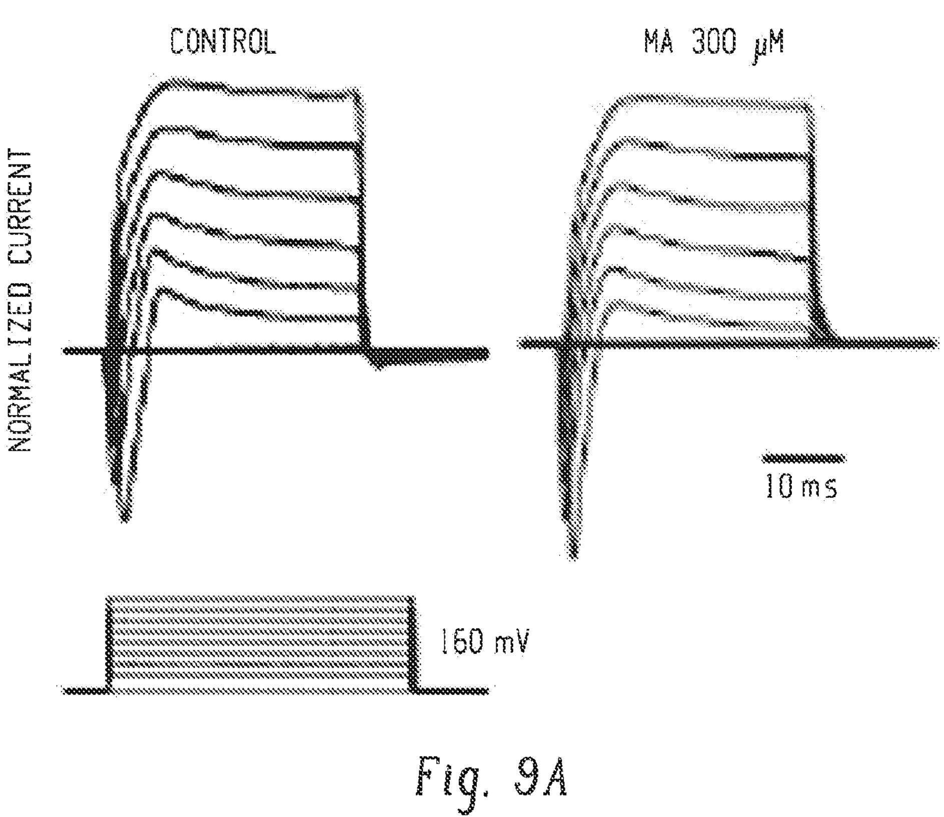
Fig. 9A
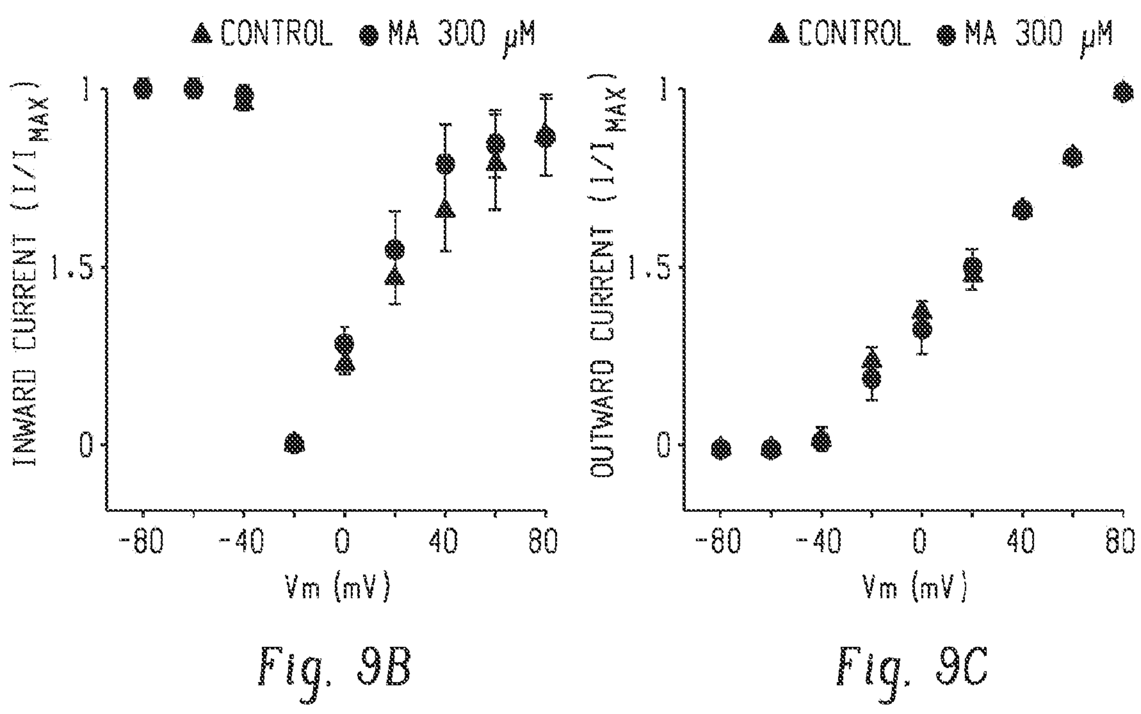
Fig. 9B
Fig. 9C

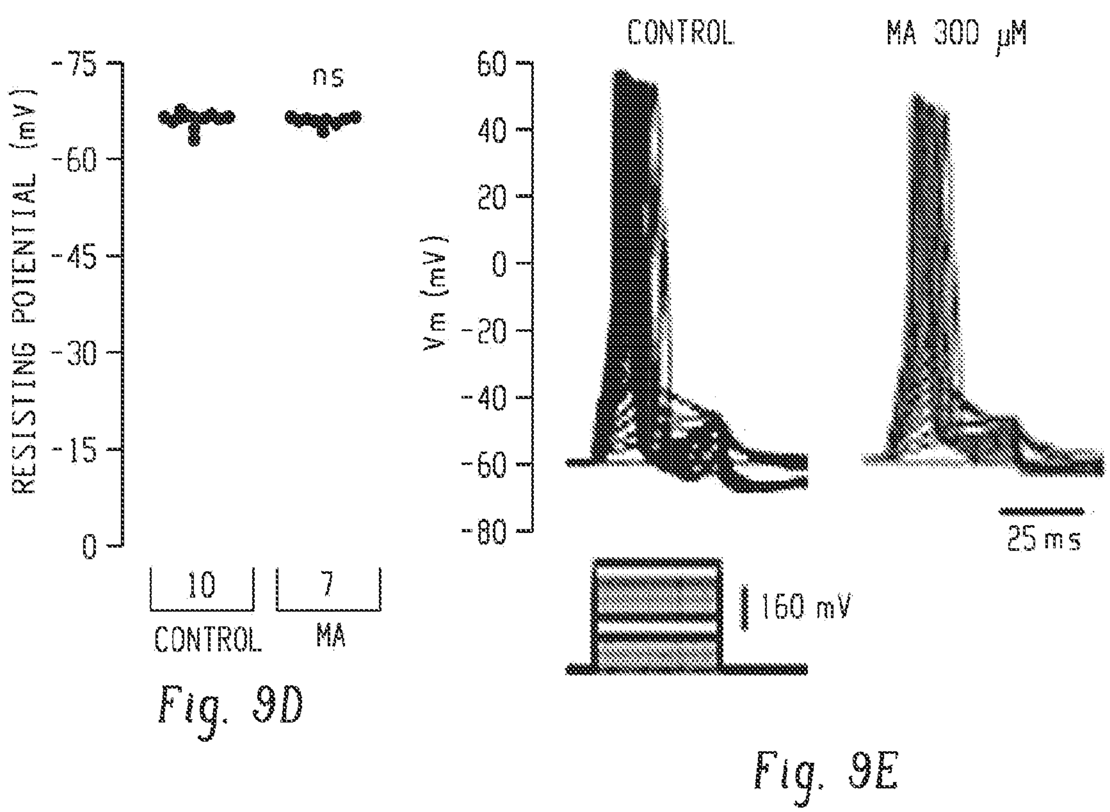
Fig. 9D
Fig. 9E
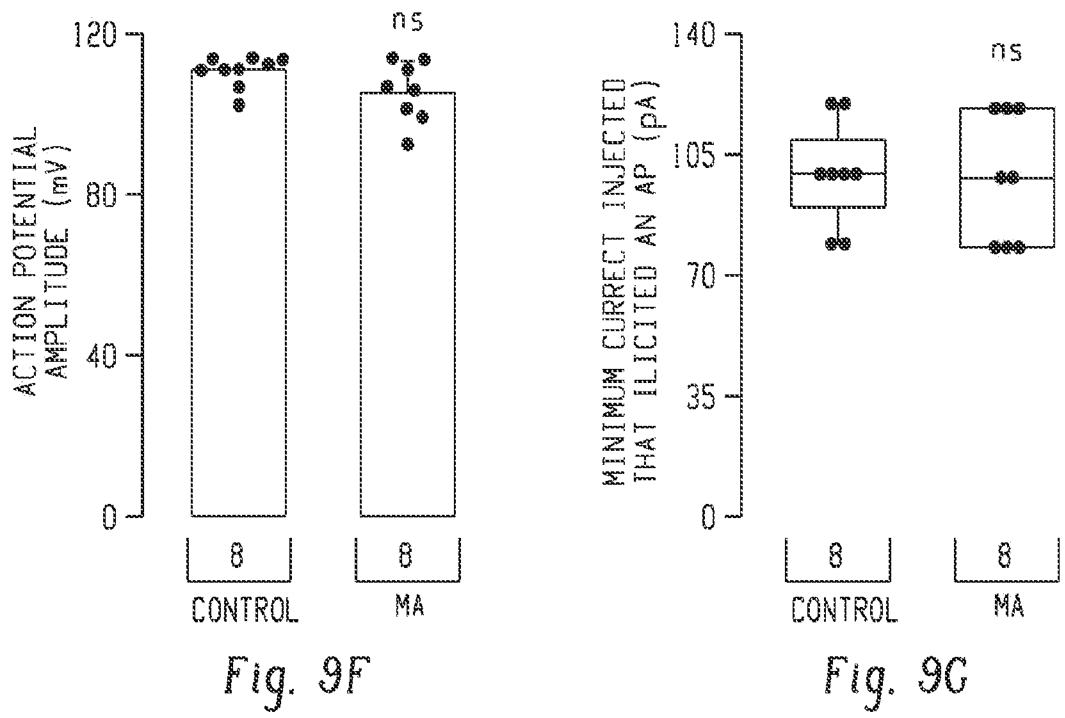
Fig. 9F
Fig. 9G

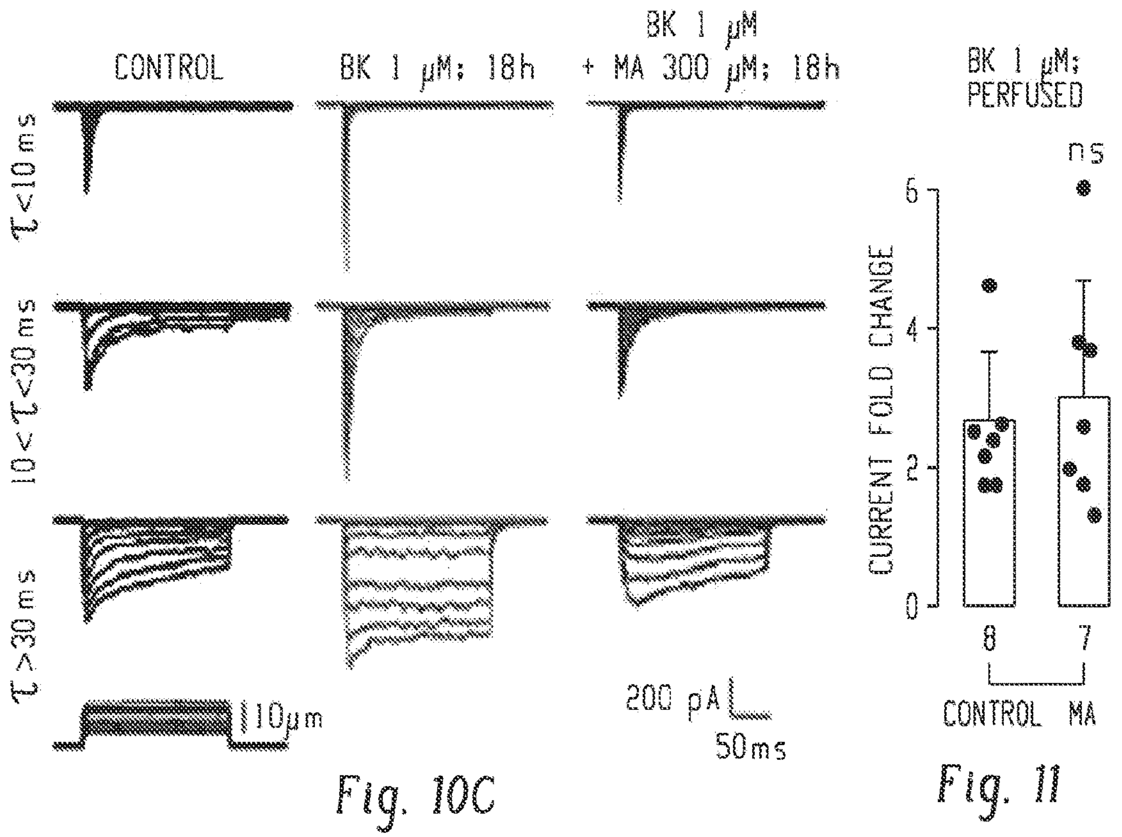
Fig. 10C
Fig. 11
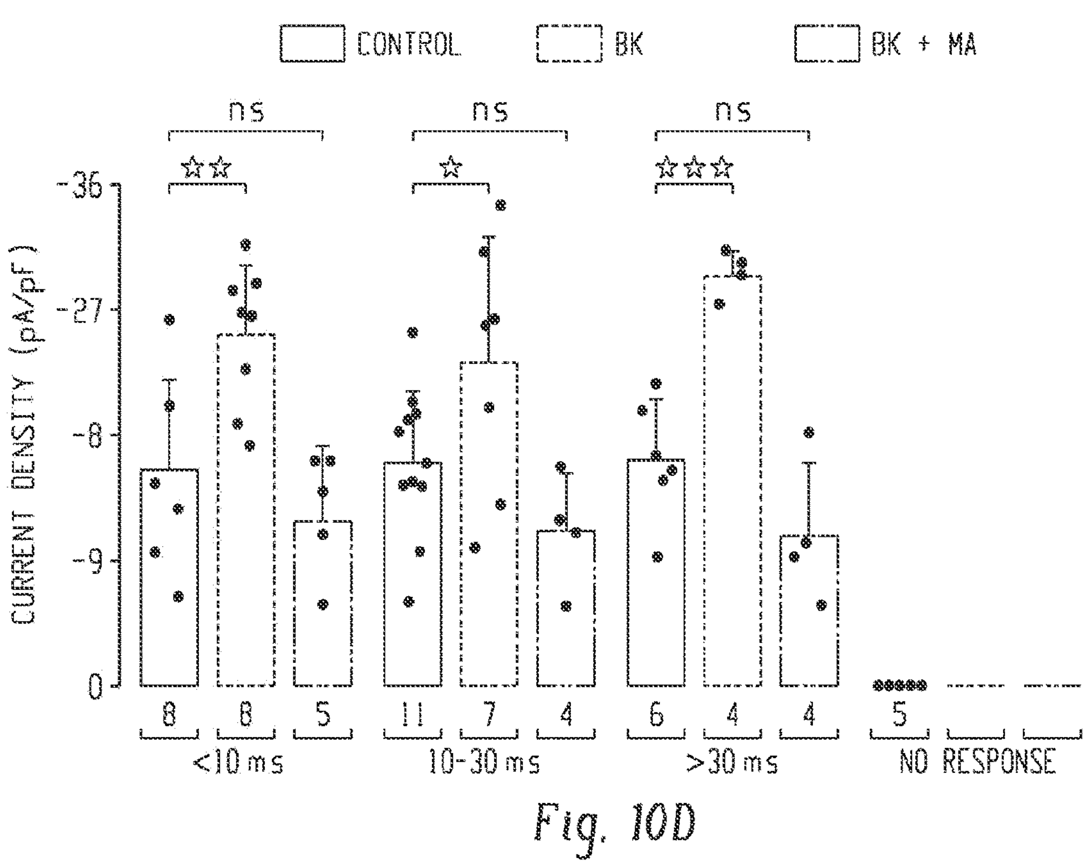
Fig. 10D

LEFT HIND PAW
SALINE OR
MARGARIC ACID
DAY 1
DAY 7
BASELINE
VON FREY
HARGREAVES
N=C=S 100
80
60
40
20
0
% WITHDRAWL
0
0.2
0.4
0.6
0.8
1
VON FREY (g)
SALINE BASELINE
MA BASELINE
SALINE DAY 7
MA DAY 7

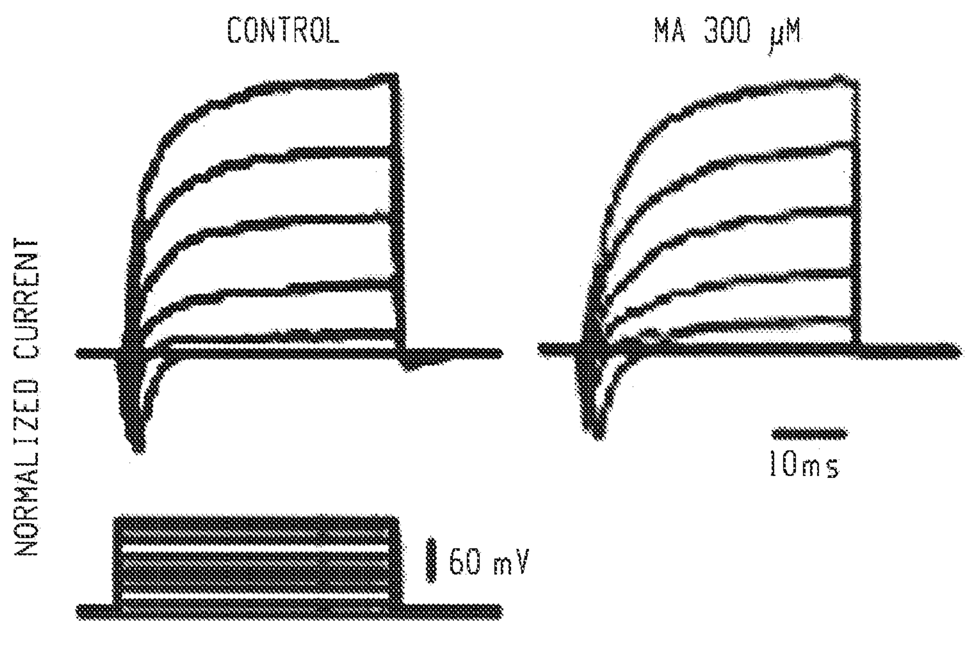
Fig. 13F
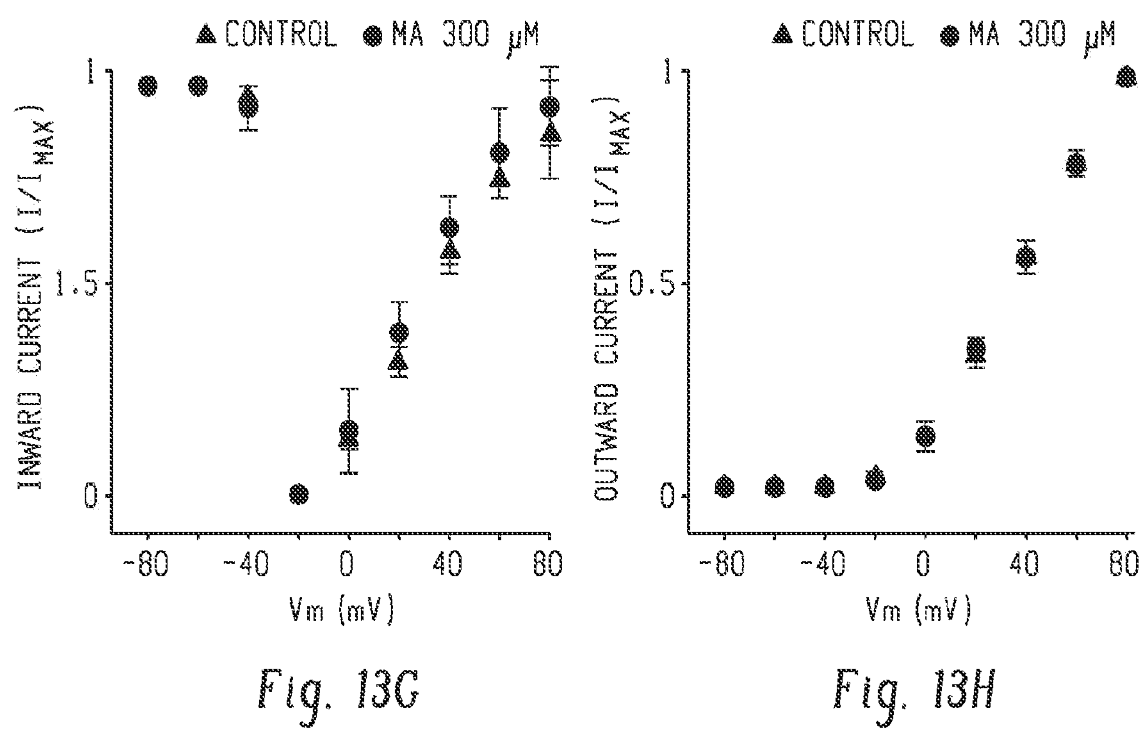
Fig. 13G
Fig. 13H

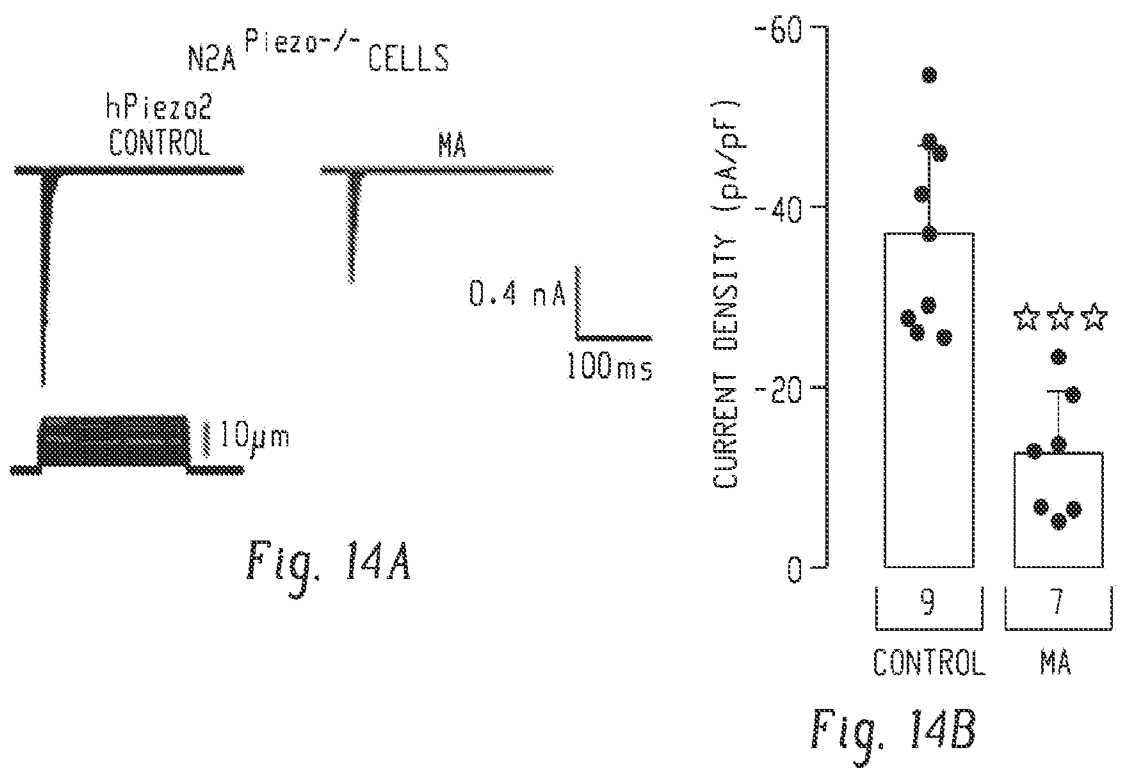
Fig. 14A
Fig. 14B
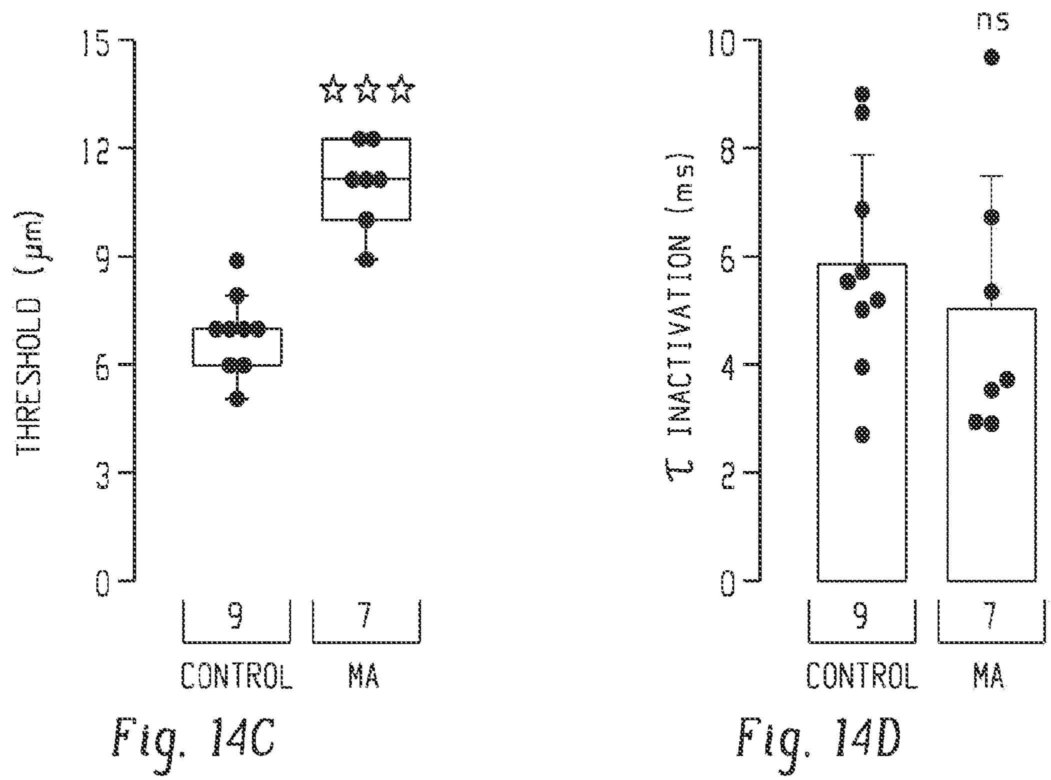
Fig. 14C
Fig. 14D

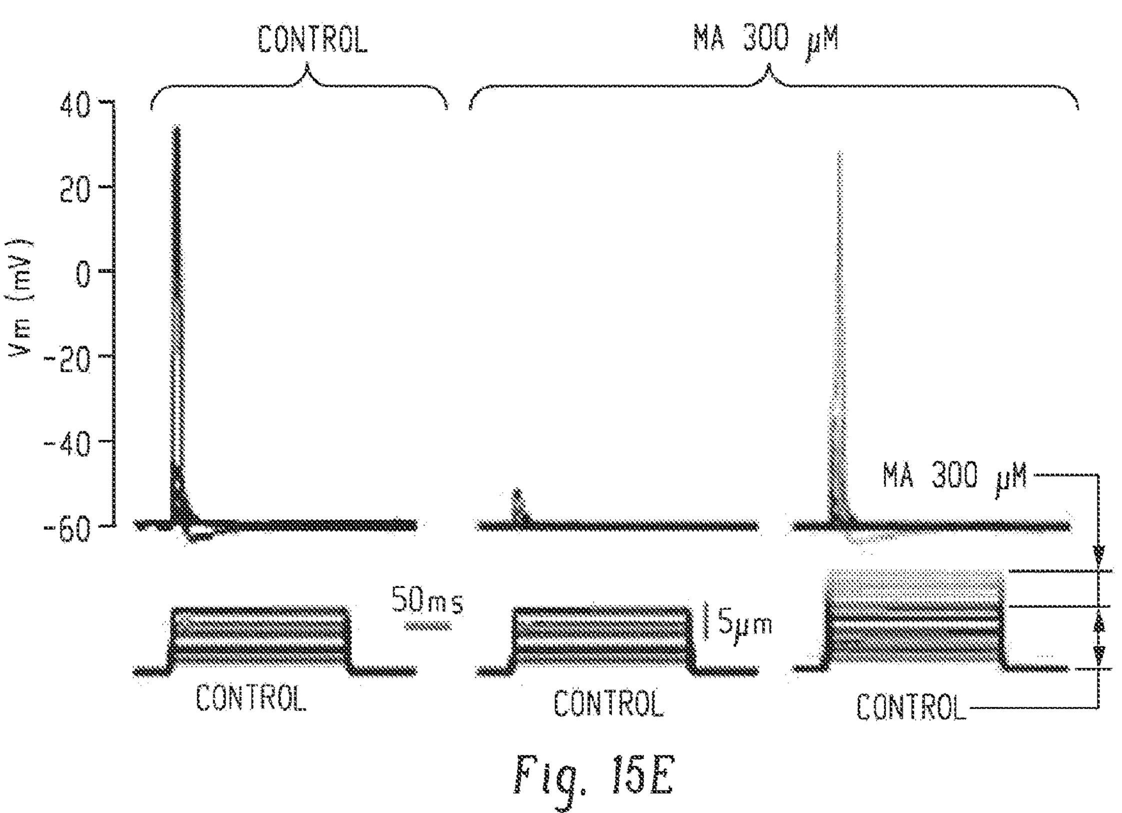
Fig. 15E
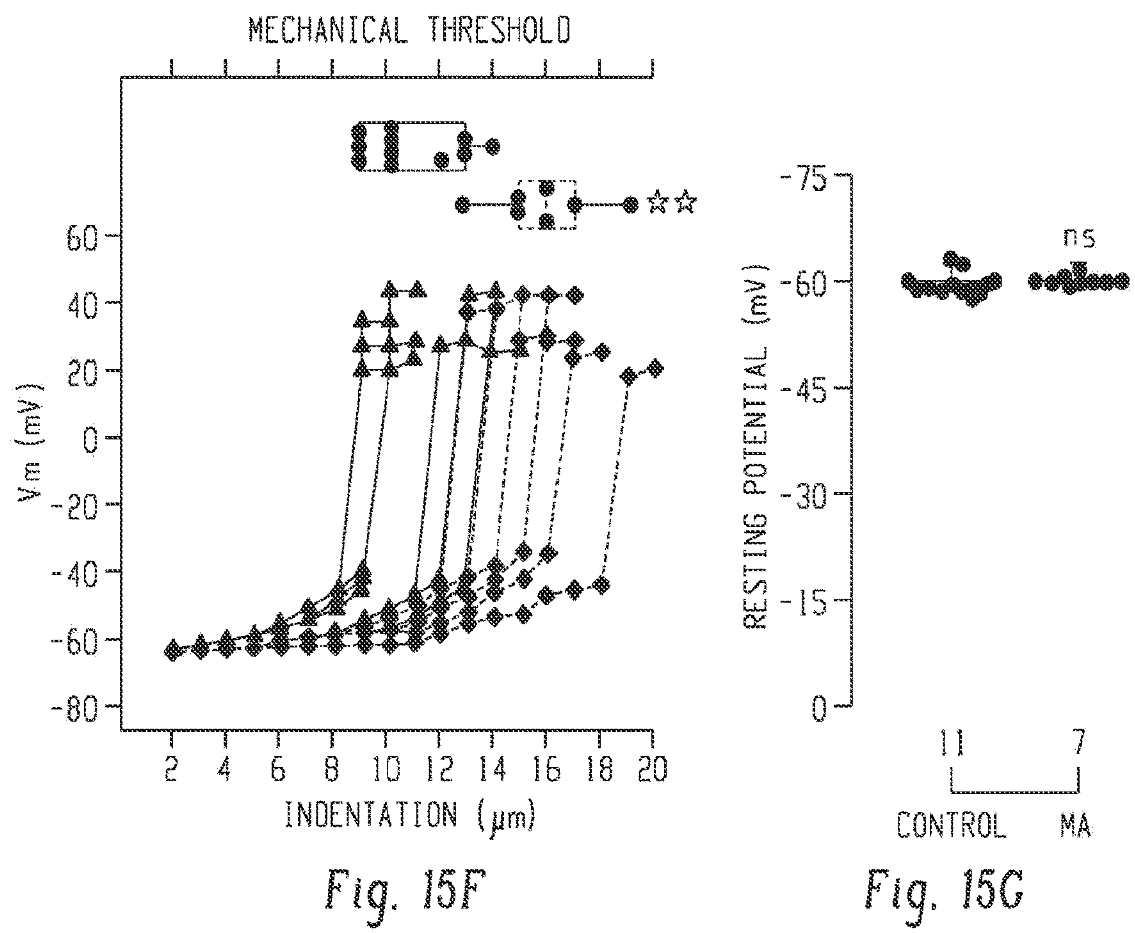
Fig. 15F
Fig. 15G

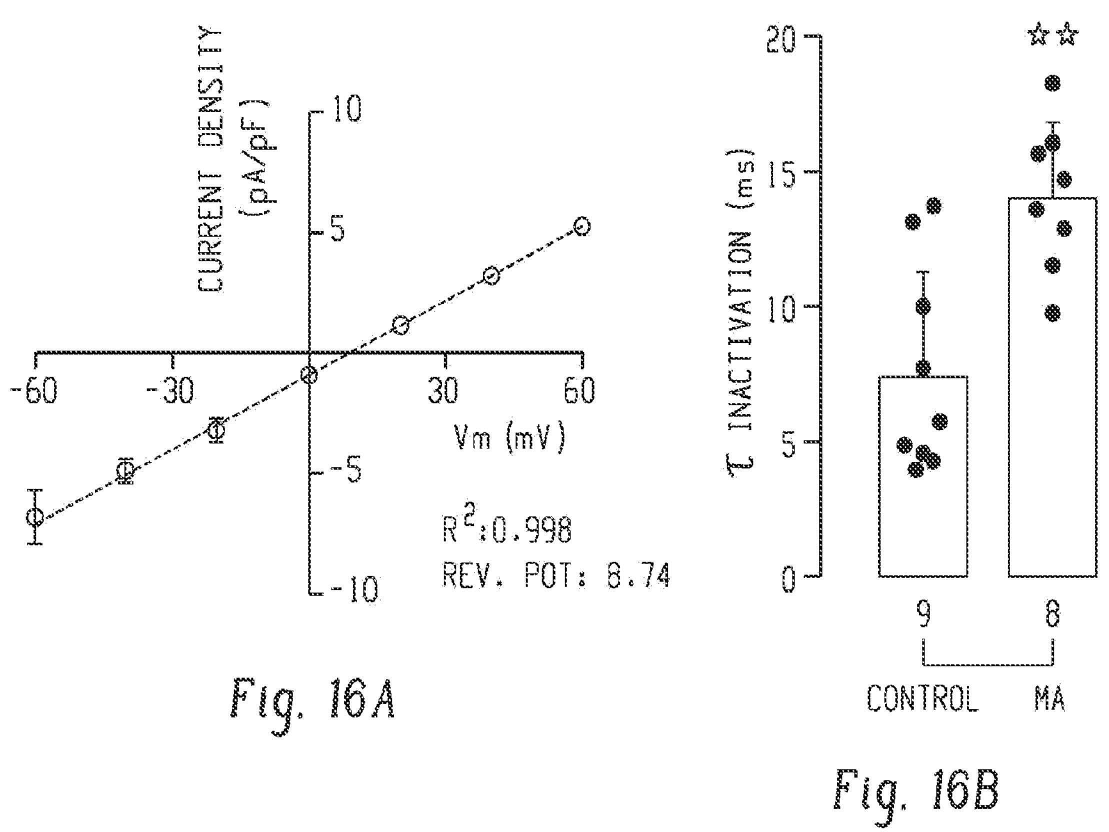
Fig. 16A
Fig. 16B
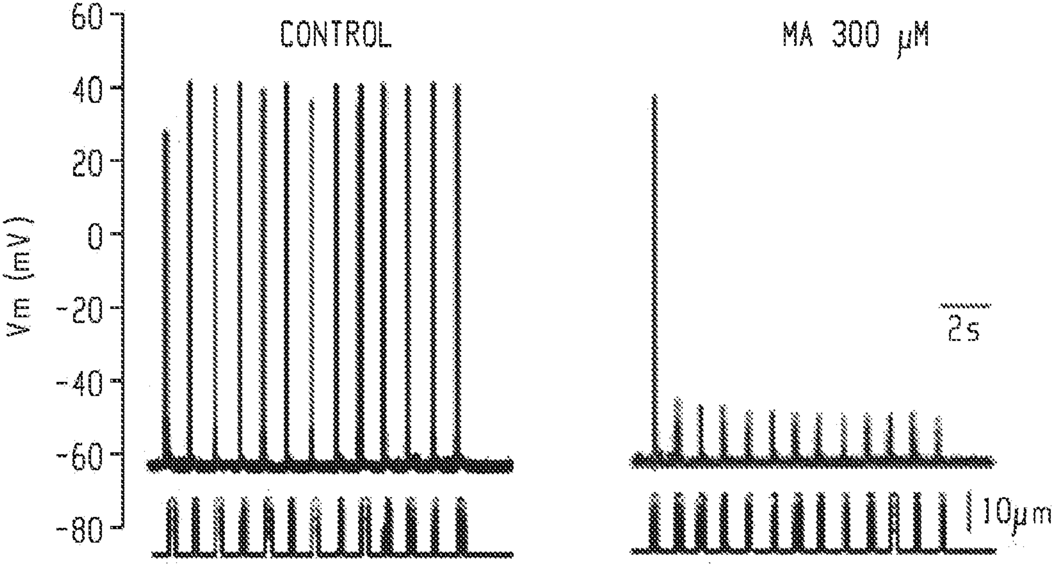
Fig. 16C

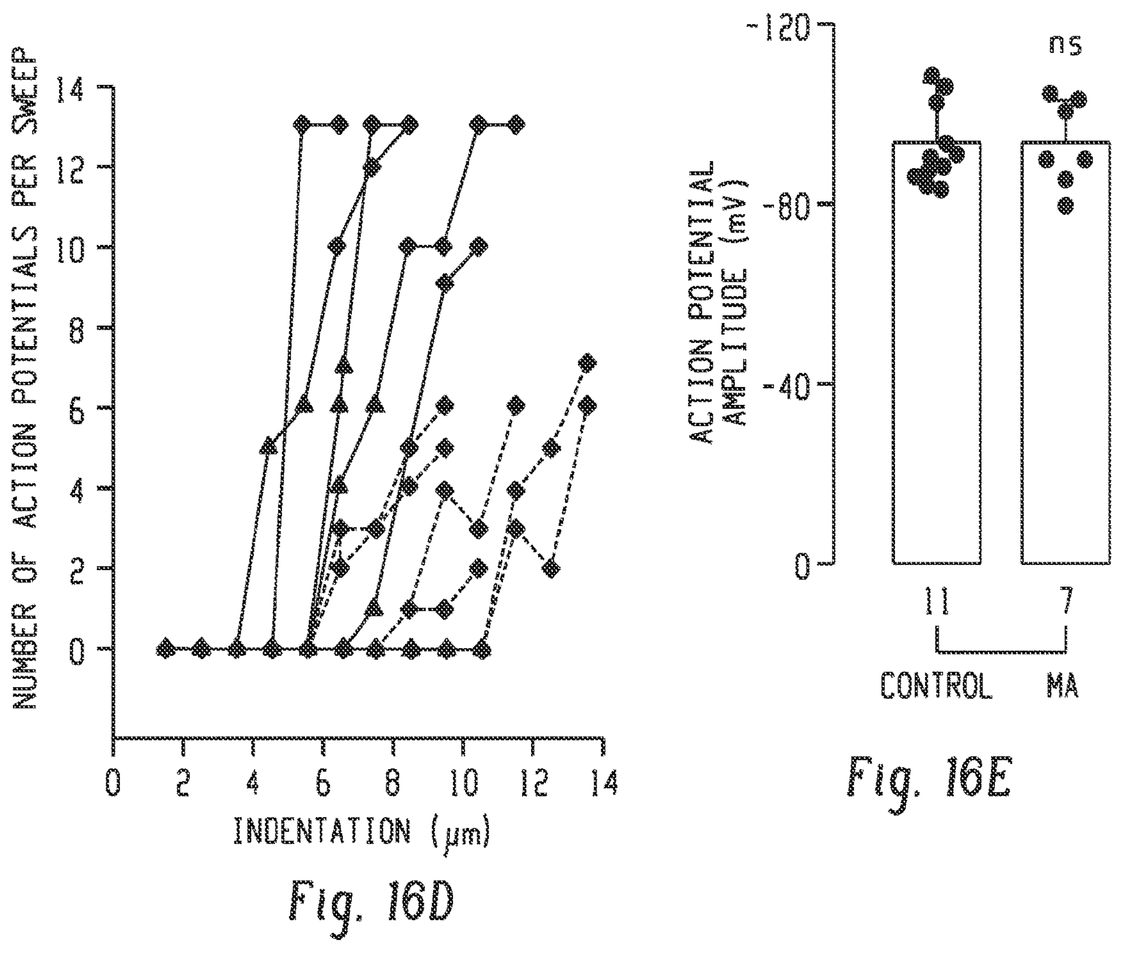
Fig. 16D
Fig. 16E
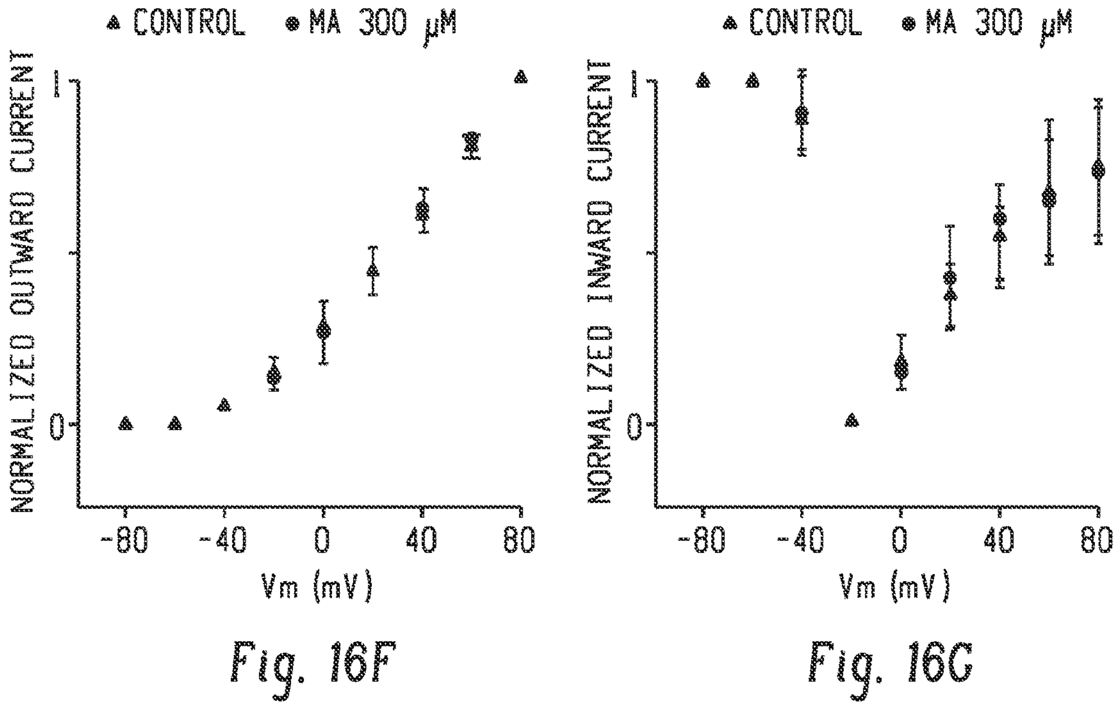
Fig. 16F
Fig. 16G

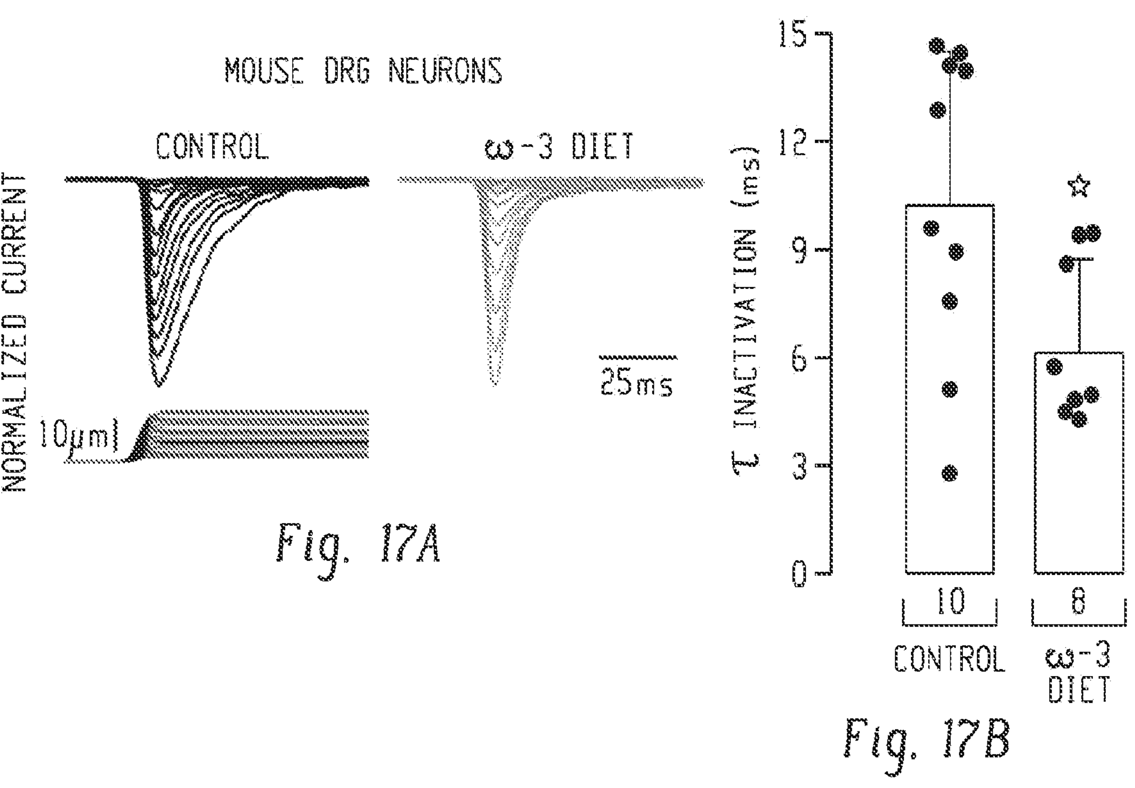
Fig. 17A
Fig. 17B
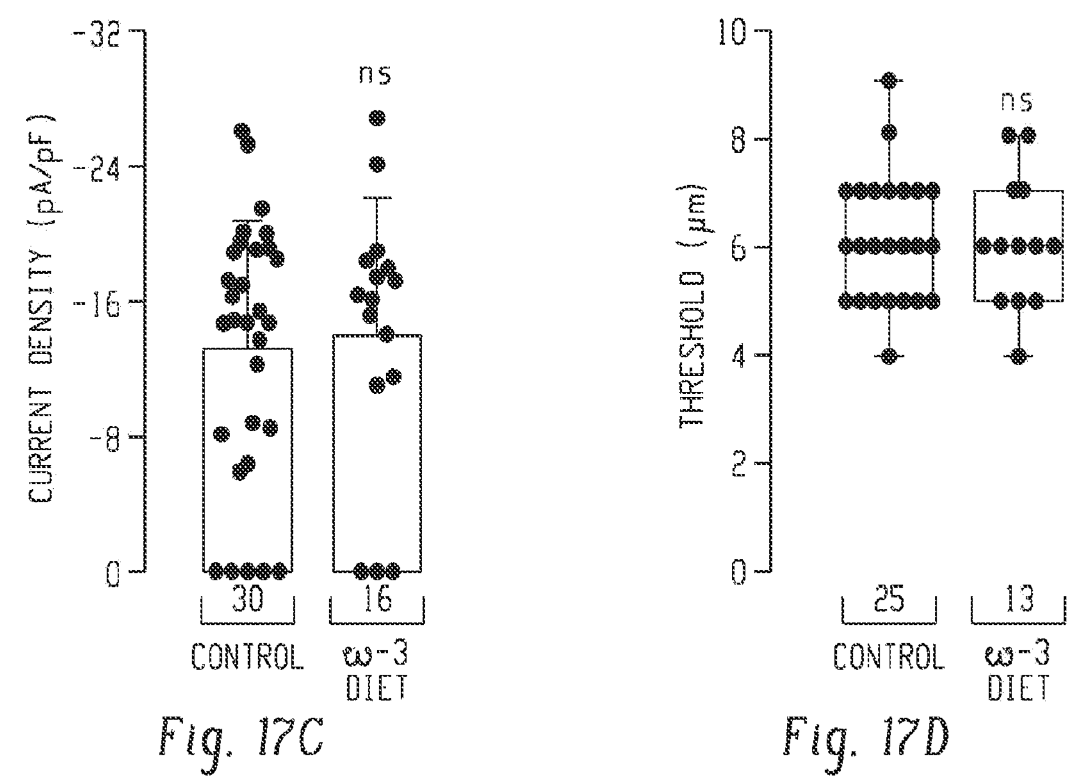
Fig. 17C
Fig. 17D

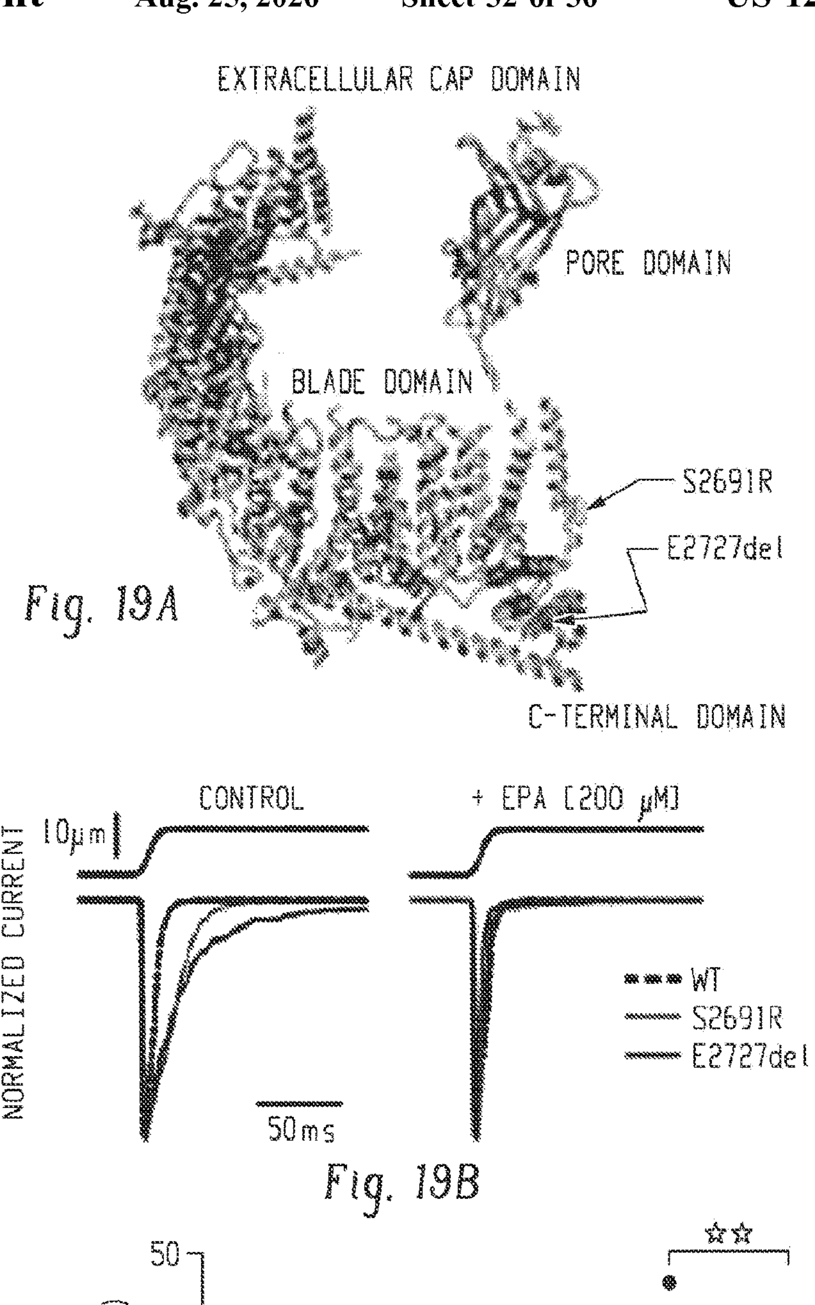
Fig. 19A
Fig. 19B
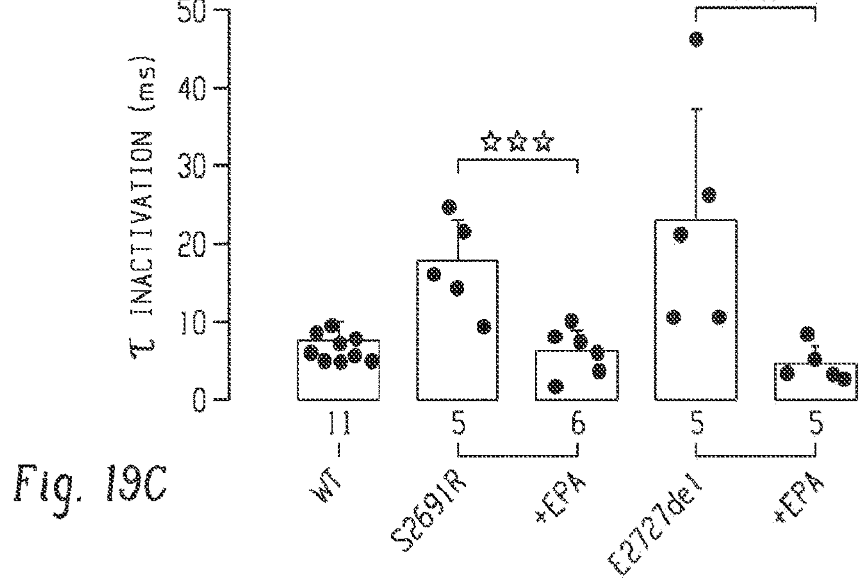
Fig. 19C

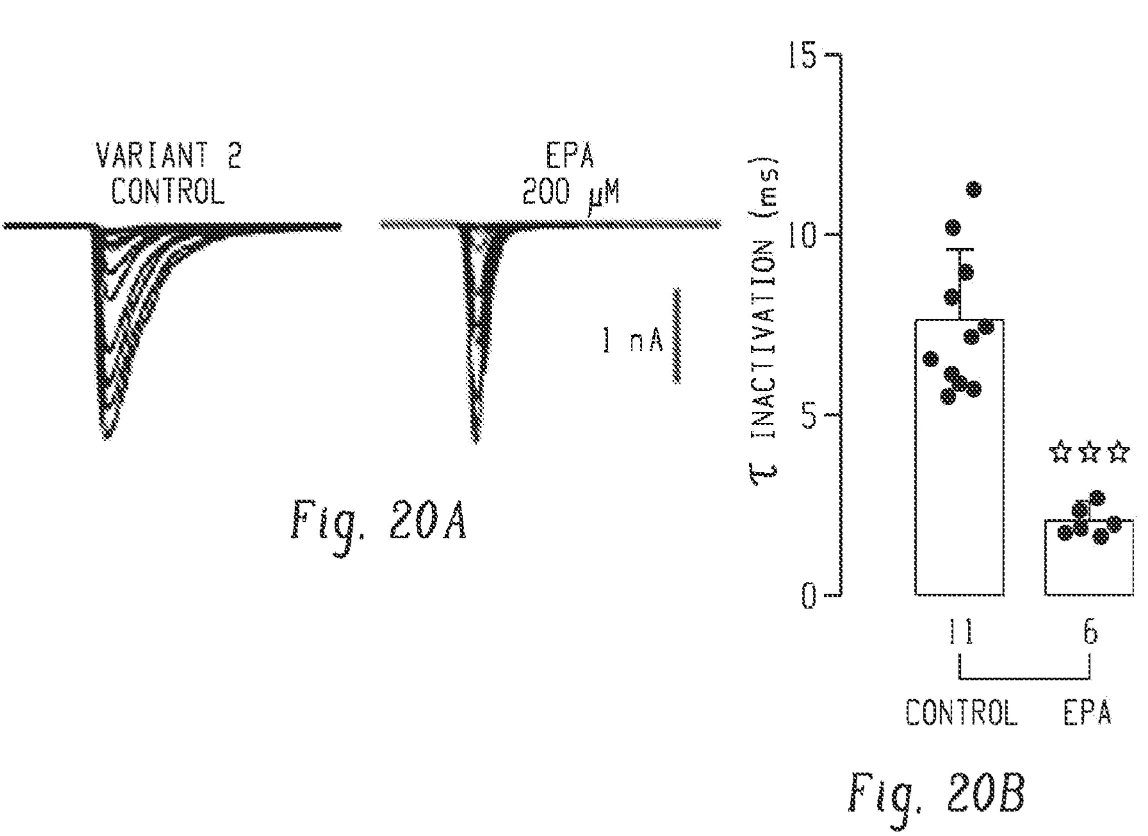
Fig. 20A
Fig. 20B
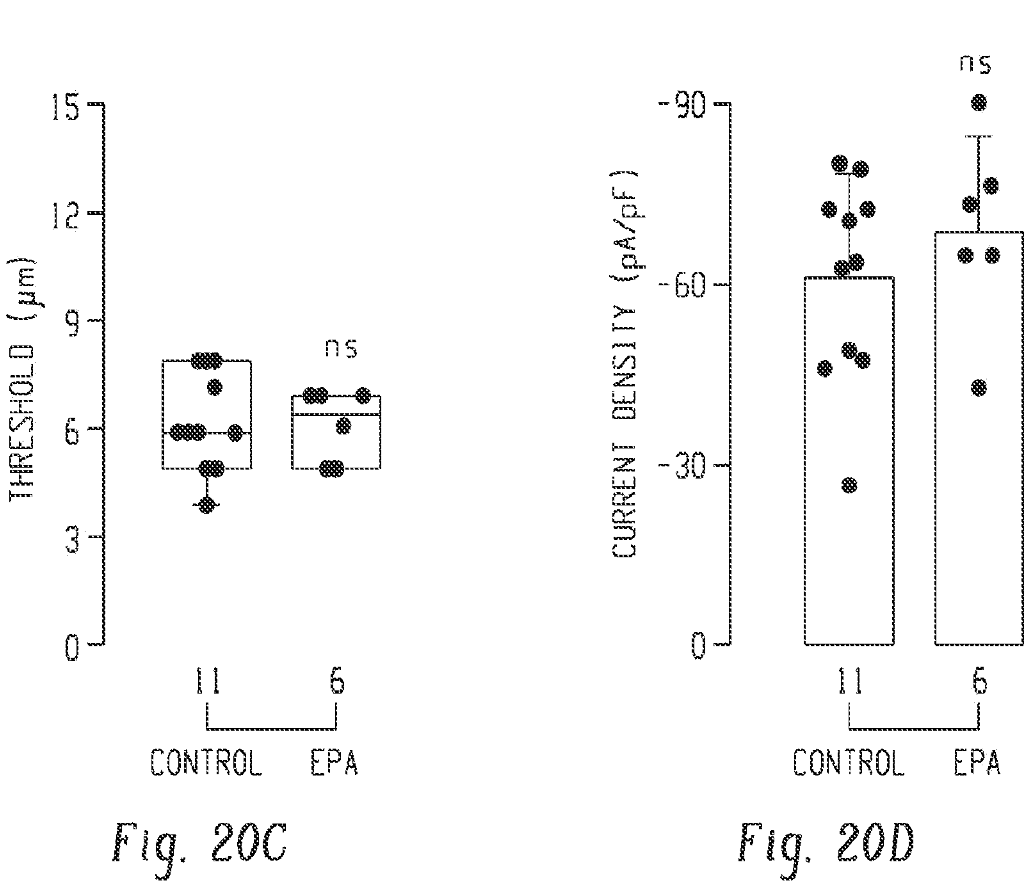
Fig. 20C
Fig. 20D

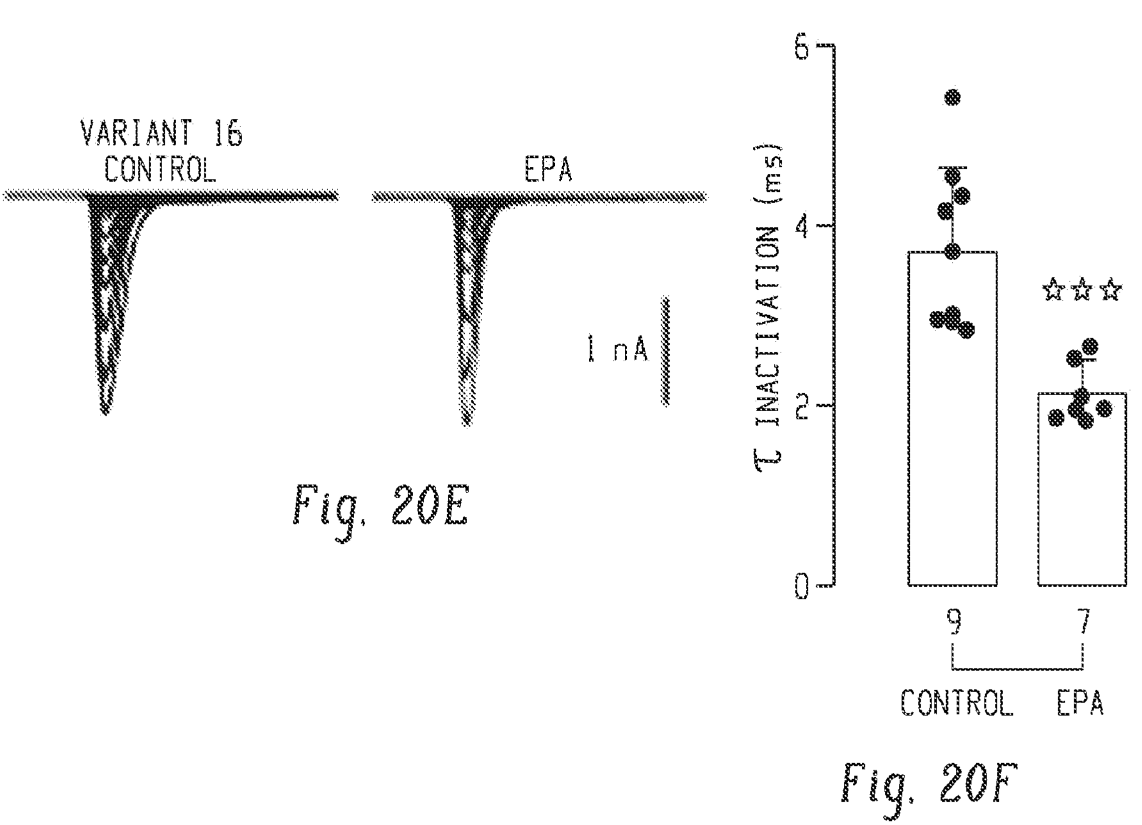
Fig. 20E
Fig. 20F
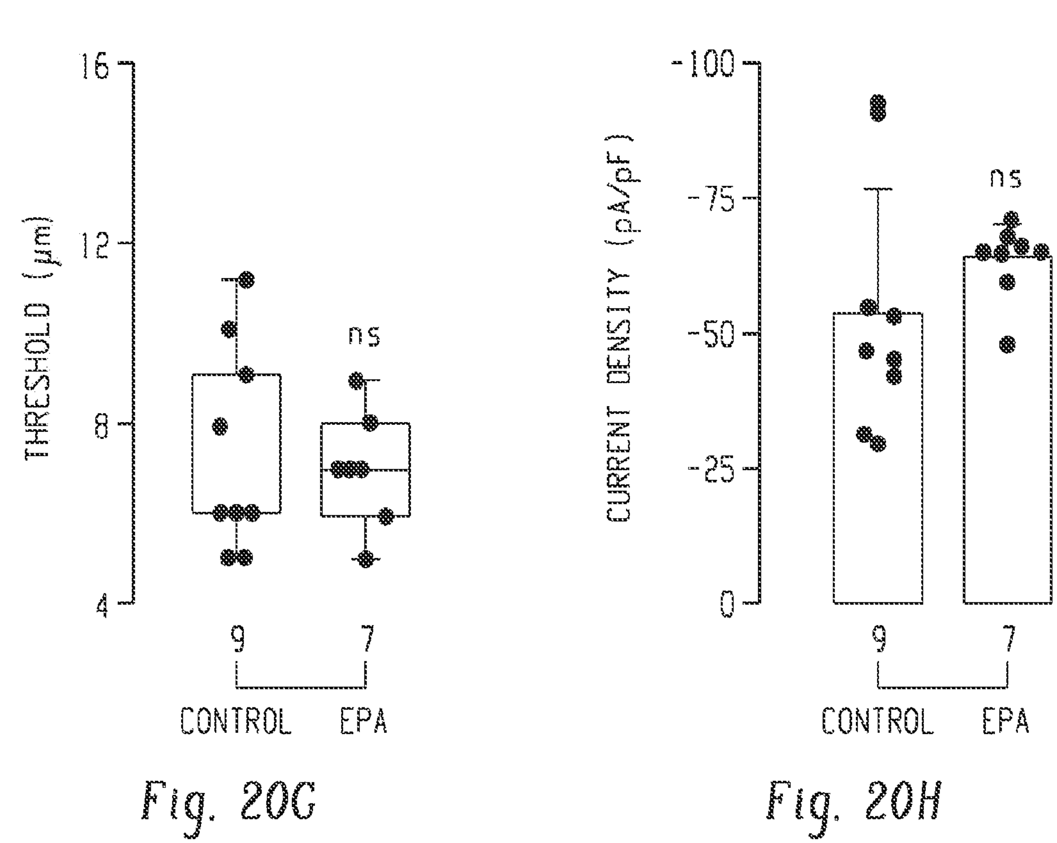
Fig. 20G
Fig. 20H

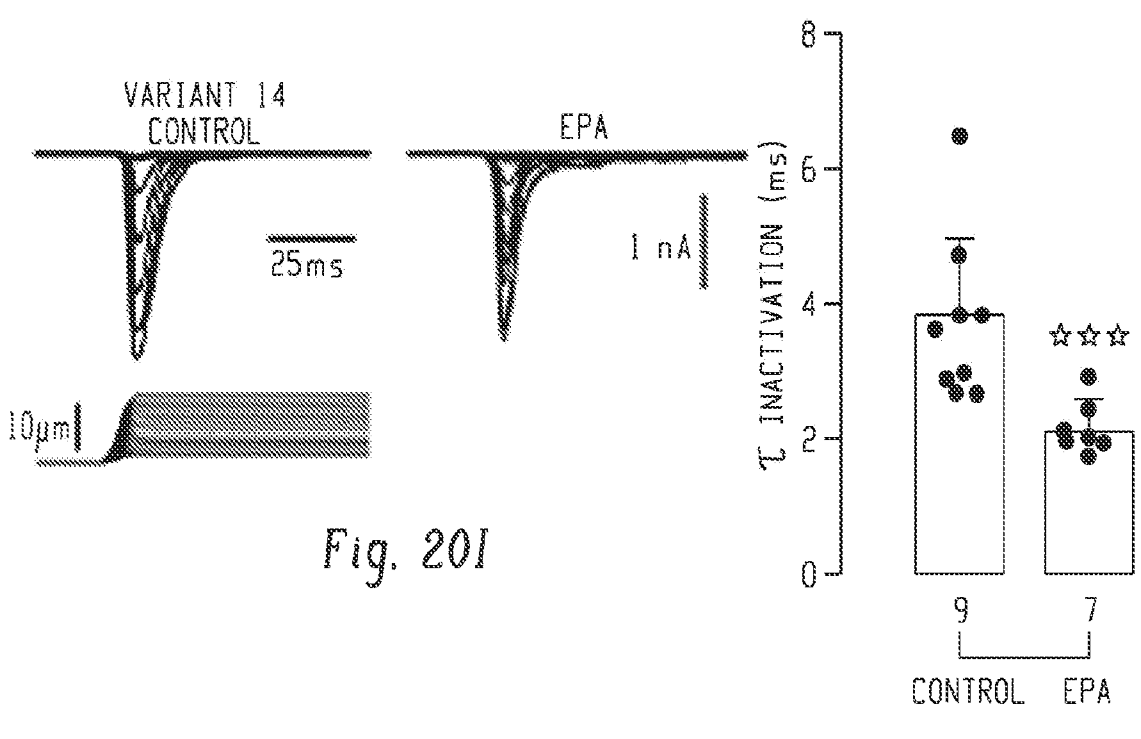
Fig. 20I
Fig. 20J
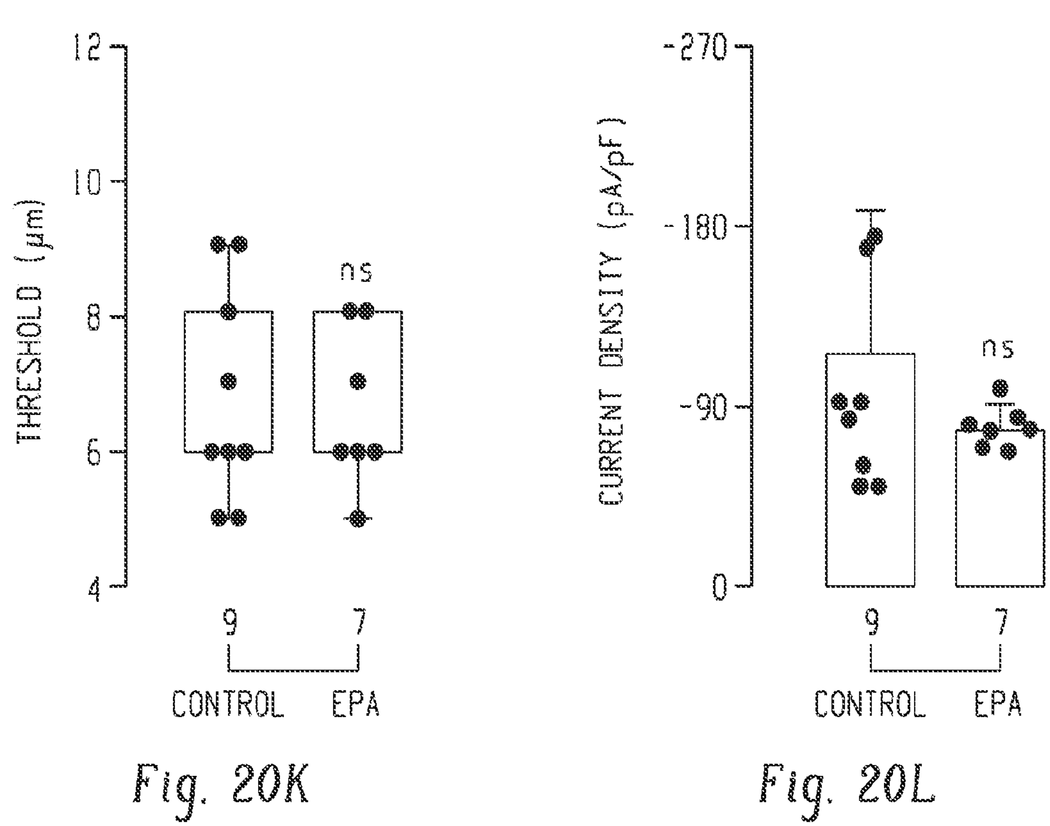
Fig. 20K
Fig. 20L

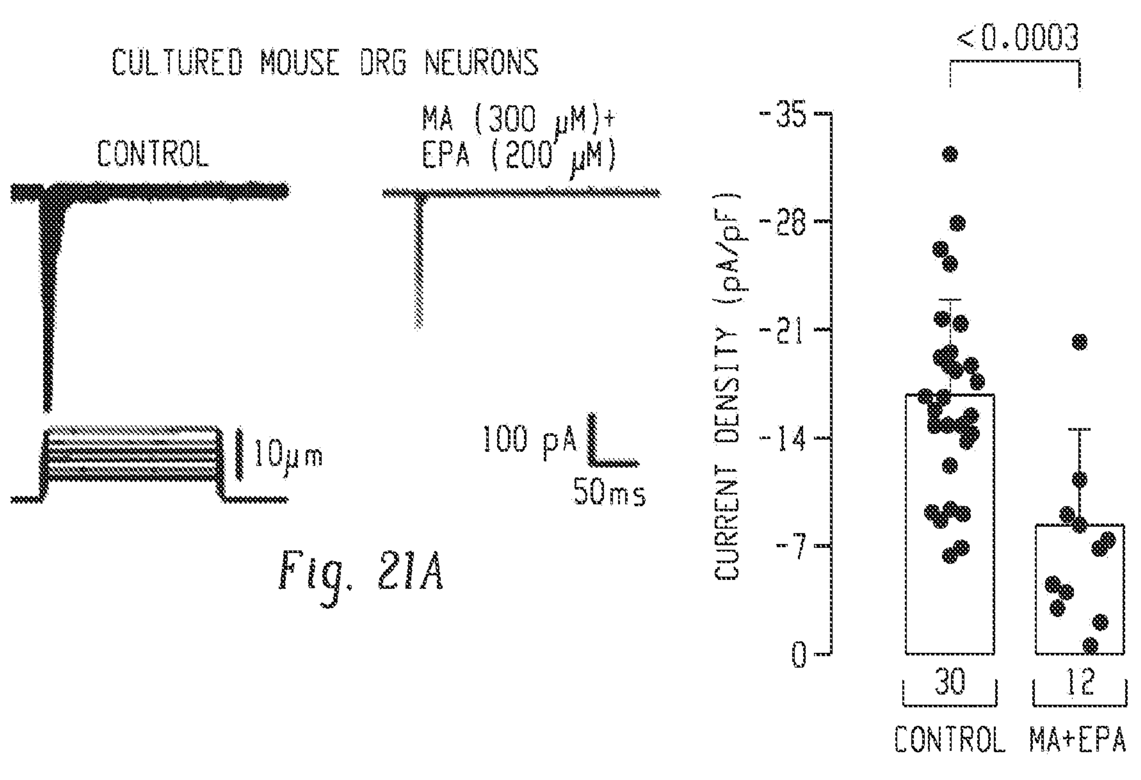
Fig. 21A
Fig. 21B
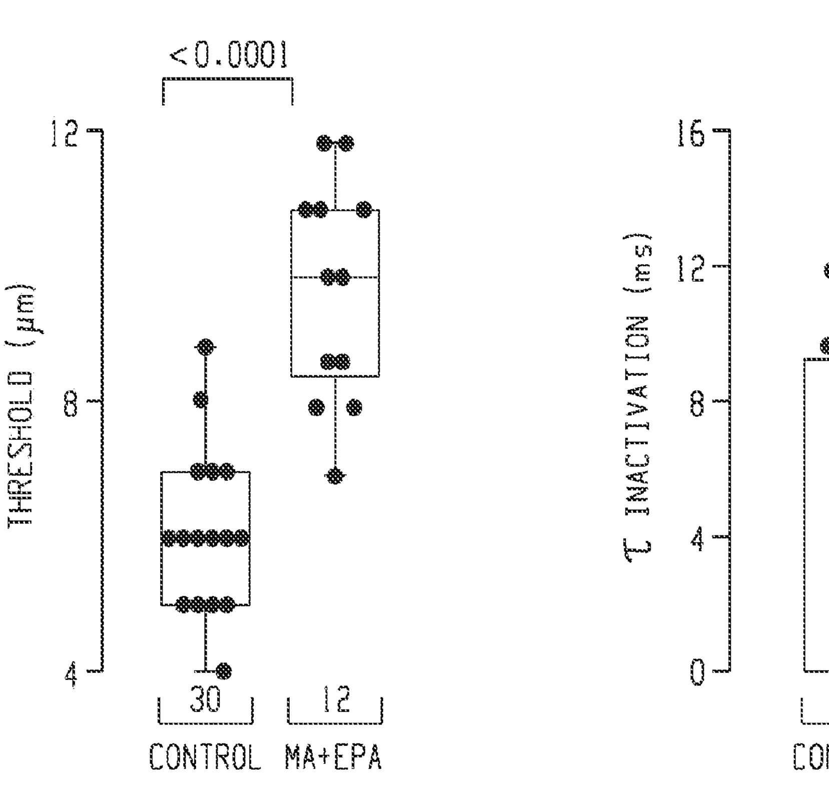
Fig. 21C
Fig. 21D

MARGARIC ACID DECREASES PIEZ02-MEDIATED PAIN

CROSS-REFERENCE TO RELATED APPLICATIONS

This application claims priority to U.S. Provisional Application 62/976,014 filed on Feb. 13, 2020, which is incorporated herein by reference in its entirety.

FIELD OF THE DISCLOSURE

The present disclosure is related to methods of treatment of pain using dietary fatty acids.

BACKGROUND

The skin is innervated by sensory neurons expressing mechanosensitive ion channels that allow the detection and discrimination of pleasant from painful touch. The PIEZO2 mechanosensitive ion channel is highly expressed in sensory neurons and Merkel cells where it mediates gentle touch (i.e., brush) and vibration. Importantly, research has also shown that PIEZO2 contributes to tactile allodynia (i.e., when innocuous sensations become painful under inflammatory conditions).

Mechanosensitive ion channels are known to be modulated by the mechanical properties of the membrane, intracellular and extracellular proteins, and/or cytoskeleton elements. There are several lines of evidence suggesting that PIEZO2 channels interact with cellular components to fulfill its physiological role. For instance, PIEZO2's association with stomatin-like protein 3 and cholesterol increases its sensitivity to mechanical stimuli, sensitization by inflammatory agents such as bradykinin, and regulation by phosphoinositide lipids. Interestingly, PIEZO2 requires cytoskeleton elements such as actin and tubulin for normal function. Together, these data indicate complex interactions that work in concert to tune PIEZO2 function.

Recent findings that Piezo2-deficient humans and knockout mice fail to develop sensitization and painful reactions to innocuous touch after skin inflammation suggest that targeting this receptor may be a viable strategy to treating tactile allodynia.

What are needed are chemical compounds that interact with Piezo receptors and their use to mediate the function of Piezo receptors.

BRIEF SUMMARY

In an aspect, method of treating pain comprises administering to a subject in need of treatment for pain a pharmaceutical composition comprising a therapeutically effective amount of margaric acid.

In another aspect, a pharmaceutical composition comprises margaric acid and a pharmaceutically acceptable excipient.

In yet another aspect, a composition for the treatment of pain comprises margaric acid, eicosapentaenoic acid, and a pharmaceutically acceptable excipient.

BRIEF DESCRIPTION OF THE DRAWINGS

FIG. 1*a-f* show that margaric acid (MA) inhibits heterologously-expressed mouse PIEZO2 currents in N2A$^{Piezo1-/-}$ cells. FIG. 1*a* shows representative whole-cell patch-clamp recordings elicited by mechanical stimulation (at −60 mV) of control and margaric acid (MA) (1, 50, 200, 300, 400, and 600 μM)-treated N2A$^{Piezo1-/-}$ cells transfected with Piezo2 variant 2 (V2). FIG. 1*b* shows normalized current densities elicited by maximum displacement of MA-treated N2A$^{Piezo1-/-}$ cells transfected with Piezo2 V2. A Boltzmann function, Eq. (2), was fitted to the data (IC50=190.6±14.7 SEM). Circles are mean±SD. n is denoted above the x-axis of panel c. FIG. 1*c* boxplots show mean, median, and the 75th to 25th percentiles of the displacement thresholds required to elicit PIEZO2 V2 currents of control and N2A$^{Piezo1-/-}$ cells. n is denoted above the x axis. One-way ANOVA and Bonferroni test. FIG. 1*d* shows representative PIEZO2 currents (at −60 mV) of control and MA (50 μM each day for 4 days)-treated N2A$^{Piezo1-/-}$ cells transfected with Piezo2 V2. FIG. 1*e* shows PIEZO2 V2 current densities elicited by maximum displacement of control and MA (50 μM for 18 h, and each day for 4 days)-treated N2A$^{Piezo1-/-}$ cells. n is denoted above the x-axis. One-way ANOVA and Bonferroni test. FIG. 1*f* boxplots show mean, median and the 75th to 25th percentiles of the displacement thresholds required to elicit PIEZO2 V2 currents of control and MA (50 μM each day for 4 days)-treated N2A$^{Piezo1-/-}$ cells transfected with PIEZO2 V2. n is denoted above the x-axis. Unpaired t-test. Asterisks indicate values significantly different from control (***p<0.001) and n.s. indicates values not significantly different from the control.

FIG. 2*a* shows current densities elicited by maximum displacement of control and MA (1, 25, 50, 100, 200, 300, 400, and 600 μM)-treated N2A$^{Piezo1-/-}$ cells transfected with Piezo2 Variant (V2). Bars are mean±SD. n is denoted above the x-axis. Unpaired t-test, unpaired t-test with Welch's correction, and Mann-Whitney test. FIG. 2*b* shows PIEZO2 V2 time constants of inactivation elicited by maximum displacement of control and MA (1, 25, 50, 100, 200, 300, 400, and 600 μM)-treated N2A$^{Piezo1-/-}$ cells. Bars are mean±SD. N is denoted above the x-axis. One-way ANOVA and Bonferroni test. FIG. 2*c* shows PIEZO2 V2 time constant of inactivation elicited by maximum displacement of control and MA (50 μM each day for 4 days)-treated N2APiezo1−/− cells. Bars are mean±SD. n is denoted above the x-axis. Unpaired t-test. FIG. 2*d* shows representative currents (at −60 mV) of control and MA (25 μM each day for 8 days)-treated N2A$^{Piezo1-/-}$ cells transfected with Piezo2 V2. FIG. 2*e* shows PIEZO2 V2 current densities elicited by maximum displacement of control and MA (25 μM each day for 8 days)-treated N2A$^{Piezo1-/-}$ cells. n is denoted above the x-axis. Unpaired t-test. FIG. 2*f* boxplots show mean, median, and the 75th to 25th percentiles of the displacement thresholds required to elicit PIEZO2 V2 currents of control and MA (25 μM each day for 8 days)-treated N2A$^{Piezo1-/-}$ cells transfected with Piezo2 V2, n is denoted above the x-axis. Unpaired t-test. FIG. 2*g* shows PIEZO2 V2 time constant of inactivation elicited by maximum displacement of control and MA (25 μM each day for 8 days)-treated N2A$^{Piezo1-/-}$ cells. Bars are mean±SD. n is denoted above the x-axis. Unpaired t-test. Asterisks indicate values significantly different from control (*p<0.001 and p<0.01) and n.s. indicates not significantly different from the control.

FIG. 3*a-i* support that MA inhibits heterologously-expressed mouse PIEZO2 currents in N2A$^{Piezo1-/-}$ cells. FIG. 3*a* is a schematic representation of absent (black) and/or present (white) exons of Piezo2 variants (V). FIG. 3*b* shows representative whole-cell patch-clamp recordings of control and MA (300 μM; 18 h)-treated N2A$^{Piezo1-/-}$ cells transfected with Piezo2 V14. FIG. 3*c* shows current densities elicited by maximum displacement of control and MA (300 μM; 18 h)-treated N2A$^{Piezo1-/-}$ cells transfected with Piezo2 V14. Bars are mean±SD. n is denoted above the x-axis. Mann-Whitney test. FIG. 3*d* boxplots show mean, median, and 75th to 25th percentiles of the displacement thresholds required to elicit currents of control and MA (300 μM; 18 h)-treated N2A$^{Piezo1-/-}$ cells transfected with Piezo2 V14. n is denoted above the x-axis. Unpaired t-test. FIG. 3*e* shows time constants of inactivation elicited by maximum displacement of control and MA (300 μM; 18 h)-treated N2A$^{Piezo1-/-}$ cells transfected with Piezo2 V14. Bars are mean±SD. n is denoted M. FIG. 3*f* shows representative whole-cell patch-clamp recordings of control and MA (300 μM; 18 h)-treated N2A$^{Piezo1-/-}$ cells transfected with Piezo2 V16. FIG. 3*g* shows current densities elicited by maximum displacement of control and MA (300 μM; 18 h)-treated N2A$^{Piezo1-/-}$ cells transfected with Piezo2 V16. Bars are mean±SD. n is denoted above the x-axis. Unpaired t-test with Welch's correction. FIG. 3*h* boxplots show mean, median, and 75th to 25th percentiles of the displacement thresholds required to elicit currents of control and MA (300 μM; 18 h)-treated N2A$^{Piezo1-/-}$ cells transfected with Piezo2 V16. n is denoted above the x-axis. Mann-Whitney test. FIG. 3*i* shows time constants of inactivation elicited by maximum displacement of control and MA (300 μM; 18 h)-treated N2A$^{Piezo1-/-}$ cells transfected with Piezo2 V1. Bars are mean±SD. n is denoted above the x-axis. Unpaired t-test. Asterisks indicate values significantly different from control (**p<0.01 and *p<0.05) and n.s. indicates not significantly different from the control.

FIG. 4*a* shows normalized current density elicited by maximum displacement of MA (1, 10, 25, 50, 100, and 300 μM; 18 h)-supplemented N2A cells (expressing endogenous Piezo1) and MA (1, 25, 50, 100, 200, 300, 400, and 600 μM; 18 h)-supplemented N2A$^{Piezo1-/-}$ cells transfected with Piezo2, (triangles and circles, respectively). A Boltzmann function, Eq. (2), was fitted to the data (PIEZO1 IC50=28.3±3.4 SEM; PIEZO2 IC50=190.6±14.7 SEM). Symbols are mean±SD. FIG. 4*b* shows normalized current densities elicited by maximum displacement of MA (1, 25, 50, 100, 200, 300, 400 and 600 μM; 18 h)-supplemented. N2A$^{Piezo1-/-}$ cells transfected with PIEZO2, treated with and without latrunculin A. A Boltzmann function, Eq. (2), was fitted to the data (MA IC50=190.6±14.7 SEM; MA+LatA IC50=75.4±13.3 SEM). Circles are mean±SD. FIG. 4*c* shows normalized current densities elicited by maximum displacement of MA (1, 10, 25, 50, 100, and 300 μM; 18 h)-supplemented N2A cells (expressing endogenous Piezo1). A Boltzmann function, Eq. (2), was fitted to the data (MA IC50=28.3±3.4 SEM; MA+LatA IC50=25.6±8.4 SEM). Triangles are mean±SD. FIG. 4*d* shows a ribbon representation of PIEZO2 monomer (PDB ID: 6KG7; gray) highlighting the residues that were exchanged for those of PIEZO1. FIG. 4*e* shows inhibition by MA (100 μM)-supplementation of N2A cells and N2A$^{Piezo1-/-}$ cells transfected with Piezo2 and Piezo2-Piezo1 beam chimera, n is denoted above the x-axis. Unpaired t-test and Mann-Whitney test. FIG. 4*f* shows normalized current densities elicited by maximum displacement of MA (100 μM; 18 h)-supplemented N2A cells (expressing endogenous Piezo1) and N2A cells transfected with Piezo2 and Piezo2-Piezo1 beam chimera treated with and without latrunculin. n is denoted above the x-axis, Unpaired t-test (for PIEZO1) and Mann-Whitney test (for PIEZO2 and PIEZO2-Piezo ibeam chimera). Asterisks indicate values significantly different from control (p<0.01 and *p<0.001) and n.s. indicates values not significantly different from the control.

FIG. 5*a* shows representative whole-cell patch-clamp recordings elicited by mechanical stimulation (at −60 mV) of control and MA (1, 25, 50, 100, 200, 300, 400, and 600 μM)-supplemented N2A$^{Piezo1-/-}$ cells transfected with Piezo2 V2, treated with and without Latrunculin A, FIG. 5*b* shows current densities elicited by maximum displacement of control and MA (1, 25, 50, 100, 200, 300, 400, and 600 μM)-supplemented N2A$^{Piezo1-/-}$ cells transfected with Piezo2 V2 treated with and without Latrunculin A. n is denoted above the x-axis. Unpaired t-test, Mann-Whitney, and Unpaired t-test with Welch's correction. FIG. 5*c* shows representative whole-cell patch-clamp recordings elicited by mechanical stimulation (at −60 mV) of control and MA (1, 10, 25, 50, 100, and 300 μM)-supplemented N2A cells (expressing endogenous Piezo1), treated with and without Latrunculin A. FIG. 5*d* shows current densities elicited by maximum displacement of control and MA (1, 10, 25, 50, 100, and 300 μM)-supplemented N2A cells (expressing endogenous Piezo1) treated with and without Latrunculin A treated with and without Latrunculin A. n is denoted above the x-axis. Unpaired t-test with Welch's correction, Unpaired t-test, and Mann-Whitney. Asterisks indicate values significantly different from control (*p<0.001, p<0.01 and *p<0.05) and n.s. indicates not significantly different from the control.

FIG. 6*a* shows representative whole-cell patch-clamp recordings elicited by mechanical stimulation (at −60 mV) of control, MA (100 μM for 18 h)-treated N2A$^{Piezo1-/-}$ cells transfected with Piezo2-Piezo1 beam chimera, with and without Latrunculin A (1 μM for 1 h). FIG. 6*b* shows current-voltage relationship of PIEZO2-PIEZO1 chimera mechano-dependent currents as determined by whole-cell patch-clamp experiments. Circles are mean±SD. n=6. FIG. 6*c* boxplots show mean, median, and 75th to 25th percentiles of the displacement thresholds required to elicit currents of control, MA (100 μM for 18 h)-treated N2A$^{Piezo1-/-}$ cells transfected with Piezo2-Piezo1 beam chimera, with and without Latrunculin A (1 μM for 1 h). n is denoted above the x-axis. Mann-Whitney test (for control vs. MA and control vs. MA+LatA) and unpaired t-test (for MA vs. MA+LatA). FIG. 6*d* shows time constants of inactivation elicited by maximum displacement of Piezo2 V2 and Piezo2-Piezo1 beam chimera transfected in N2A$^{Piezo1-/-}$ cells. Bars are mean±SD. n is denoted above the x-axis. Mann-Whitney test. FIG. 6*e* shows current densities elicited by maximum displacement of control, MA (100 μM for 18 h)-treated N2A$^{Piezo1-/-}$ cells transfected with Piezo2-Piezo1 beam chimera, with and without Latrunculin A (1 μM for 1 h). Bars are mean±SD. n is denoted above the x-axis. Mann-Whitney test (for control vs. MA+LatA and MA vs. MA+LatA) and unpaired t-test (for control vs. MA). Asterisks indicate values significantly different from control (p<0.01 and *p<0.001) and n.s. indicates not significantly different from the control.

FIG. 7*a-f* shows MA decreases mechano-activated currents in MCC13 and mouse DRG neurons. FIG. 7*a* shows representative whole-cell patch-clamp recordings elicited by mechanical stimulation (at −60 mV) of rapidly (τ<10 ms), intermediate (10<t<30 ms), and slowly inactivating (τ>30 ms) currents of control (top) and MA (300 μM)-treated (bottom) MCC13, FIG. 7*b* shows current densities elicited by maximum displacement of control and MA (300 μM)-treated MCC13 cells. Bars are mean±SD. n is denoted above the x-axis. Unpaired t-test. FIG. 7*c* boxplots show the mean, median, and the 75th to the 25th percentiles of the displacement thresholds required to elicit mechano-currents of control and MA (300 μM)-treated MCC13 cells. n is denoted above the x-axis. Unpaired t-test with Welch's correction. FIG. 7*d* shows representative whole-cell patch-clamp recordings elicited by mechanical stimulation (at −60 mV) of rapidly (τ<10 ms), intermediate (10<t<30 ms), and slowly inactivating (τ>30 ms) currents of control (top) and MA (300 μM)-treated (bottom) DRG neurons. FIG. 7*e* shows current densities elicited by maximum displacement of control and MA (300 μM)-treated DRG neurons. Bars are mean±SD. n is denoted above the x-axis. Unpaired t-test, FIG. 7*f* boxplots show the mean, median, and the 75th to the 25th percentiles of the displacement thresholds required to elicit mechano-currents of control and MA (300 μM)-treated DRG neurons. n is denoted above the x-axis. Unpaired t-test with Welch's correction. Asterisks indicate values significantly different from control (*p<0.001, p<0.01 and *p<0.05) and n.s. indicates values not significantly different from the control.

FIG. 8*a* shows representative current-clamp recordings of membrane potential changes elicited by mechanical stimulation in control and MA (300 μM)-treated DRG neurons (up to 10 and 15 μm indentation, respectively). FIG. 8*b* shows membrane potential peak vs. mechanical indentation of independent control (n=10) and MA-treated (n=7) DRG neurons. Top panel shows boxplots displaying the mean, median, and the 75th to the 25th percentiles of the displacement threshold required to elicit an action potential in these neurons. Unpaired t-test. FIG. 8*c* shows representative current-clamp recordings of membrane potential changes elicited by a 1 Hz mechanical stimulus train of control and MA-treated DRG neurons. Inset illustrates the progressive decrease in membrane potential as the pulse number progresses. FIG. 8*d* shows left: number of action potentials elicited per sweep vs. mechanical indentation of control (n=6) and MA-treated (n=6) treated DRG neurons. Right: raster plots displaying the action potentials elicited by 12 μm of indentation. Bars indicate stimuli that elicited action potentials. Columns and rows represent cells and sweeps, respectively. Asterisks indicate values significantly different from control (***p<0.001).

FIG. 9*a-g* shows MA does not alter mouse DRG neurons electrical excitability. FIG. 9*a* shows representative whole-cell patch-clamp recordings of control and MA (300 μM)-treated DRG neurons depolarized in a stepwise manner from a holding potential of −80 mV. FIG. 9*b* shows normalized inward current densities elicited by stepwise depolarization from a holding potential of −80 mV of control (n=7) and MA (n=7; 300 μM)-treated DRG neurons. Circles are mean±SD. FIG. 9*c* shows normalized outward current densities elicited by stepwise depolarization from a holding potential of −80 mV of control (n=7) and MA (n 7; 300 μM)-treated DRG neurons. Circles are mean±SD. FIG. 9*d* shows membrane potential values recorded just after the whole-cell configuration was achieved from control and MA (300 μM)-treated DRG neurons. n is denoted above the x-axis. Mann-Whitney test. FIG. 9*e* shows representative current-clamp recording of membrane potential changes elicited by current injection in control and MA (300 μM)-treated DRG neurons. FIG. 9*f* shows action potential amplitudes evoked by current injection from control and MA (300 μM)-treated DRG neurons. n is denoted above the x-axis. Unpaired t-test with Welch's correction. FIG. 9*g* boxplot shows mean, median, and 75th to the 25th percentiles of the minimum current injected that elicited action potentials from control and MA (300 μM)-treated DRG neurons. n is denoted above the x-axis. Mann-Whitney test. n.s. indicates values not significantly different from the control.

FIG. 10*a-d* shows MA recovers normal mechanical response in sensitized mouse DRG neurons. FIG. 10*a* shows representative whole-cell patch-clamp traces of mechanically activated currents after perfusing bath solution (60 s) and bath solution containing bradykinin (BK; 1 μM) consecutively to control and MA (300 μM; 18 h)-treated DRG neurons. FIG. 10*b* shows current densities elicited by 10 μm displacement of control and MA (300 μM; 18 h)-treated DRG neurons perfused for with bath solution (60 s) and with bath solution containing bradykinin (BK; 300 s, 1 μM) consecutively. Bars are mean±SD. Data samples are paired. n is denoted above the x-axis. Paired t-test, unpaired t-test, Mann-Whitney, and Wilcoxon matched-pairs signed-ranks test. FIG. 10*c* shows representative whole-cell patch-clamp recordings elicited by mechanical stimulation (at −60 mV) of rapidly (τ<10 ms), intermediate (10<t<30 ms), and slowly inactivating (τ>30 ms) currents of control, BK (1 μM for 18 h) and BK+MA (1 μM and 300 μM respectively for 18 h)-treated DRG neurons. FIG. 10*d* shows current densities elicited by maximum displacement of mechanically activated currents elicited by mechanical stimulation (at −60 mV) of rapidly (τ<10 ins), intermediate (10<t<30 ms), and slowly inactivating (τ>30 ins) currents of control, BK (1 μM; 18 h) and BK+MA (1 μM and 300 μM respectively; 18 h both)-treated DRG neurons. Bars are mean±SD. Unpaired t-test. n is denoted above the x-axis. Asterisks indicate values significantly different from control (*p<0.001, p<0.01, and *p<0.05) and n.s. indicates not significantly different from the control.

FIG. 11 also shows MA recovers normal mechanical response in sensitized mouse DRG neurons. FIG. 11*a* shows current fold change of control and MA (300 μM; 18 h)-treated DRG neurons perfused for 60 s with bath solution and 300 s with bath solution containing Bradykinin (BK; 1 μM) consecutively. n is denoted bellow bars. Unpaired t-test. n.s. indicates not significantly different from the control.

FIG. 12*a* is a cartoon describing the repeated injury paradigm. Mice were tested for their baseline withdrawal thresholds to punctate mechanical (von Frey) and radiant heat (Hargreaves) stimulation. Afterward, one hind paw was injected daily for one week with a small volume of saline or saline containing MA (5 mM). After which, the mechanical and thermal withdrawal thresholds were measured again with or without the acute inflammation caused by application of mustard oil (AITC). FIG. 10*b* shows repeated injection of saline for 7 days causes hyper-reactivity to mechanical stimuli. Under baseline conditions (open circles) mice begin to withdraw their paws in the majority of trials (out of 10) when the force from von Frey filaments reaches between 0.2-0.4 g. By contrast, after repeated injury (closed circles) mice withdraw much more frequently to even very light filaments (0.02 g). Significant hyper-reactivity is seen for all filaments>0.02 g until maximum responses are evoked (10/10 responses to 0.6-1 g). These allodynic-like responses do not develop when mice are treated with MA (compare open and closed circles). p>0.01; n=6 mice per treatment group (n=3 males and 3 females). FIG. 12***c* shows repeated saline injection decreases the response latency (s) to radiant heat focused on the injured paw as well as the contralateral side. Inclusion of MA in the injection solution has no effect on this hyperresponsiveness to heat. n=6 mice per treatment group (n=3 males and 3 females). FIG. 12*d* shows acute topical administration of mustard oil (AITC) does not increase hyper-responsivity to punctate stimuli after one week of MA treatment (compare circles with squares). As a control, saline injected mice treated with AITC respond much more frequently to low force filaments (squares) n=6 mice per treatment group (n=3 males and 3 females).

FIG. 13*a-h* shows MA decreases mechano-activated currents in human iPSCs-derived neurons. FIG. 13*a* is a micrograph showing a human iPSCs derived neuron in the whole-cell patch-clamp configuration ready for mechanical stimulation. FIG. 13*b* shows representative whole-cell patch-clamp traces of mechanically activated currents of control and MA (300 and 600 μM for 18 h and 50 μM each day for 5 days)-treated iPSCs-derived neurons. FIG. 13*c* shows current densities elicited by maximum displacement of control and MA (300 and 600 μM for 18 h, and 50 μM each day for 5 days)-treated iPSCs-derived neurons. Bars are mean±SD. n is denoted above the x-axis. Unpaired t-test. FIG. 13*d* boxplots show mean, median, and the 75th to 25th percentiles of the displacement thresholds required to elicit currents of control and MA (300 and 600 μM for 18 h and 50 μM each day for 5 days)-treated iPSCs-derived neurons. n is denoted above the x-axis. Unpaired t-test. FIG. 13*e* shows the PIEZO2 time constant of inactivation elicited by maximum displacement of control and MA (300 and 600 μM for 18 h and 50 μM each day for 5 days)-treated iPSCs-derived neurons. Bars are mean±SD. n is denoted above the x-axis. Unpaired t-test. FIG. 13*f* shows representative whole-cell patch-clamp recordings of control and MA (300 μM)-treated iPSCs derived neurons depolarized in a step-wise manner from a membrane potential of −80 mV. FIG. 13*g* shows normalized inward current densities elicited by stepwise depolarization from −80 mV of control (n=8) and MA (n=8; 300 μM)-treated DRG neurons. Circles are mean±SD. FIG. 13*h* shows normalized outward current densities elicited by stepwise depolarization from −80 mV of control (n=8) and MA (n=8; 300 μM)-treated. DRG neurons. Circles are mean±SD. Asterisks indicate values significantly different from control (*p<0.001 and p<0.01) and n.s. indicates values not significantly different from the control.

FIG. 14*a-d* also shows MA decreases mechano-activated currents in human iPSCs-derived neurons. FIG. 14*a* shows representative whole-cell patch-clamp recordings elicited by mechanical stimulation (at −60 mV) of control and MA (300 μM)-supplemented N2A$^{Piezo1-/-}$ cells transfected with human Piezo2. FIG. 14*b* shows current densities elicited by maximum displacement of control and MA (300 μM; 18 h)-treated N2A$^{Piezo1-/-}$ cells transfected with human Piezo2. Bars are mean±SD. n is denoted above the x axis. Unpaired t-test. FIG. 14*c* boxplots show mean, median, and 75th to 25th percentiles of the displacement thresholds required to elicit currents of control and MA (300 μM; 18 h)-treated N2A$^{Piezo1-/-}$ cells transfected with human Piezo2. n is denoted above the x-axis. Unpaired t-test. FIG. 14*d* shows time constants of inactivation elicited by maximum displacement of control and MA (300 μM; 18 h)-treated N2A$^{Piezo1-/-}$ cells transfected with human Piezo2. Bars are mean±SD. n is denoted above the x-axis. Unpaired t-test. Asterisks indicate values significantly different from control (***p<0.001) and n.s. indicates not significantly different from the control.

FIGS. 15*a-g* further show MA decreases mechano-activated currents in rat DRG neurons. FIG. 15*a* is a micrograph showing a rat DRG neuron in the whole-cell patch-clamp configuration ready for mechanical stimulation. FIG. 15*b* shows representative whole-cell patch-clamp traces of mechanically activated currents of control and MA (300 μM for 18 h)-treated rat DRG neurons. FIG. 15*c* shows current densities elicited by maximum displacement of control and MA (300 for 18 h)-treated rat DRG neurons. Bars are mean±SD. n is denoted above the x-axis. Unpaired t-test. FIG. 15*d* boxplots show mean, median, and the 75$^{th}$ to 25$^{th}$ percentiles of the displacement thresholds required to elicit currents of control and MA (300 μM for 18 h)-treated rat DRG neurons. n is denoted above the x-axis. Unpaired t-test. FIG. 15*e* shows representative current-clamp recordings of membrane potential changes elicited by mechanical stimulation in control and MA (300 μM)-treated rat DRG neurons (up to 9 and 13 μm indentation, respectively). FIG. 15*f* shows membrane potential peak vs. mechanical indentation of independent control (n=11) and MA-treated (n=7) DRG neurons. Top panel shows boxplots displaying the mean, median, and the 75$^{th}$ to the 25$^{th}$ percentiles of the displacement threshold required to elicit an action potential in these neurons. Mann-Whitney test. FIG. 15*g* shows membrane resting potential values recorded briefly after whole-cell current clamp configuration was achieved from control and MA (300 μM)-treated rat DRG neurons. n is denoted above the x-axis. Mann-Whitney test. Asterisks indicate values significantly different from control (**p<0.01) and n.s. indicates not significantly different from the control.

FIGS. 16*a-g* further show MA decreases mechano-activated currents in rat DRG neurons. FIG. 16*a* shows the current-voltage relationship of rat DRG neuron mechano currents as determined by whole-cell patch-clamp experiments. Circles are mean±SD. n=3. FIG. 16*b* shows the time constant of inactivation of currents elicited by maximum displacement of control and MA (300 μM for 18 h)-treated rat DRG neurons. Bars are mean±SD. n is denoted above the x-axis. Unpaired t-test. FIG. 16*c* shows representative current-clamp recordings of membrane potential changes elicited by a train of mechanical pulses of control and MA-treated rat DRG neurons. FIG. 16*d* shows the number of action potentials elicited per sweep vs. mechanical indentation of control (n=6) and MA-treated (n=6) treated rat DRG neurons. FIG. 16*e* shows the action potential amplitude measured from resting potential to peak membrane potential of control and MA (300 μM for 18 h,)-treated rat DRG neurons. Bars are mean±SD. n is denoted above the x-axis. Unpaired t-test. FIG. 16*f* shows the normalized outward current densities elicited by stepwise depolarization from a holding potential of −80 mV of control (n=8) and MA (n=6; 300 μM)-treated rat DRG neurons. Circles are mean±SD. FIG. 16*g* shows the normalized inward current densities elicited by stepwise depolarization from a holding potential of −80 mV of control (n=8) and MA (n=6; 300 μM)-treated DRG neurons. Circles are mean±SD. Asterisks indicate values significantly different from control (**p<0.01) and n.s. indicates not significantly different from the control.

FIGS. 17*a-d* show an omega-3 enriched diet decreases the time constants of inactivation of PIEZO2 in mouse DRG neurons. FIG. 17*a* shows representative PIEZO2 currents elicited by mechanically stimulating (at −60 mV) DRG neurons dissected from WT mice fed with control or w-3 enriched diet. FIG. 17*b* shows the PIEZO2 time constant of inactivation elicited by maximum displacement of DRG neurons dissected from WT mice fed with control or omega-3 enriched diet. Bars are mean±SD. n is denoted above the x-axis. Unpaired t-test. FIG. 17*c* shows current densities elicited by maximum displacement of DRG neurons dissected from control and omega-3 enriched diet. Bars are mean±SD. n is denoted above the x-axis. Unpaired t-test. FIG. 17*d* boxplots show the mean, median, and the 75th to the 25th percentiles of the displacement thresholds required to elicit mechano-currents of DRG neurons dissected from control and omega-3 enriched diet. n is denoted above the x-axis. Unpaired t-test with Welch's correction. Asterisks indicate values significantly, different from control (*p<0.05) and n.s. indicates values not significantly different from the control.

FIG. 18*a* shows representative whole-cell patch-clamp traces of mechanically activated currents of control and EPA (200 μM for 18 h)-treated rat DRG neurons. FIG. 18*b* shows the PIEZO2 time constant of inactivation elicited by maximum displacement of control and EPA (200 μM for 18 h)-treated rat DRG neurons. Bars are mean±SD. n is denoted above the x-axis. Unpaired t-test. FIG. 18*c* shows current densities elicited by maximum displacement of control and EPA (200 μM for 18 h)-treated rat DRG neurons. Bars are mean±SD. n is denoted above the x-axis. Unpaired t-test. FIG. 18*d* boxplots show the mean, median, and the 75th to the 25th percentiles of the displacement thresholds required to elicit mechano—of control and EPA (200 μM for 18 h)-treated rat DRG neurons. n is denoted above the x-axis. Unpaired t-test with Welch's correction. Asterisks indicate values significantly different from control (**p<0.01) and n.s. indicates values not significantly different from the control.

FIGS. 19*a-c* show EPA supplementation abrogates the phenotype of PIEZO2 arthrogryposis mutations. FIG. 19*a* shows ribbon representation of the mouse PIEZO2 monomer highlighting mutations causing arthrogryposis in humans. FIG. 19*b* shows representative normalized macroscopic currents (at −60 mV) evoked by maximum displacement of N2A cells transfected with PIEZO2 arthrogryposis mutants S2691R and E2727del with and without EPA supplementation (left and right, respectively). FIG. 19*c* shows the PIEZO2 time constants of inactivation elicited by maximum displacement of arthrogryposis mutants S2691R and E2727del with and without EPA supplementation. Bars are mean±SD. Unpaired t-test with Welch correction. Asterisks indicate values significantly different from control (p<0.01 and *p<0.001) and n.s. indicates not significantly different from the control.

FIG. 20*a*-1 show EPA supplementation decreases the time constants of inactivation of heterologously-expressed mouse PIEZO2 currents in N2A$^{Piezo1-/-}$ cells. FIG. 20*a* shows representative whole-cell patch-clamp recordings of control and EPA (200 μM; 18 h)-treated N2A$^{Piezo1-/-}$ cells transfected with PIEZO V2. FIG. 20*b* shows time constants of inactivation elicited by maximum displacement of control and EPA (200 μM; 18 h)-treated N2A$^{Piezo1-/-}$ cells transfected with PIEZO V2. Bars are mean±SD. n is denoted above the x-axis. Unpaired t-test. FIG. 20*c* boxplots show mean, median, and 75th to 25th percentiles of the displacement thresholds required to elicit currents of control and EPA (200 μM; 18 h)-treated N2A$^{Piezo1-/-}$ cells transfected with PIEZO V2. n is denoted above the x-axis. Unpaired t-test. FIG. 20*d* shows current densities elicited by maximum displacement of control and EPA (200 μM; 18 h)-treated N2A$^{Piezo1-/-}$ cells transfected with PIEZO V2. Bars are mean±SD. n is denoted above the x-axis. Mann-Whitney test. FIG. 20*e* shows representative whole-cell patch-clamp recordings of control and EPA (200 μM; 18 h)-treated N2A$^{Piezo1-/-}$ cells transfected with PIEZO V16. FIG. 20*f* shows time constants of inactivation elicited by maximum displacement of control and EPA (200 μM; 18 h)-treated N2A$^{Piezo1-/-}$ cells transfected with PIEZO V16. Bars are mean±SD. n is denoted above the x-axis. Unpaired t-test. FIG. 20*g* boxplots show mean, median, and 75th to 25th percentiles of the displacement thresholds required to elicit currents of control and EPA (200 μM; 18 h)-treated N2A$^{Piezo1-/-}$ cells transfected with PIEZO V16. n is denoted above the x-axis. Unpaired t-test. FIG. 20*h* shows current densities elicited by maximum displacement of control and EPA (200 μM; 18 h)-treated N2A$^{Piezo1-/-}$ cells transfected with PIEZO V16. Bars are mean±SD. n is denoted above the x-axis. Mann-Whitney test. FIG. 20*i* shows representative whole-cell patch-clamp recordings of control and EPA (200 μM; 18 h)-treated N2A$^{Piezo1-/-}$ cells transfected with PIEZO V14. FIG. 20*j* shows time constants of inactivation elicited by maximum displacement of control and EPA (200 μM; 18 h)-treated N2A$^{Piezo1-/-}$ cells transfected with PIEZO V14. Bars are mean±SD. n is denoted above the x-axis. Unpaired t-test. FIG. 20*k* boxplots show mean, median, and 75th to 25th percentiles of the displacement thresholds required to elicit currents of control and EPA (200 μM; 18 h)-treated N2A$^{Piezo1-/-}$ cells transfected with PIEZO V14. n is denoted above the x-axis. Unpaired t-test. FIG. 20*l* Current densities elicited by maximum displacement of control and EPA (200 μM; 18 h)-treated N2A$^{Piezo1-/-}$ cells transfected with PIEZO V14. Bars are mean±SD. n is denoted above the x-axis. Mann-Whitney test. Asterisks indicate values significantly different from control (***p<0.001) and n.s. indicates not significantly different from the control.

FIGS. 21*a-d* show that a combination of margaric and eicosapentaenoic acids (MA and EPA, respectively) decreases PIEZO2 currents and enhances inactivation in cultured mouse DRG neurons. FIG. 21*a* shows representative whole-cell patch-clamp recordings elicited by mechanical stimulation (at −60 mV) of PIEZO2 currents of control (left) and MA (300 μM)+EPA (200 μM)-treated (right) DRG neurons. FIG. 21*b* shows PIEZO2 current densities elicited by maximum displacement of control and MA (300 μM)+EPA (200 μM)-treated DRG neurons. Bars are mean±SD. FIG. 21*c* shows displacement thresholds required to elicit PIEZO2 currents of control and MA (300 μM)+EPA (200 μM)-treated DRG neurons. Boxplots show mean (square), median (bisecting line), bounds of box (75th to 25th percentiles), outlier range with 1.5 coefficient (whiskers), and minimum and maximum data points. FIG. 21*d* shows PIEZO2 time constants of inactivation elicited by maximum displacement of control and MA (300 μM)+EPA (200 μM)-treated DRG neurons. Bars are mean±SD. n is denoted above the x-axis. p-values are denoted above the bars and boxes.

Figures 1A, 1B, 1C:
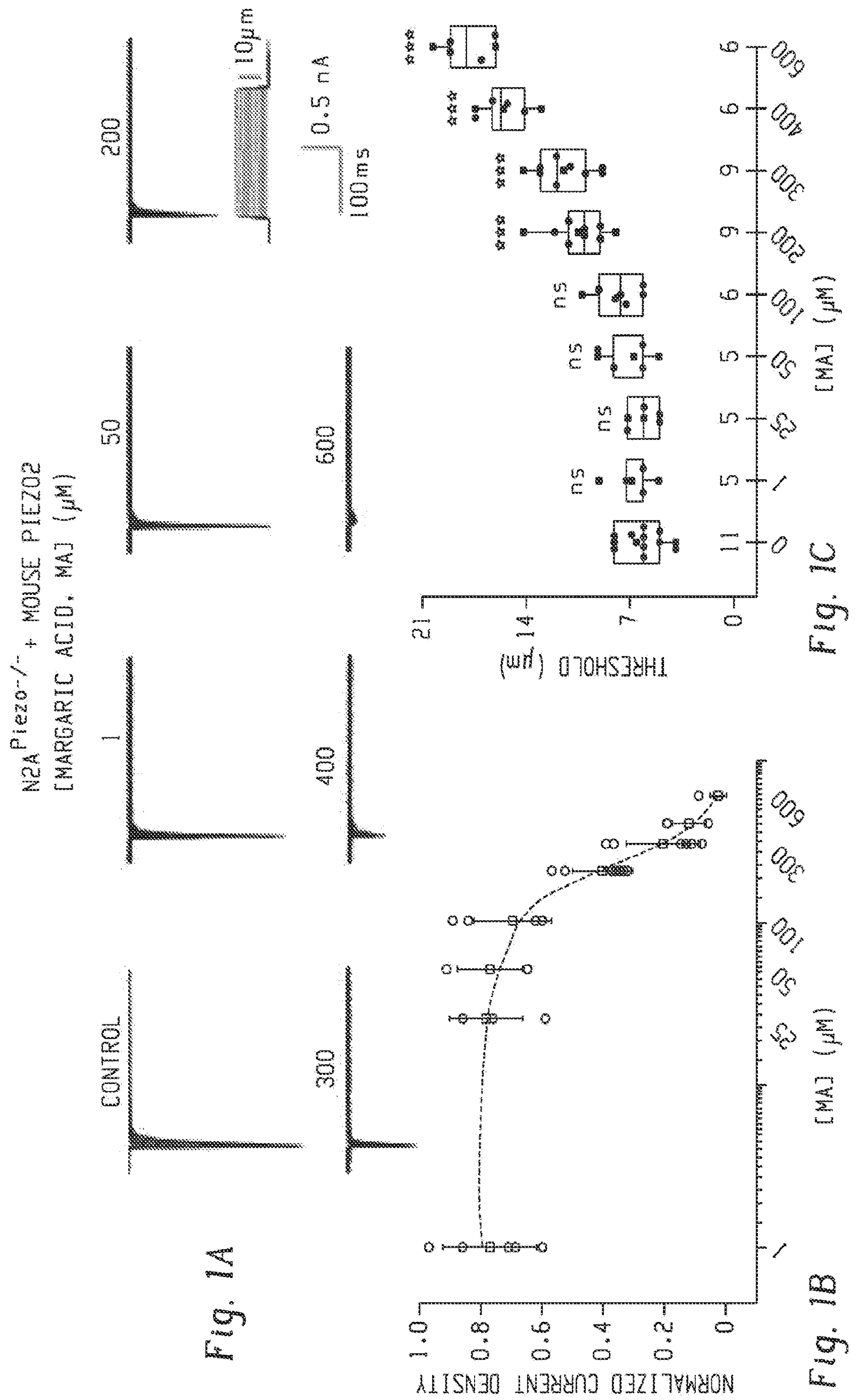

The above-described and other features will be appreciated and understood by those skilled in the art from the following detailed description, drawings, and appended claims.

DETAILED DESCRIPTION

The inventors previously explored how fatty acids influence mechanotransduction. When enriched in the plasma membrane, the esterified saturated fatty acid margaric acid (MA; heptadecanoic acid; C17:0) inhibits PIEZO1 channels by increasing the structural order and stiffness of the membrane, thereby increasing the mechanical threshold required to activate the channel. Given the overall similarity of PIEZO2 to PIEZO1, the inventors reasoned that MA might also decrease PIEZO2 function and thus have therapeutic potential. However, unlike PIEZO1 that can be activated by changes in membrane tension alone, PIEZO2 requires an intact cytoskeleton for normal function, as so far it can only be gated in cell-attached or whole-cell patch camp configurations. Therefore, whether MA can efficiently modulate and decrease PIEZO2 activity remained to be determined.

As shown herein, the inventors used electrophysiology and behavioral approaches to determine that MA decreases PIEZO2 function under normal and inflammatory conditions. The inventors found that MA potently decreases PIEZO2 currents in a wide range of cell-types from mice and rats to humans, by increasing the mechanical stimuli needed to activate the channel. Notably, MA supplementation combined with latrunculin A treatment (i.e., a toxin that disrupts actin polymerization), revealed that PIEZO2 mechanosensitivity relies on both the plasma membrane and the cytoskeleton elements. Results from a PIEZO2-PIEZO1 chimera show that the PIEZO2 beam, a large intracellular domain that runs parallel to the membrane and is thought to be critical for force sensing, dampens the effect of the membrane on Piezo2 gating. Importantly, the inventors determined that in dorsal root ganglia (DRG) neurons, MA efficiently reduces the action potential firing elicited by mechanical stimuli but not by current injection, suggesting that MA might blunt touch responses in vivo. Furthermore, MA decreases PIEZO2 currents potentiated by the proalgesic agent bradykinin, indicating that it might be particularly useful for reducing heightened touch responses during inflammation. The inventors found that MA selectively decreased the heightened touch responses seen during a repeated injury murine model without affecting thermal responses.

In an aspect, a method of treating pain comprises administering to a subject in need of treatment for pain a pharmaceutical composition comprising a therapeutically effective amount of margaric acid.

Exemplary types of pain to be treated include inflammatory pain, pain due to nerve injury, neuropathic pain, chronic pain, intractable cancer pain, complex regional pain syndrome, surgical or post-surgical pain, dental pain, pain resulting from dermal injury, lower back pain, headaches, migraine, allodynia, and hyperalgesia. In certain aspects, the pain is chronic. In other aspects, the pain is acute. The pain may be mild or severe.

Exemplary pain indications include treatment or prophylaxis of surgical or post-surgical pain for various surgical procedures including amputation, post-cardiac surgery, dental pain/dental extraction, pain resulting from cancer, muscular pain, mastalgia, pain resulting from dermal injuries, lower back pain, headaches of various etiologies, including migraine, menstrual cramps, tactile allodynia and hyperalgesia. The pain may be somatogenic (either nociceptive or neuropathic), acute and/or chronic. Peripheral neuropathies which can be treated with margaric acid include mono-neuropathies, mono-multiplex neuropathies, and poly-neuropathies, including axonal and demyelinating neuropathies. Both sensory and motor neuropathies are encompassed. The neuropathy or neuropathic pain may be associated with a number of peripheral neuropathies of varying etiologies, including but not limited to: trauma-induced neuropathies, including those caused by physical injury (such as blunt trauma, abrasion, or burns) or disease state, physical damage to the brain, physical damage to the spinal cord, or stroke associated with brain damage; neurological disorders related to neurodegeneration; and post-surgical neuropathies and neuropathic pain (such as from shingles, diabetes and the like) infectious and viral neuropathies, including those caused by leprosy, Lyme disease, a herpes virus (and more particularly by a herpes zoster virus, which may lead to post-herpetic neuralgia), human immunodeficiency virus (HIV, which may lead to HIV neuropathy), or a papilloma virus, or any other pathogen-induced nerve damage; toxin-induced neuropathies (including but not limited to neuropathies induced by alcoholism, vitamin B6 intoxication, hexacarbon intoxication, amiodarone, chloramphenicol, disulfuram, isoniazide, gold, lithium, metronidazole, misonidazole, nitrofurantoin); drug-induced neuropathies, including therapeutic-drug-induced neuropathy, particularly a) chemotherapy-induced neuropathies caused by anti-cancer agents such as taxol, taxotere, cisplatin, nocodazole, vincristine, vindesine and vinblastine, and b) anti-viral neuropathies caused by anti-viral agents such as ddI, DDC, d4T, foscarnet, dapsone, metronidazole, and isoniazid); vitamin-deficiency-induced neuropathies including those resulting from vitamin B12 deficiency, vitamin B6 deficiency, and vitamin E deficiency); hereditary neuropathy (including but not limited to Friedreich ataxia, familial amyloid polyneuropathy, Tangier disease, Fabry disease; diabetic neuropathy and neuropathy caused by metabolic disorders such as renal insufficiency and hypothyroidism; neuropathy secondary to tumor infiltration, auto-immune neuropathies, including those resulting from Guillain-Barre syndrome, chronic inflammatory demyelinating polyneuropathy, monoclonal gammopathy of undetermined significance and polyneuropathy, and multiple sclerosis; other neuropathies and neuropathic pain syndromes including inflammation-induced nerve damage, neurodegeneration, post-traumatic neuralgia, central neuropathic pain syndromes such as phantom limb pain, pain, complex regional pain syndromes (including but not limited to reflex sympathetic dystrophy, causalgia), neoplasia-associated pain, vasculitic/angiopathic neuropathy, and sciatica; and idiopathic neuropathies.

Neuropathic pain may be manifested as allodynia, hyperalgesic pain, or phantom pain. In another embodiment, neuropathy may instead lead to loss of pain sensitivity.

There are three types allodynia. Tactile (also called static) allodynia is pain caused by touch, such as clothing lying against the skin or a person lightly touching on the arm. Mechanical (also called dynamic) allodynia is pain caused by movement across the skin such as drying off with a towel, or the brushing of bedsheets across the skin. Thermal allodynia is pain caused by heat or cold that does not cause damage to the tissues. Patients with allodynia experience pain in response to stimuli generally considered to be harmless.

Fibromyalgia is a disease which has a systemic unbearable chronic pain as the core symptom accompanied by various comorbid symptoms such as sleeplessness, systemic fatigue feeling, depressive symptom and the like. Fibromyalgia is often accompanied by tactile allodynia. Fibromyalgia can also be accompanied by mechanical allodynia and thermal allodynia.

Additional medical conditions associated with allodynia include chronic inflammation, migraines, trigeminal neuralgia, postherpetic neuralgia, peripheral neuropathy, diabetic neuropathic pain, chronic fatigue syndrome, complex regional pain syndrome, and the like.

Inflammatory pain includes inflammatory joint pain, inflammatory musculoskeletal pain, pain due to injury, arthritis pain, and complex regional pain syndrome.

The agent may be administered via a route normally used to administer a medicament for the treatment of pain including, but not limited to, oral, parenteral (including subcutaneous, intradermal, intramuscular, intravenous, intraarticular, and intramedullary), transmucosal (including nasal), transdermal, and topical (including dermal, buccal, sublingual and intraocular) routes. Intravenous delivery, for example, may take place via a bolus injection or via infusion; infusion may be done over a period ranging from less than a minute to several hours to continuously. In certain embodiments, a course of treatment will involve administration by a combination of routes.

The pharmaceutical compositions may include various pharmaceutically acceptable additives including, but not limited to, carriers, excipients, binders, stabilizers, antimicrobial agents, antioxidants, diluents and/or supports.

As used herein, topical administration means non-systemic administration. This includes the application of a compound disclosed herein externally to the epidermis or the instillation of such a compound into the ear, eye or nose, such that the compound does not significantly enter the blood stream. In contrast, systemic administration refers to oral, intravenous, intraperitoneal and intramuscular administration.

In an aspect, the topical or transdermal dosage of margaric acid provides 0.1 to 20 mg/kg of margaric acid.

Formulations for transdermal administration include liquid or semi-liquid preparations suitable for penetration through the skin to the site of pain such as liquids, gels, lotions, creams, ointments or pastes. Formulations for transdermal administration may include excipients for solubilizing margaric acid. Drops suitable for administration to the eye, ear or nose may also be employed as topical formulations. Margaric acid for transdermal or topical administration may comprise, for example, from 0.01% to 10% w/w (by weight), 0.2-10 wt %, or 0.5-25 wt % of the formulation.

Topical patches are topical formulations that are configured to locally or transdermally deliver an active agent to a subject when topically applied to a skin surface of a subject. The formulations may include two or more layers, where the two or more layers may include at least an adhesive matrix and a backing.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion.

Pharmaceutical preparations which can be used orally include tablets and capsules such as capsules made of gelatin and soft capsules as are known in the art. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent.

Formulations for injection may be presented in unit dosage form, e.g., in ampoules or in multi-dose containers, with an added preservative. The compositions may take such forms as suspensions, solutions or emulsions in oily or aqueous vehicles, and may contain excipients such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use.

In addition to the formulations described previously, the compounds may also be formulated as a depot preparation. Such long acting formulations may be administered by implantation (for example subcutaneously or intramuscularly) or by intramuscular injection.

In an aspect, a transdermal pharmaceutical composition comprises margaric acid and a pharmaceutically acceptable excipient.

In another aspect, a composition for the treatment of pain comprises margaric acid, eicosapentaenoic acid, and a pharmaceutically acceptable excipient. Eicosapentanoic acid (EPA; 20:5) is a dietary long-chain omega-3 fatty acid thought to be involved in reducing inflammation. When combined with MA, EPA is expected to further reduce tactile inflammatory and tactile pain.

In an aspect, a topical formulation comprises 0.49 to 0.55 of wt % of margaric acid, 0.49 to 0.55 wt % of eicosapentaenoic acid, 25.05 to 27.69 wt % of a main solvent, 23.77 to 26.27 of a co-solvent, and 45.19 to 49.95 wt % of a viscosity agent, all weights based on the total weight of the topical formulation. In a further aspect the main solvent is sesame oil, the co-solvent is paraffin oil, and the viscosity agent is castor oil.

The invention is further illustrated by the following non-limiting examples.

EXAMPLES

Methods

Cell culture and electrophysiology: Piezo1 knock-out mouse N2A (N2A$^{Piezo1-/-}$) cells were a gift from Dr. Gary R. Lewin, human Merkel cell carcinoma cell line (MCC13 cells; Cell Bank Australia reference number: CBA1338) were obtained from Sigma, and DRG neurons were obtained from sacrificed mice. N2A$^{Piezo1-/-}$ cells were cultured in Dulbecco's Modified Eagle Medium (DMEM), 5% penicillin streptomycin and 10% fetal bovine serum (FBS); MCC13 cells were cultured in RPMI 1640 (with 2 mM L-glutamine+25 mM HEPES; Sigma), 5% penicillin-streptomycin and 10% FBS and; DRG neurons were cultured in DMEM, 1% penicillin-streptomycin, 1% MEM vitamin solution, 1% L-glutamine, and 10% horse serum. Prior to electrophysiological measurements, N2A$^{Piezo1-/-}$, MCC13 and DRG neurons were supplemented overnight (≈18 h) with MA. For accumulation assays, cells were supplemented with 50 μM MA every 24 h for 5 days. MA was obtained from Nu-Chek Prep, INC. The cultured cells were maintained at 37° C., 95% relative humidity, and 5% $CO_2$. Rat DRG neurons (R8820N-10) were obtained from Cell Applications, INC. Neurons were thawed and cultured according to the manufacturer's protocol and used between day 3-5 after thawing.

For whole-cell recordings, the bath solution contained 140 mM NaCl, 6 mM KCl, 2 mM $CaCl_2$), 1 mM $MgCl_2$, 10 mM glucose, and 10 mM HEPES (pH 7.4; 300 mOsm). The pipette solution for voltage-clamp recordings contained: 140 mM CsCl, 5 mM EGTA, 1 mM $CaCl_2$), 1 mM $MgCl_2$, and 10 mM HEPES (pH 7.2); and for current clamp recordings: 140 mM KCl, 6 mM NaCl, 2 mM $CaCl_2$), 1 mM $MgCl_2$, 10 mM glucose, and 10 mM HEPES (pH 7.4; 300 mOsm); MA and bradykinin acetate salt (Sigma) perfused during experiments were dissolved in the bath solution to a final concentration of 300 μM for 2 min, and 1 μM for 5 min respectively; and for long exposure experiments bradykinin was supplemented to the culture medium and added to the cells 18-24 h prior recording. For cytoskeleton disruption experiments, N2A$^{Piezo1-/-}$ were incubated in media supplemented with 1 μM latrunculin A (Cayman Chemicals) for 1 h prior recordings. Pipettes were made out of borosilicate glass (Sutter Instruments) and were fire-polished before use until a resistance between 3 and 5 MΩ was reached.

During mechanical stimulation, currents were recorded at a constant voltage (−60 mV, voltage-clamp), and voltages were recorded without injecting current (current-clamp). Both variables were sampled at 100 kHz and low-pass filtered at 10 kHz using a MultiClamp™ 700 B amplifier and Clampex (Molecular Devices, LLC). To measure voltage-dependent currents, a square-pulse protocol consisting of 40-ms 20-mV incremental steps starting from −80 mV in 500-ms intervals with P/4 subtraction was used; and to record action potentials evoked by current injection, 40-ms 20-pA incremental steps were injected in 500-ms intervals. In both cases, variables were sampled at 20 kHz and low-pass filtered at 10 kHz. Leak currents before mechanical stimulations were subtracted off-line from the current traces and data were digitally filtered at 2 kHz with ClampFit (Molecular Devices, LLC). Recordings with leak currents>200 pA, with access resistance>10 MΩ, and cells which giga-seals did not withstand at least 6 consecutive steps of mechanical stimulation were excluded from analyses.

Mechanical stimulation: For indentation assays, N2A$^{Piezo1-/-}$, MCC13 DRG neurons, and human iPSC374 derived neurons were mechanically stimulated with a heat-polished blunt glass pipette (3-4 μm) driven by a piezo servo controller (E625, Physik Instrumente). The blunt pipette was mounted on a micromanipulator at an ~45° angle and positioned 3-4 μm above from the cells without indenting them. Displacement measurements were obtained with a square-pulse protocol consisting of 1 μm incremental indentation steps, each lasting 200 ms with a 2-ms ramp in 10-s intervals. The threshold of mechano-activated currents for each experiment was defined as the indentation step that evoked the first current deflection from the baseline. For current clamp experiments, the mechanical threshold was defined as the indentation step that evoked the first action potential.

For pulse train assays, 13 s sweeps with a train rate of 1 Hz of square-pulses lasting 200 ms were used. Subsequent sweeps had increments of 1 μm. Only cells that did not detach throughout stimulation protocols were included in the analysis. The piezo servo controller was automated using a MultiClamp™ 700 B amplifier through Clampex (Molecular Devices, LLC).

N2APiezo1−/− cells transfection: N2APiezo1−/− cells were co-transfected with 75-200 ng·ml$_{-1}$ of mmPiezo2 variants (2, 14 and 16), or 1 ng·ml$_{-1}$ the PIEZO2-PIEZO1 beam chimera cloned in pcDNA3.1 and GFP391 pMO; using Lipofectamine® 2000 (Thermo Fisher Scientific) according to the manufacturer's instructions and recorded 48 h later. Fatty acids were supplemented 18-24 h prior recording, unless stated otherwise.

Primary culture of DRG neurons: Primary cultures of DRG neurons were obtained from 8-12 weeks old male C57BL/6 mice. Mice were anesthetized with isoflurane and then sacrificed by cervical dislocation. DRGs were dissected and kept on ice in Hank's balanced salt solution 1× (HBSS without $CaCl_2$) and $MgCl_2$). Then, DRGs were incubated in 1 mg/mL collagenase B (Sigma) in HBSS, at 37° C. and 5% $CO_2$, and after 1 hour were dissociated in medium without serum. The cell suspension solution was centrifuged 8 min at 800 rpm. The obtained pellet was resuspended in DMEM complete media containing 1% penicillin-streptomycin, 1% 402 MEM vitamin solution, 1% L glutamine, and 10% horse serum. Cells were cultured on coverslips pre-treated with poly-L lysine. All cultured neurons were used after 18-24 h.

Mice behavior: MA solution: MA was prepared in sterile Dulbecco's phosphate buffered saline, with 70 g/L fatty acid free bovine serum albumin (BSA; Sigma), and MA to a final concentration of 5 mM. The solution was filtered to avoid undissolved materials.

Subjects: For the experiment 8-12 weeks old male and female C57B16/J mice (N=12; control n=6; male=3, female=3) MA (n=6; male=3, female=3) per experiment were used. Mice were housed under a 12 hr light dark cycle and granted access to food and water ad libitum.

Treatment: Animals were put in two groups (control and MA) and given injections in the plantar of the left hind paw for 7 days prior behavioral assessment. Injections were given as follows: Mouse is restrained by their tail, foot, and over shoulders scruff. The compound is delivered using a 3/10 cc insulin syringe into the plantar surface of the back foot of each mouse. The beveled needle is inserted at a 35-40° angle and 20-50 μl of the compound is injected subcutaneously. The needle is held in place for several seconds before being removed and the animal is returned to its home cage. All female animals were handled and treated before the males to reduce stress.

Prior to all behavioral assays animals were habituated to the testing apparatus for a period of ~30 min. To induce acute inflammation, AITC (1 mM) was applied to the paw using a small paint brush.

Mechanical threshold (Von Frey test): Punctate mechanical allodynia was measured using Von Frey monofilaments (Stoelting, Inc.) in varying grams of force (0.008-1 g). Animals were placed in small enclosures over a wire mesh and the plantar of the hind paw was poked with a filament and responses were recorded. Withdrawal responses were recorded when mesh and the plantar of the hind paw was poked with a filament and responses were recorded. Withdrawal responses were recorded when the animal lifted, shook, or licked the paw in response to stimulus presentation. If the animal made no movement in a response to stimulus presentation, no response was indicated. Each filament is pressed into the plantar until the fiber bends slightly the amount of force needed to bend the fiber is dependent on the thickness of each monofilament. A response is indicated by five withdrawal responses to a filament, the test stops for each subject when the withdrawal to any particular filament is ten.

Mechanical pain (Pinprick): Animals were placed in small enclosures over a wire mesh and the plantar of the hind paw was poked with a needle (25 G 5/8") at a 45° angle. Responses were recorded, stimulus presentations occurred ten times per hind paw.

Thermal threshold (Hargreaves test): Animals were placed in small enclosures over a glass plate heated to 32° C. (IITC). A focused radiant heat light source is applied to the plantar of the hind paw. The latency for each rodent to withdraw the paw is recorded with three stimulus presentations administered per paw. Mouse is restrained by their tail, foot, and over shoulders scruff. The compound is delivered using a 3/10 cc insulin syringe into the plantar surface of the back foot of each mouse. The beveled needle is inserted at a 35-40° angle and 20-50 μl of the compound is injected subcutaneously. The needle is held in place for several seconds before being removed and the animal is returned to its home cage. All female animals were handled and treated before the males to reduce stress.

Human iPSC-derived neurons: For generating human peripheral sensory neuron cultures, a version of the healthy control WTC11 iPSC line was used. This line was previously engineered to harbor a doxycycline-inducible NGN2-BRN3A construct that enables rapid and efficient sensory neuron differentiation. Undifferentiated iPSCs were maintained in E8 flex medium (invitrogen) on polystyrene plates coated with Matrigel® (Corning). The medium was exchanged every 1-3 days, and the cells were passaged every 4-7 days with Accutase® (Invitrogen) and plated overnight with 10 μM of the ROCK-inhibitor Y-27632 (Tocris). For sensory neuron differentiation, iPSCs were seeded at 20,000 cells·$(cm_2)_{-1}$ in neural differentiation medium (NDM) on Matrigel®-coated plates. The cells were then re-plated after 48 hours at 50,000 cells·$(cm^2)^{-1}$ onto dishes coated with polyethylenimine (Sigma-Aldrich) and laminin (Invitrogen). NDM consisted of (all from Invitrogen) 1:1 DMEM/F12 and Neurobasal™ medium supplemented with N2, B27, and GlutaMAX™ at manufacturer-recommended dilution. 2 μg·$ml^{-1}$ doxycycline (Clontech) was included in the medium for the duration of the culture, 10 μM. Y-27632 was supplemented for the first 48 hours, and the following neurotrophic factors were added from day 8 onward at 10 ng/ml each (all from R&D systems): BDNF, GDNF, β-NGF, and NT-3. Full medium changes were made every other day until after day 8, and then half volume medium changes were done every other day for the remaining time in culture. Before electrophysiological recording, a subset of dishes was supplemented with 300 or 600 μM for 18 hours or 50 μM for 5 days of MA. All recordings were performed on neurons cultured for 14-16 days.

Data analysis: Results were expressed as means±SD (unless otherwise noted). Box plots depict a range between the $25_{th}$ and $75_{th}$ percentiles, mean, median, and outliers with a 1.5 coefficient. Data were plotted using OriginPro (from OriginLab). The time constant of inactivation T was obtained by fitting a single exponential function (1) between the peak value of the current and the end of the stimulus:

$$f_{(t)} = \sum_{i=1}^{n} A_i * e^{-t/\tau_i} + C, \quad (1)$$

where A=amplitude; τ=time constant; and the constant y-offset C for each component i. Sigmoidal fitting was done using OriginPro with the following Boltzmann function:

$$f_{(x)} = A_2 + \frac{A_1 - A_2}{1 + e^{(X - X_0)/dX)}}, \quad (2)$$

where $A_2$=final value; $A_1$=initial value; $X_o$=center; and dX=time constant. Statistical analyses were performed using GraphPad Instat 3 software. Individual tests are described on each of the figure legends.

Example 1: Margaric Acid Inhibits PIEZO2 Currents in N2A Cells

Figures 2A, 2B, 2C, 2D:
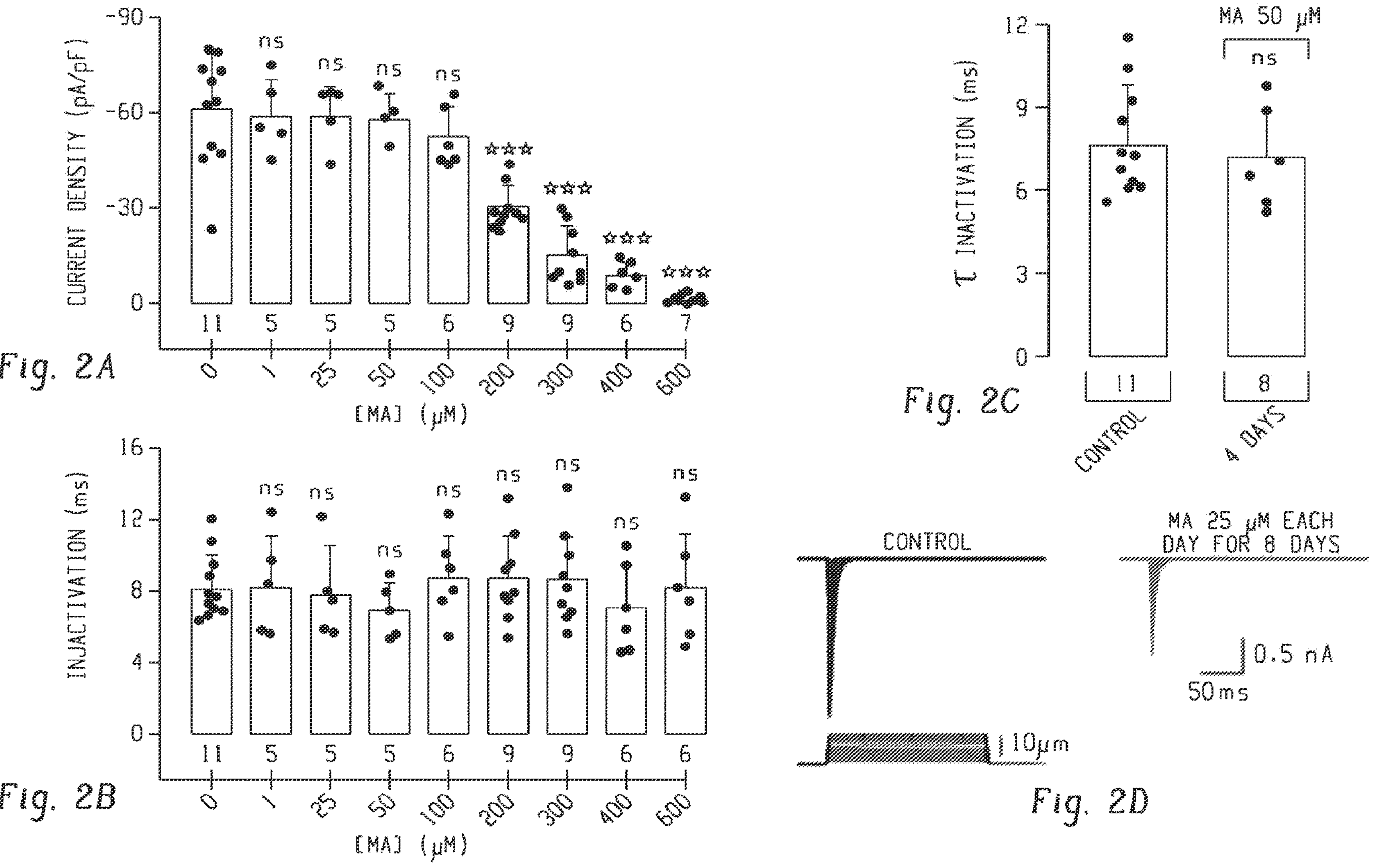
FIG. 2*a-g* support that MA inhibits heterologously-expressed mouse PIEZO2 currents in N2A$^{Piezo1-/-}$ cells.
Figure 2G:
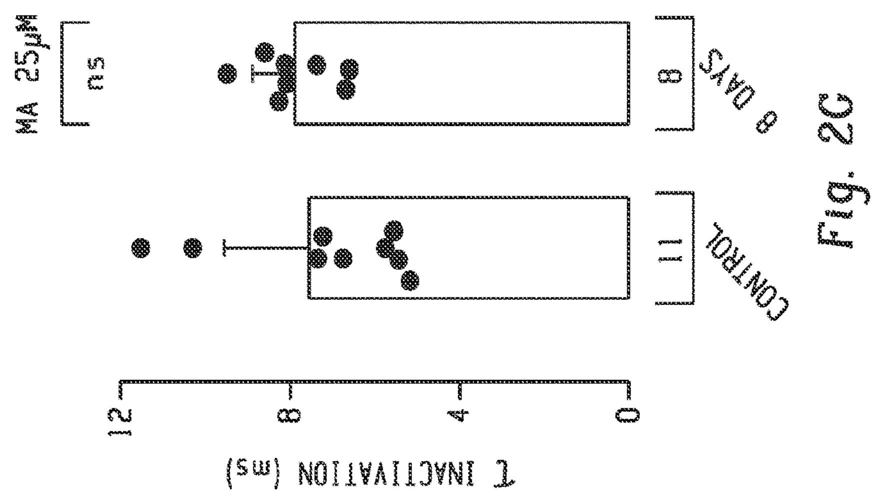
Figure 2F:
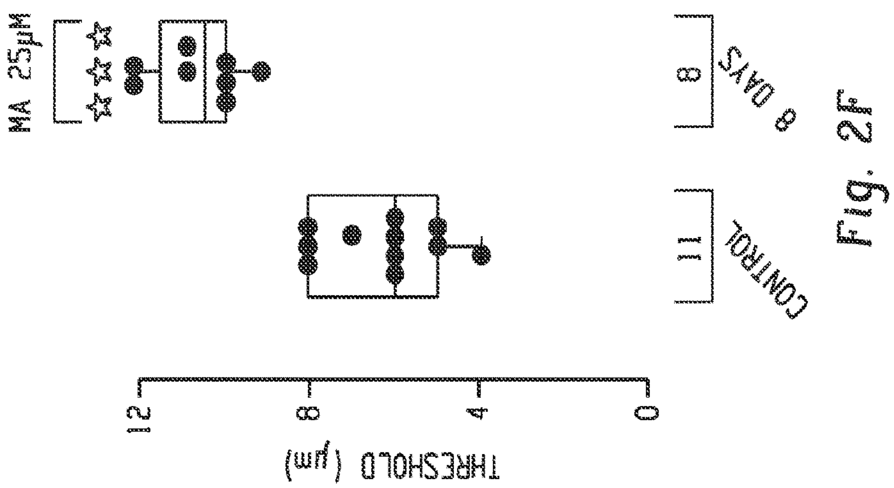
Figure 2E:
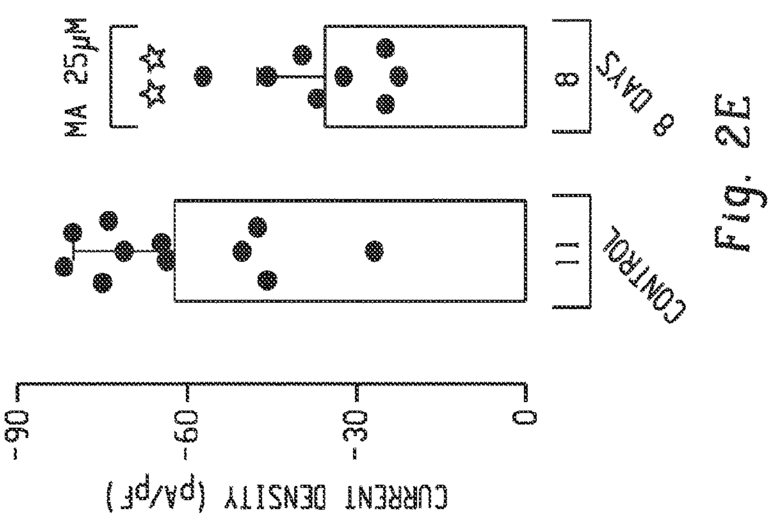
Figures 3A, 3B, 3C, 3D, 3E:
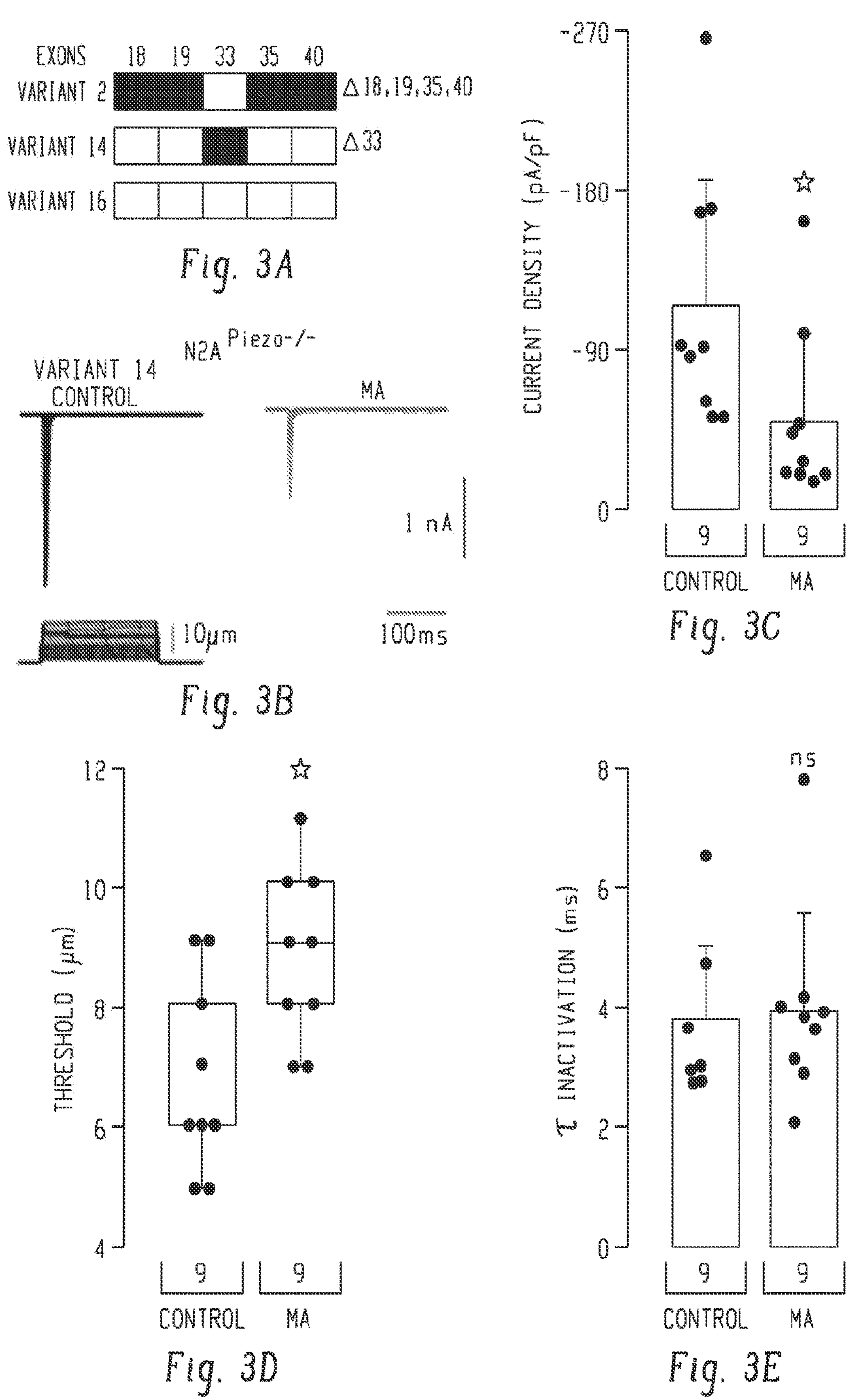

PIEZO2 channels were first characterized in transfected neuro-2a (N2A) cells using an electrically driven piezo-glass probe. We previously determined that N2A plasma membranes can be enriched with MA after overnight incubation and promote high bending stiffness, as determined by mass spectrometry and atomic force microscopy. Importantly, we determined that PIEZO1 displays decreased activity in this membrane environment. To determine whether PIEZO2 can also be modulated by the mechanical properties of the membrane, we transfected Piezo2 variant V2 and measured its mechanocurrents after supplementing the $N2A^{Piezo1-/-}$ (i.e., cells in which the Piezo1 gene has been deleted) cell media with MA, ranging between 1-600 μM overnight. We found that MA inhibits PIEZO2 currents in a concentration-dependent manner (FIG. 1*a*, *b* FIG. 2*a*) with an $IC_{50}$=190.6±14.7 μM (mean±SEM; FIG. 1*b*). Moreover, MA increases the displacement threshold required to elicit PIEZO2 currents by three fold when compared to that of the control cells (FIG. 1*c*), without affecting the time constant of inactivation (FIG. 2*b*).

We required MA concentrations higher than 100 μM to decrease PIEZO2 currents when using overnight supplementation (FIG. 1*b*). Fatty acids can accumulate when their consumption is increased through diet, likewise, we previously demonstrated that MA can also accumulate in the plasma membrane when supplemented in the cell media for several days at low concentrations. Hence, to inhibit PIEZO2 activity with lower doses of MA, we implemented a daily supplementation protocol. Indeed, supplementing $N2A^{Piezo1-/-}$ cells with only 50 μM of MA over the course of four days decreased PIEZO2 currents by 65% (FIG. 1*d*, *e*). As seen with higher concentrations overnight, our low dose serial MA supplementation increases the displacement threshold without altering PIEZO2 inactivation (FIG. 1*f* and FIG. 2*c*). Similar results were obtained when supplementing with 25 μM each day for eight days (FIG. 2*d*-*g*). Showing that MA concentration could be reduced further if the incubation time was lengthened. Notably, MA also inhibited the activity of two other Piezo2 variants that are particularly abundant in the trigeminal ganglion (V14 and 16), indicating that it likely affects most alternatively spliced isoforms of this channel (FIG. 3*a*-*i*). Together, our results demonstrate that MA inhibits PIEZO2 currents by increasing the mechanical threshold required for activation. Thus, as with PIEZO1, PIEZO2 is less active in rigid membranes (≥78 pN).

Figures 4A, 4B, 4C:
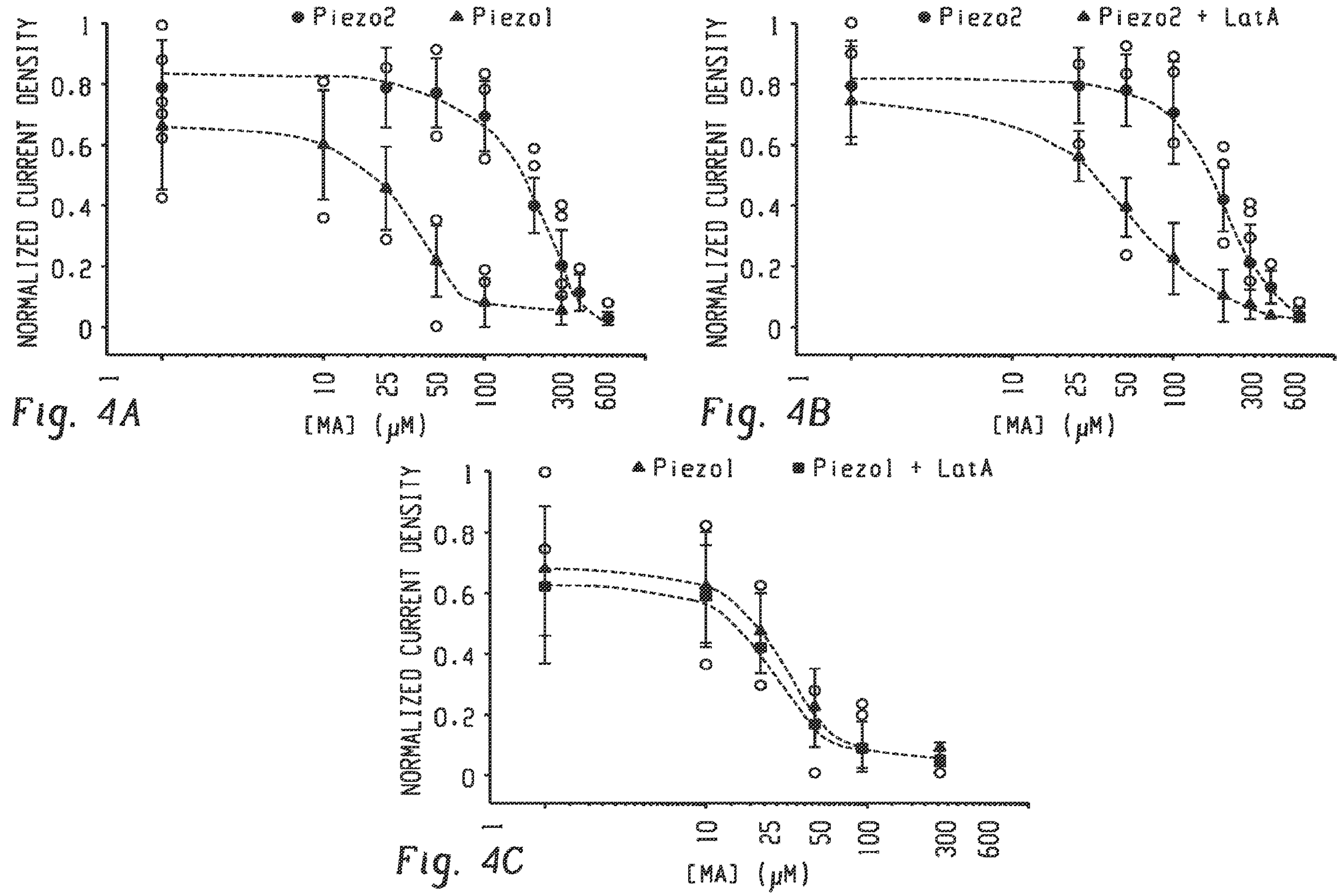
FIG. 4*a-f* shows latrunculin A enhances PIEZO2 inhibition by MA.
Figure 5A:
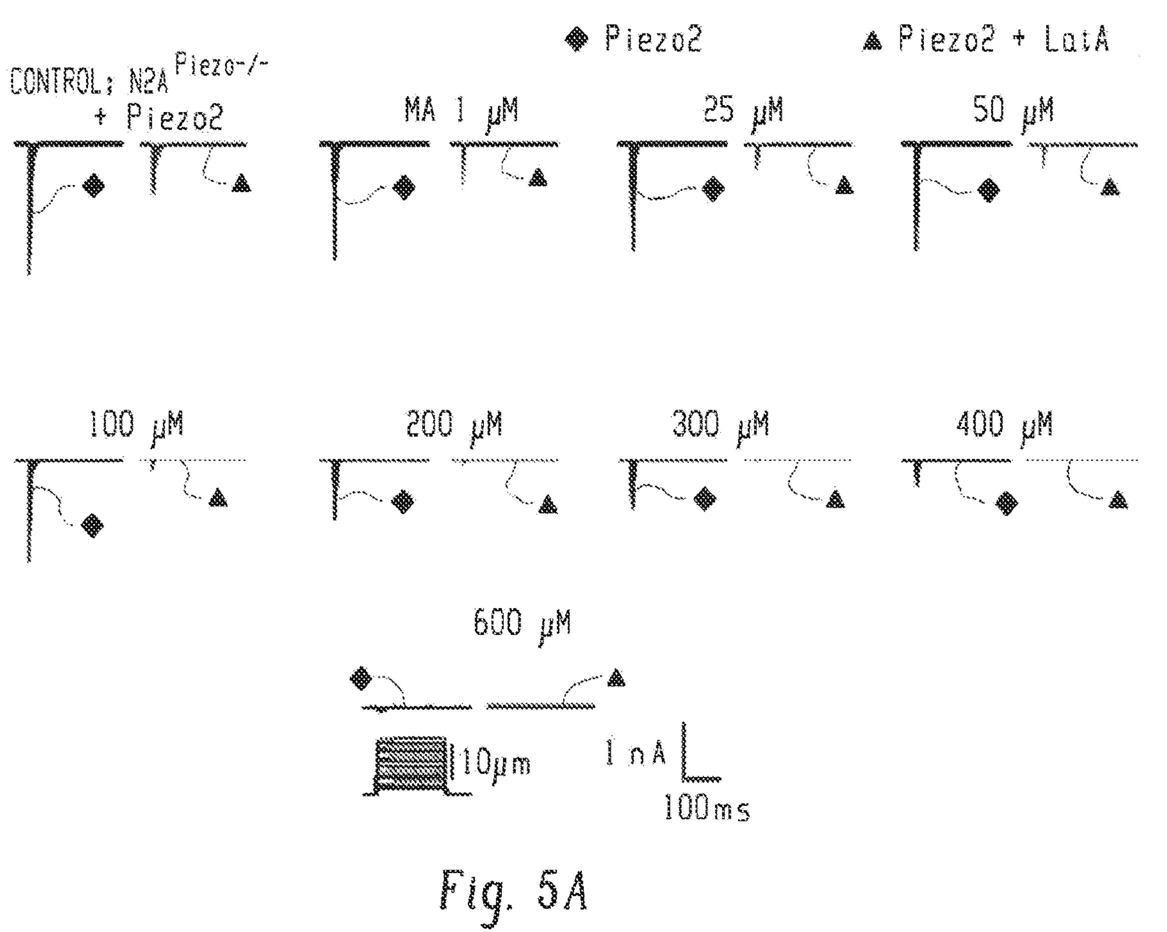
FIG. 5*a-d* also show latrunculin A enhances PIEZO2 inhibition by MA.
Figure 5B:
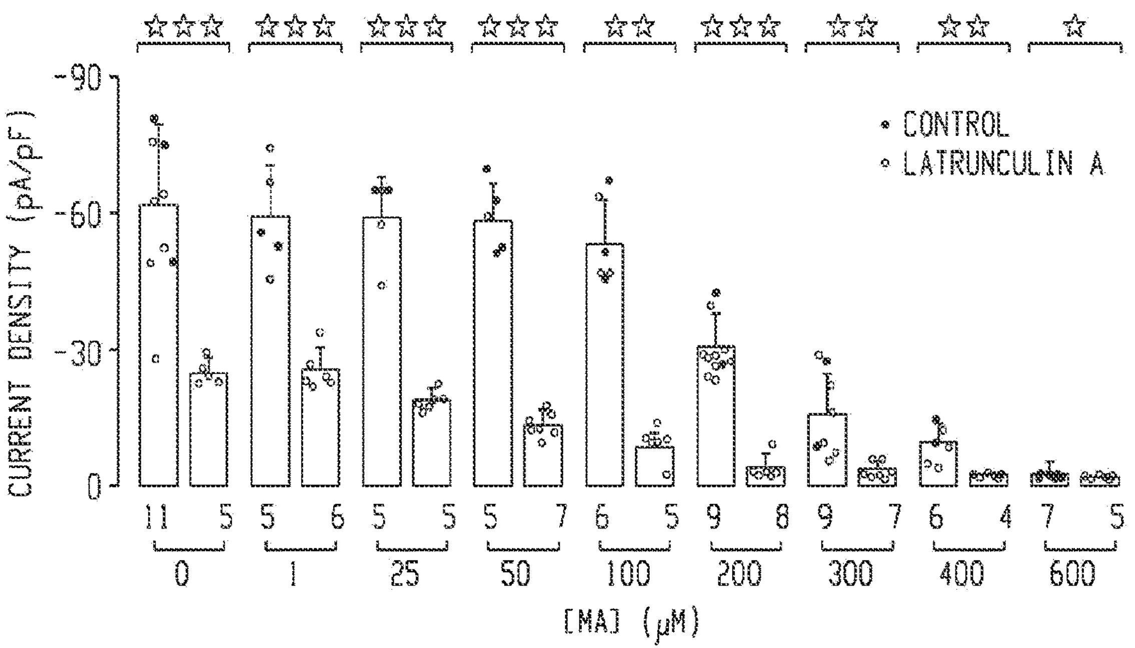
Figures 5C, 5D:
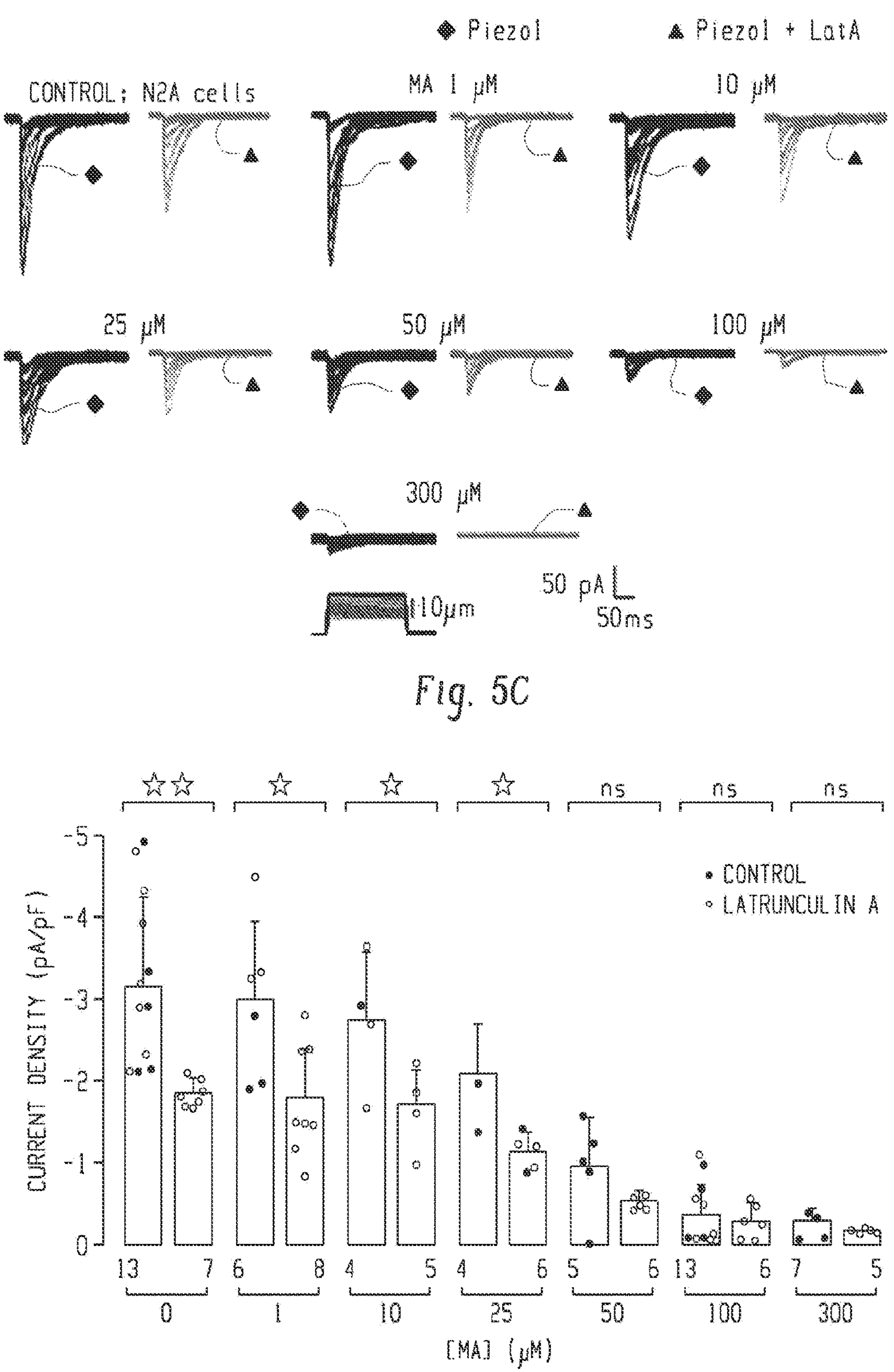

Example 2: PIEZO2 Function Relies on the Plasma Membrane and the Cytoskeleton When comparing PIEZO1 and PIEZO2 activities under increasing MA concentrations, we determined that the $IC_{50}$ for PIEZO1 is 28.3±3.4 μM and for PIEZO2 is 190.6±14.7 μM (mean 127±SEM; FIG. 4*a* FIG. 5*a*-*d*). Several lines of evidence suggest that PIEZO2 requires the cytoskeleton for activation, whereas PIEZO1 can be solely activated by membrane tension in inside-out patches. These distinct features may explain why ~7 times more MA is needed to inhibit PIEZO2 channels than PIEZO1. We previously demonstrated that disrupting the actin filaments does not affect plasma membrane bending stiffness of untreated or MA-enriched N2A cells. Hence, to determine the contribution of the actin cytoskeleton on PIEZO2 gating, we treated MA-enriched cells with latrunculin A and compared their mechanically-evoked responses with those cells treated solely with MA. Latrunculin A treatment results in a pronounced leftward shift in the MA dose-response profile for PIEZO2 ($IC_{50}$=75.4±13.3 μM; mean±SEM, FIG. 4*b*) that is closer to that of Piezo1 (FIG. 4*a*). On the other hand, the 137 MA dose-response profile of PIEZO1 is similar in control and latrunculin-treated cells ($IC_{50}$=28.3 μM±3.4 control vs. 25.6 μM±8.4 latrunculin-treated cells, 138 mean±SEM;

FIG. 4*c* and FIG. 5*c, d*), indicating that the mechanism of PIEZO1 current inhibition by MA only depends on the plasma membrane. These results implicate the cytoskeleton as a key determinant of the differential responses of PIEZO2 and PIEZO1 to MA.

Figures 4D, 4E, 4F:
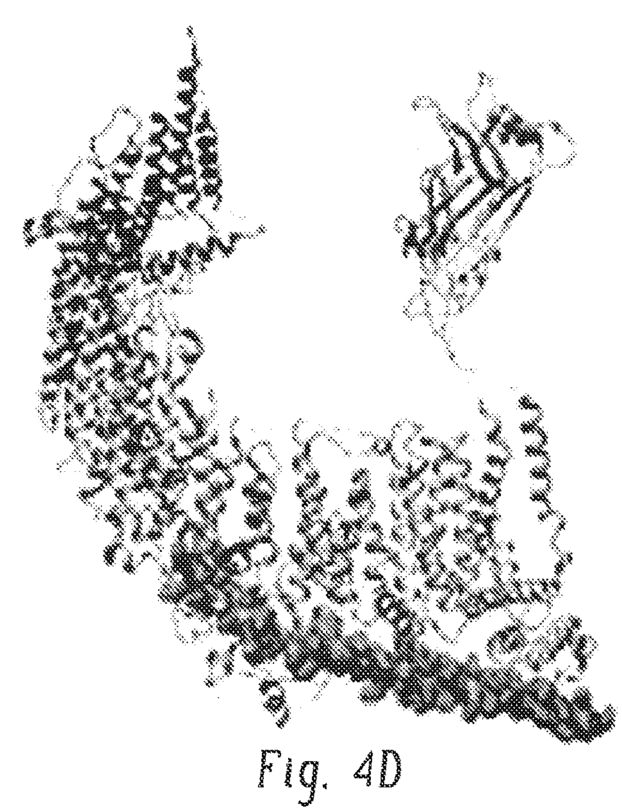
Figure 6A:
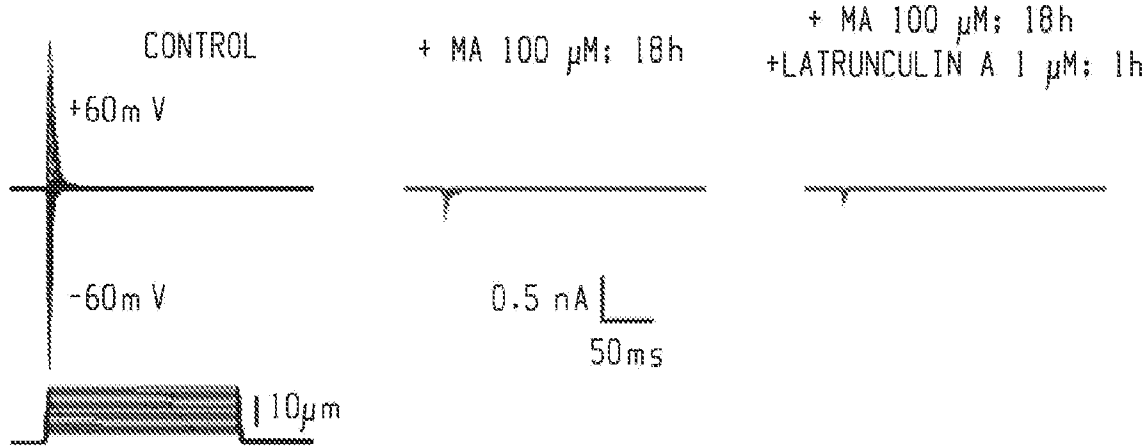
FIG. 6*a-e* also show latrunculin A enhances PIEZO2 inhibition by MA.
Figure 6B:
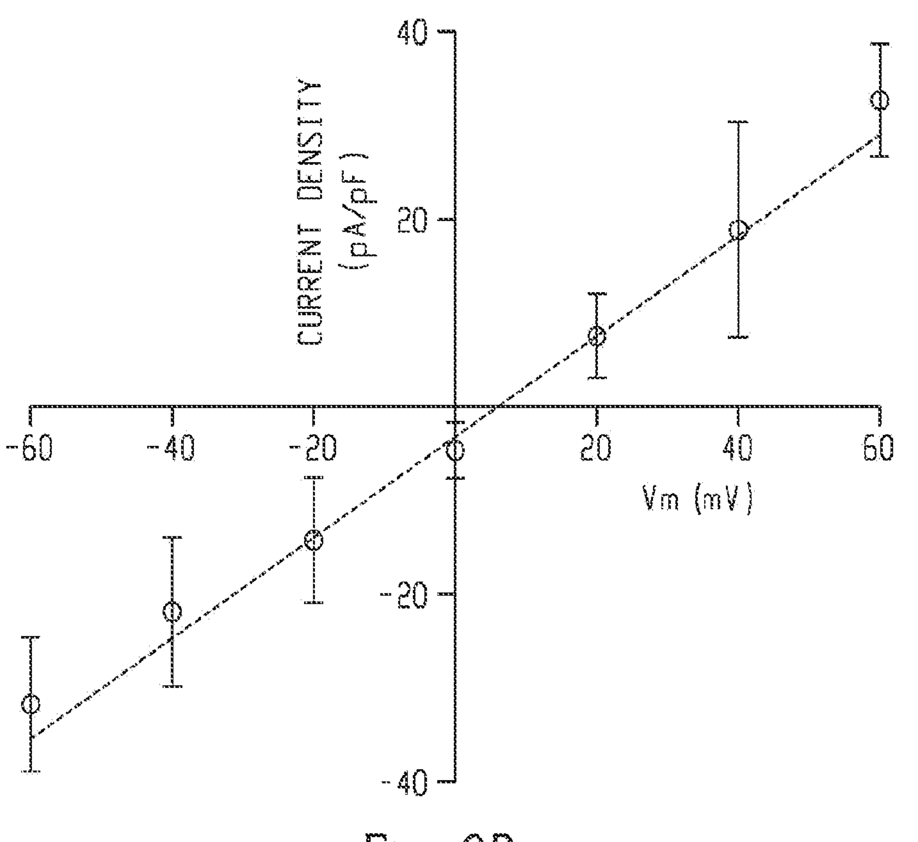
Figure 6E:
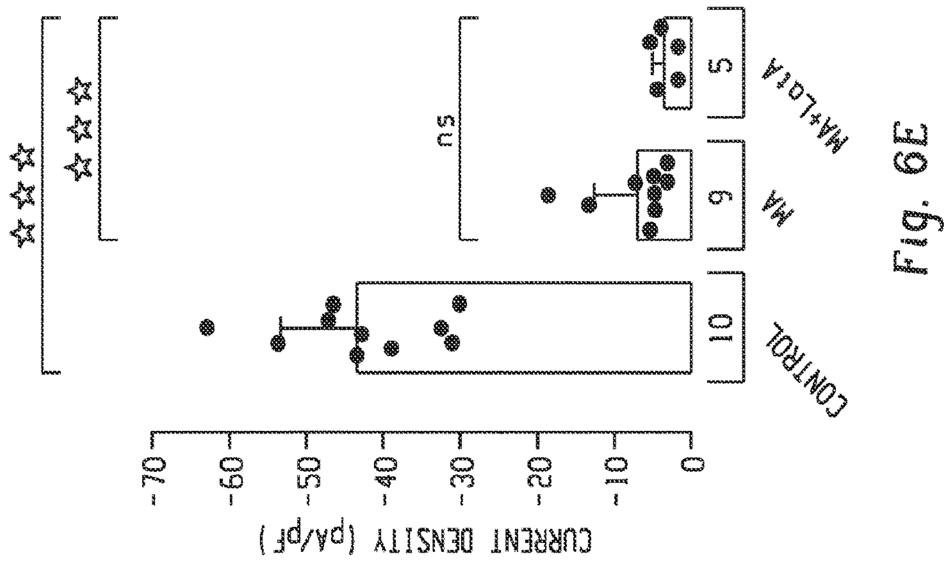
Figure 6D:
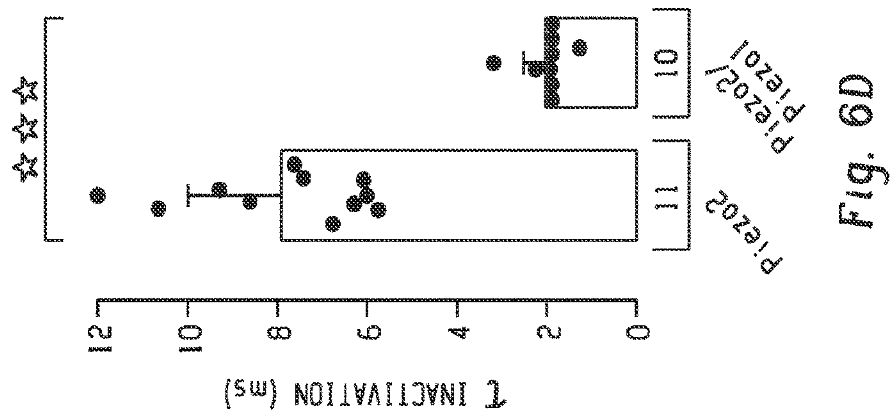
Figure 6C:
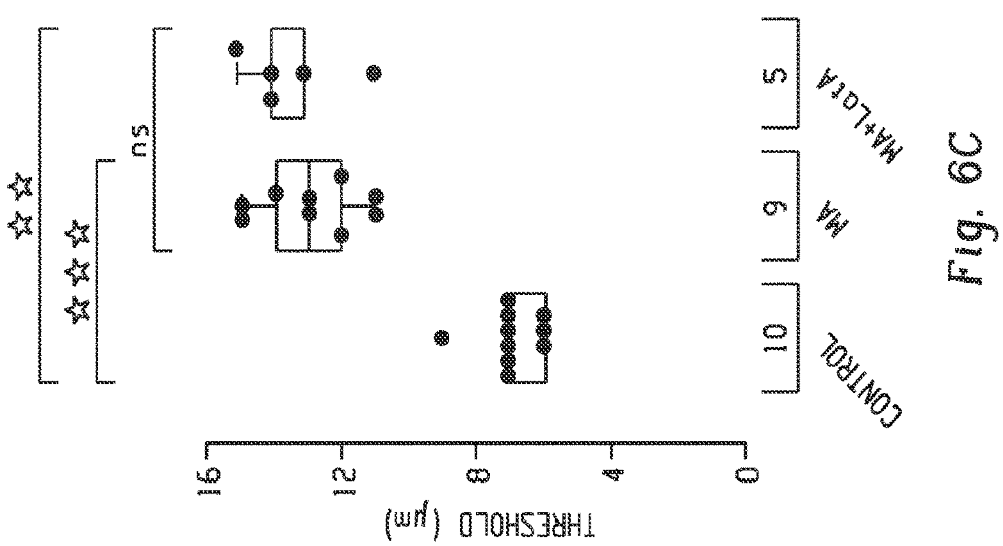

Unlike PIEZO1, the effect that a rigid plasma membrane (i.e., enriched with $MA_{24}$) exerts on PIEZO2 becomes more apparent when the cytoskeleton is pharmacologically disrupted (FIG. 4*b, c*). Next, we wondered if modifying PIEZO2 intracellular regions (likely interacting with the cytoskeleton elements) could enhance inhibition by MA, similar to the effect observed with the latrunculin A treatment. Both PIEZO1 and PIEZO2 contain a 90 Å-long intracellular helix termed the beam (i.e., connects the transmembrane blades with the central pore), that we reasoned might also tether the channels to the cytoskeleton. Notably, the sequence identity between the PIEZO1 and PIEZO2 beams is low (35%), and thus could account for the different responses of these channels to MA inhibition. To test this hypothesis, we engineered a PIEZO2 chimera in which we replaced its beam with that of PIEZO1 (FIG. 4*d*). The PIEZO2-PIEZO1 beam chimera displays similar functional properties to PIEZO2, including the reversal potential (7.7 mV PIEZO2 vs. 5.6 mV chimera) and the displacement threshold (6.27±1.35 μm PIEZO2 vs. 6.9±0.8 μm chimera, mean±SD; FIG. 6*a-c*). However, the time constant of inactivation of the chimera is faster than PIEZO2 (7.59±1.96 ms PIEZO2 vs. 1.91±0.46 ms chimera, mean±SD; FIGS. 2*c* and 6*d*). Remarkably, transferring the PIEZO1 beam to PIEZO2 resulted in channels that are much more sensitive to MA inhibition (100 μM overnight), similar to those seen for PIEZO1 (FIG. 4*e*). This chimera requires a higher mechanical stimulus to open when expressed in cells supplemented with MA (100 μM overnight; FIG. 6*c*) and this effect is not modulated by latrunculin A treatment (FIG. 4*c, f*). Taken together, our results highlight that PIEZO2 mechano-sensitivity relies on the synergy between the mechanics of the plasma membrane and interaction with cytoskeleton elements.

Example 3: Margaric Acid Decreases Mechano-Currents in Sensory Cells

Figures 7A, 7B, 7C:
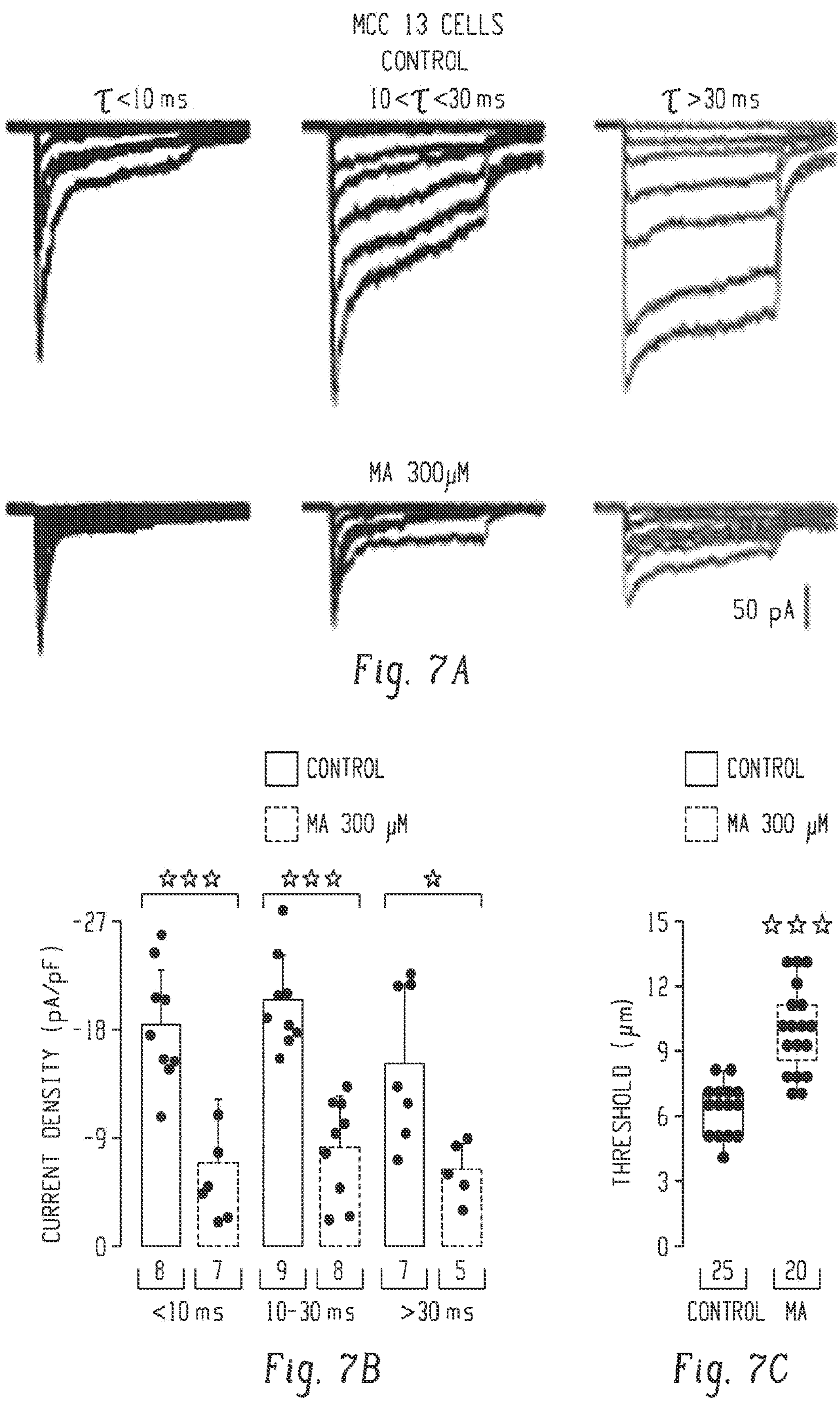

Piezo2 is expressed in Merkel cells and its innervating afferents, where it has been shown to transduce skin indentation and whisker deflection into electrical signals. In view of the results described above in a heterologous expression system, we asked whether MA could decrease PIEZO2 currents in cells that mediate touch sensation. To this end, we measured the effect of MA on PIEZO2 activity in the human Merkel cell carcinoma cell line (MCC13) and acutely cultured mouse DRG neurons. Like dissociated Merkel cells, MCC13 displayed mechanosensitive currents with a range of inactivation kinetics (FIG. 7*a*). These mechano-currents have been shown to be mediated by PIEZO2. As with our experiments using transiently transfected N2A cells, MA supplementation in MCC13 decreases endogenous PIEZO2 currents (FIG. 7*a, b*) by increasing the displacement threshold (FIG. 7*c*). Similarly, cultured mouse DRG neurons also exhibit mechano-currents with varying inactivation kinetics. However, in this case, only the rapidly adapting currents (t<10 ms) have been assigned to PIEZO2. Notably, MA supplementation decreased the current magnitude of all DRG neurons mechano-evoked currents, including those known to be mediated by PIEZO2 (FIG. 7*d, e*) by increasing the displacement threshold (FIG. 7*f*). Taken together, these findings translate our heterologous expression results to show that MA decreases the endogenous mechano-currents in diverse cell-types known to be involved in mechanosensation.

Figure 8A:
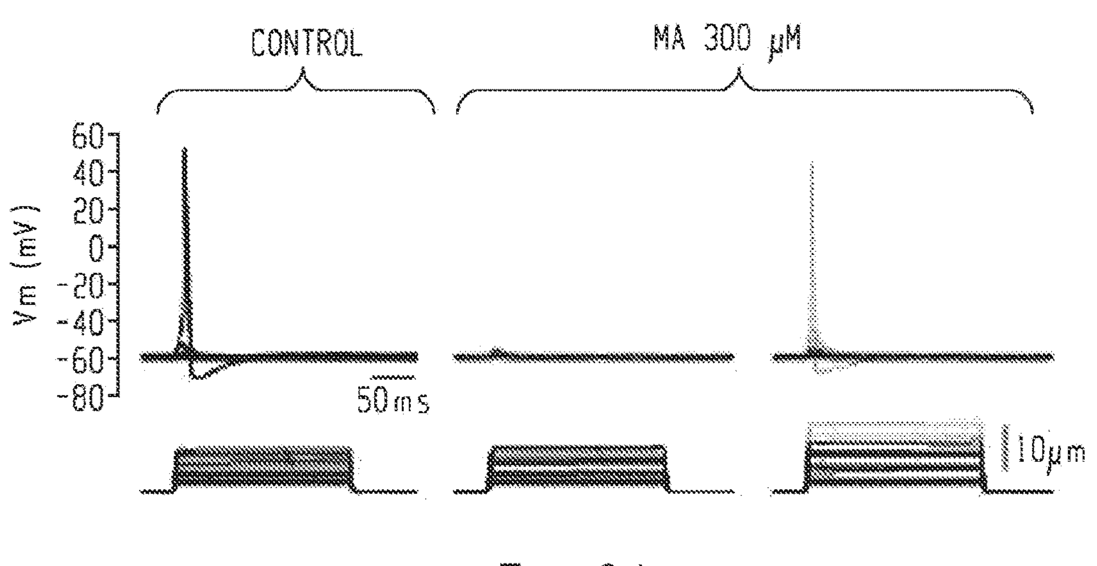
FIG. 8*a-d* shows MA decreases action potentials elicited by mechanical stimuli in mouse DRG neurons.
Figure 8B:
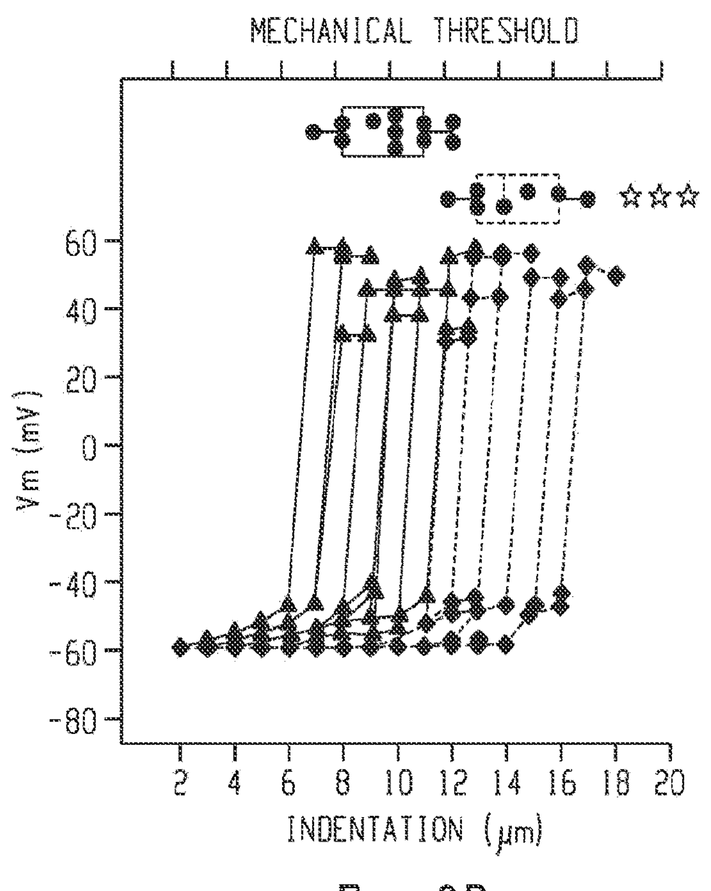
Figure 8C:
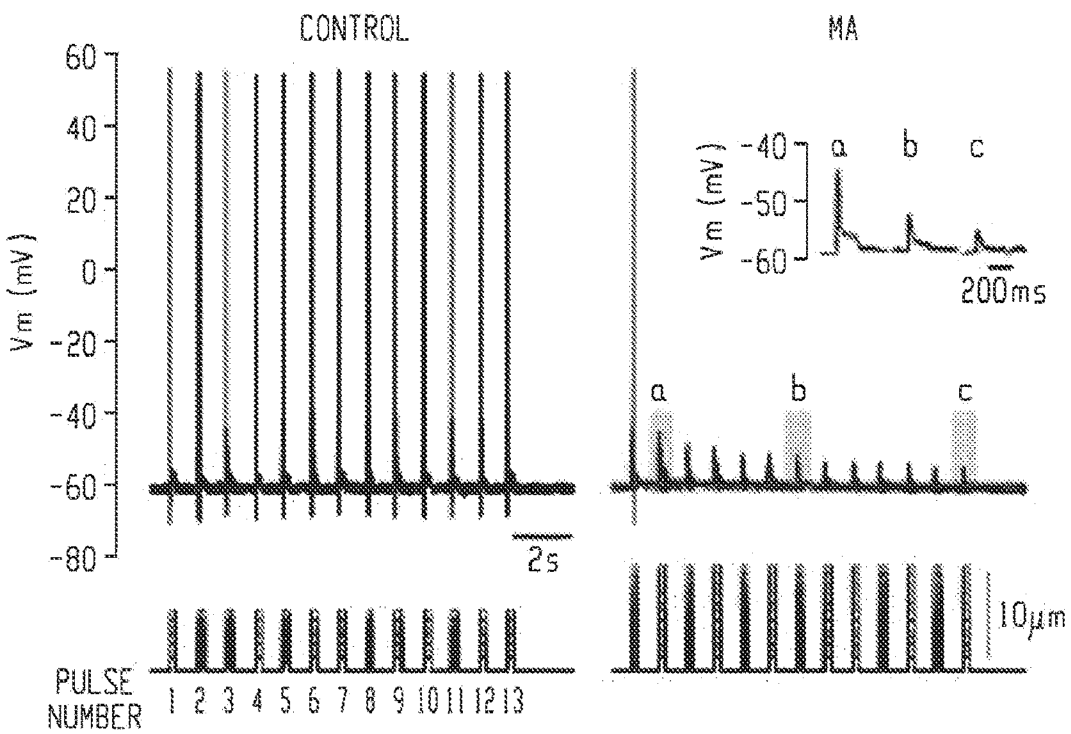
Figure 8D:
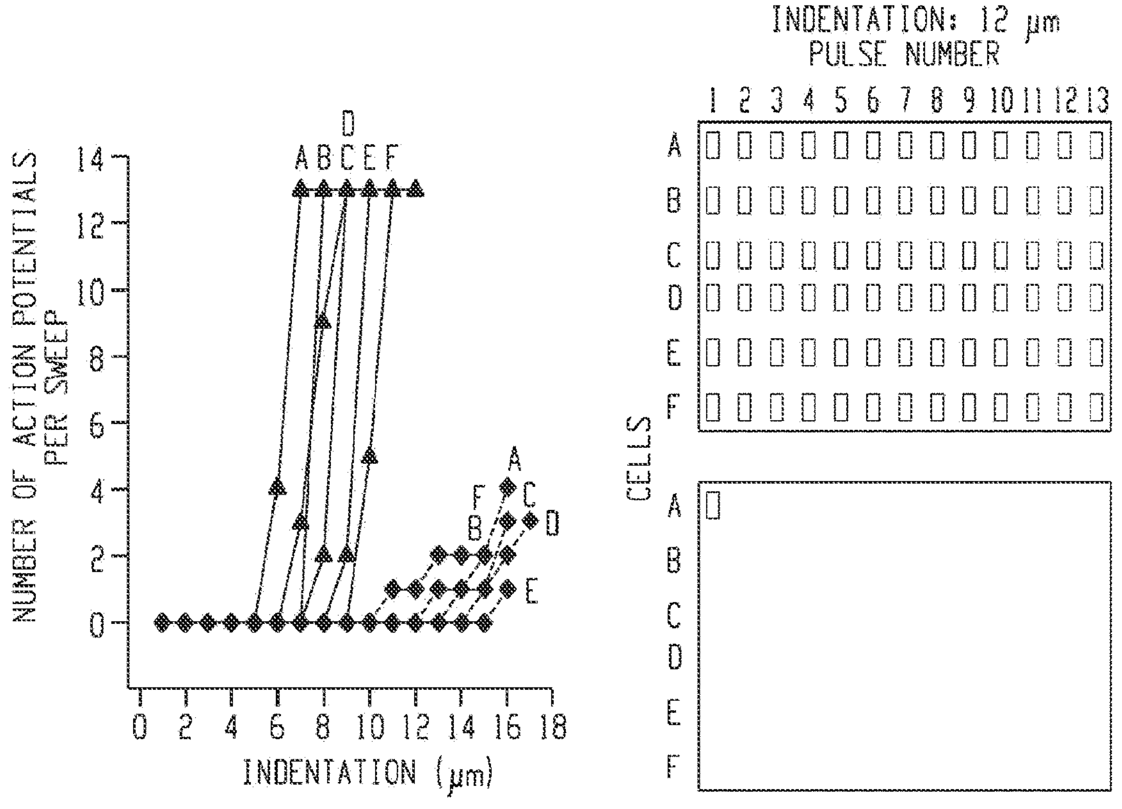

Example 4: Margaric Acid Diminishes Action Potential Firing Elicited by Mechanical Stimuli The detection of touch relies on mechanosensitive ion channels expressed in sensory nerve endings. These channels translate mechanical stimuli into electrical signals, depolarize neurons and, in turn, generate action potentials that propagate toward the central nervous system. PIEZO2 mediates a major proportion of the mechano-activated excitatory currents in mouse DRG neurons. Since MA decreases mechano-currents (including those of PIEZO2), we sought to determine if this saturated fatty acid would also impair the ability of DRG neurons to elicit mechanically activated action potentials. Indeed, we found that MA completely inhibits action potential generation in mouse DRG neurons when indentation steps were smaller than 12 μm (FIG. 8*a*, left and middle panels). Nevertheless, we were able to elicit action potentials in MA-treated neurons after using larger indentation steps [12 μm for MA (red steps) vs. 7-12 μm for control; FIG. 8*a* right panel and 8*b*]. Furthermore, stimulating DRG neurons with a series of 1 Hz mechanical stimulus trains revealed that cells enriched with MA evoked less action potentials than the control (<12 μm; FIG. 8*c*), even at large indentation magnitudes (>12 μm; FIG. 8*d*). Interestingly, MA enriched neurons also displayed a progressive decline in membrane potential as the indentation pulse number progressed (FIG. 8*c*, inset). This suggests that after repetitive stimulation, it is more difficult to open mechanosensitive channels in MA-treated neurons. Taken together, MA supplementation increases the mechanical threshold required for DRG neurons to fire action potentials.

The mechanically driven depolarization in DRG neurons activates voltage-gated $Na_+$- and $K_+$-channels that are critical for generating action potentials. To determine whether MA impairs the function of ion channels downstream of mechanical activation, we recorded voltage-gated currents in the presence or absence of MA. We found no significant differences in the amplitudes of the voltage-activated inward $Na_+$ and outward $K_+$ currents of control and MA-enriched DRG neurons (FIG. 9*a-c*). Moreover, MA supplementation did not alter membrane potential, when measured in the whole-cell configuration (FIG. 9*d*). Notably, we found no difference in action potential firing elicited by current injection between control and MA-enriched neurons (FIG. 9*e, f*).

Altogether, our results indicate that MA does not alter DRG neuronal electrical excitability but instead specifically decrease action potential firing evoked by mechanical stimulation.

Example 5: Margaric Acid Counteracts PIEZO2 Bradykinin Sensitization

Figure 10A:
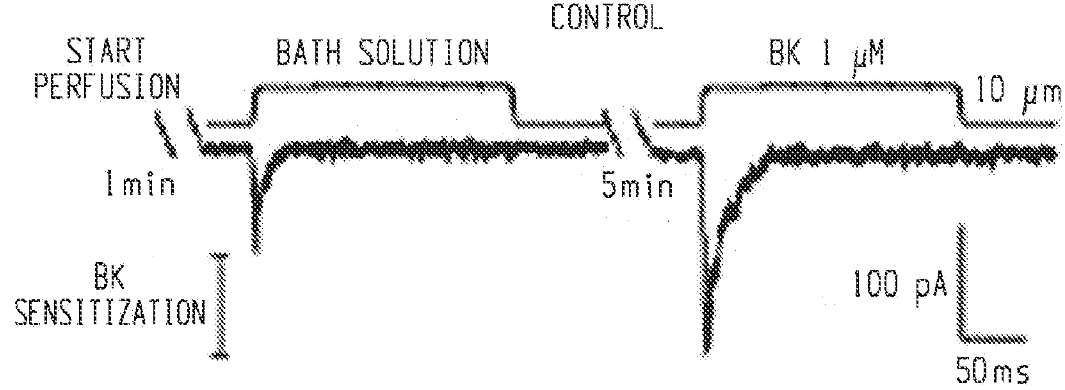
Figure 10A:
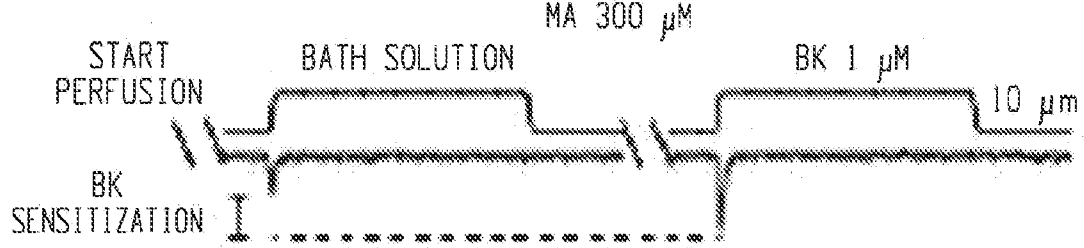
Figure 10B:
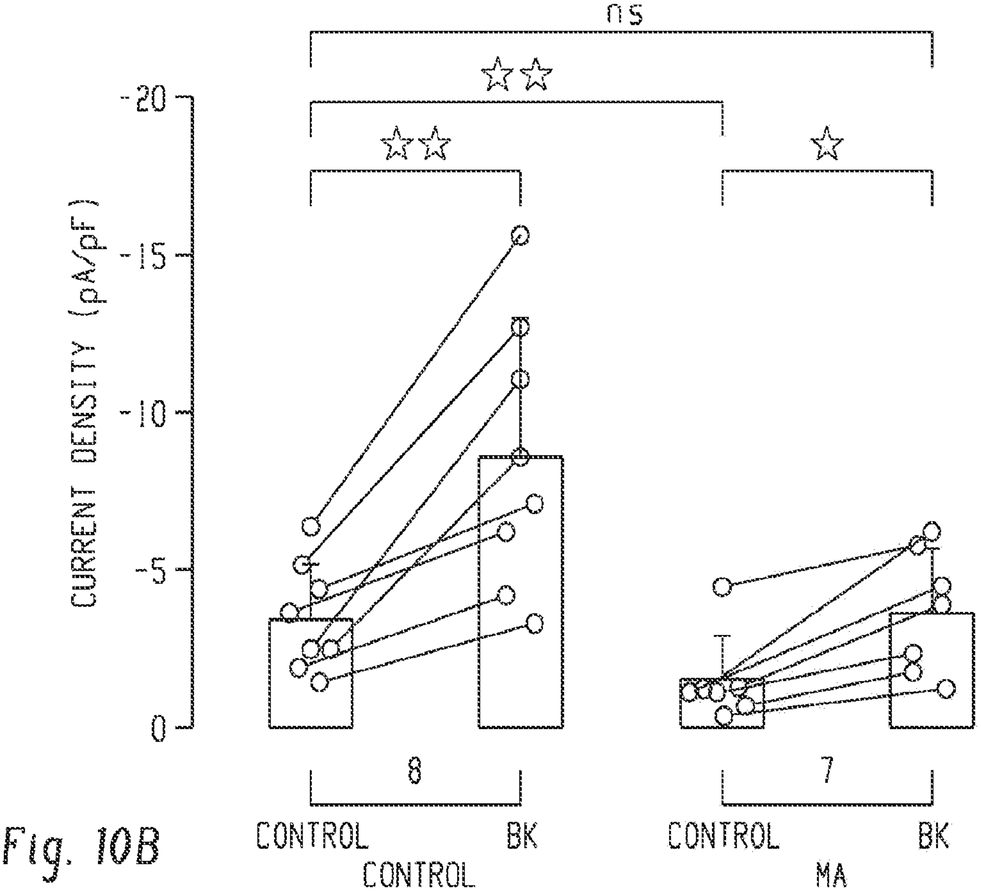

Tissue damage is frequently accompanied by the accumulation of proalgesic inflammatory agents such as bradykinin, eicosanoids, and protons. These inflammatory molecules bind or interact with diverse membrane proteins, activate intracellular signaling cascades, and increase sensitivity to sensory stimuli leading to allodynia or hyperalgesia. It has been demonstrated that PIEZO2 mechanically-evoked currents are potentiated downstream of the activation of the bradykinin beta 2 receptor in DRG neurons. Molecules that decrease PIEZO2 sensitization could therefore be beneficial to treat mechanical allodynia. Given that MA significantly decreased PIEZO2 currents in DRG neurons (FIG. 7*d-f*), we wondered whether MA supplementation also decreases bradykinin-mediated PIEZO2 sensitization. Similar to previous reports, we found that acute bradykinin perfusion sensitized mechano-activated currents of DRG neurons (2.5-fold increase; FIGS. 10*a*, top and 10*b*). As predicted, MA supplementation decreases the mechano-currents, even after sensitization with bradykinin (FIG. 10*a*, bottom). Remarkably, the currents recorded in MA-supplemented neurons after bradykinin administration (FIG. 10*a* and FIG. 11) closely resembled those of control DRG neurons (3.36±1.68 pA/pF control vs. 3.64±1.96 pA/pF bradykinin with MA, mean±SD; FIG. 10*b*). Similar findings were observed with longer exposures to bradykinin. Overnight incubation with bradykinin potentiated the magnitude of all mechano-evoked currents of the DRG neurons (FIG. 10*c* middle panel and 10*d*). However, combined overnight incubation with bradykinin and MA restored the current densities to those of control neurons (FIG. 10*c, d*). Altogether, these results support that enriching the plasma membrane with MA could counteract the mechanical sensitization evoked by bradykinin, reducing the mechano-currents to non-inflammatory levels. Hence, MA is a promising molecule for decreasing mechanical hypersensitivity.

Example 6: Margaric Acid Decreases PIEZO2-Mediated Mechanical Allodynia

Figures 12A, 12B:
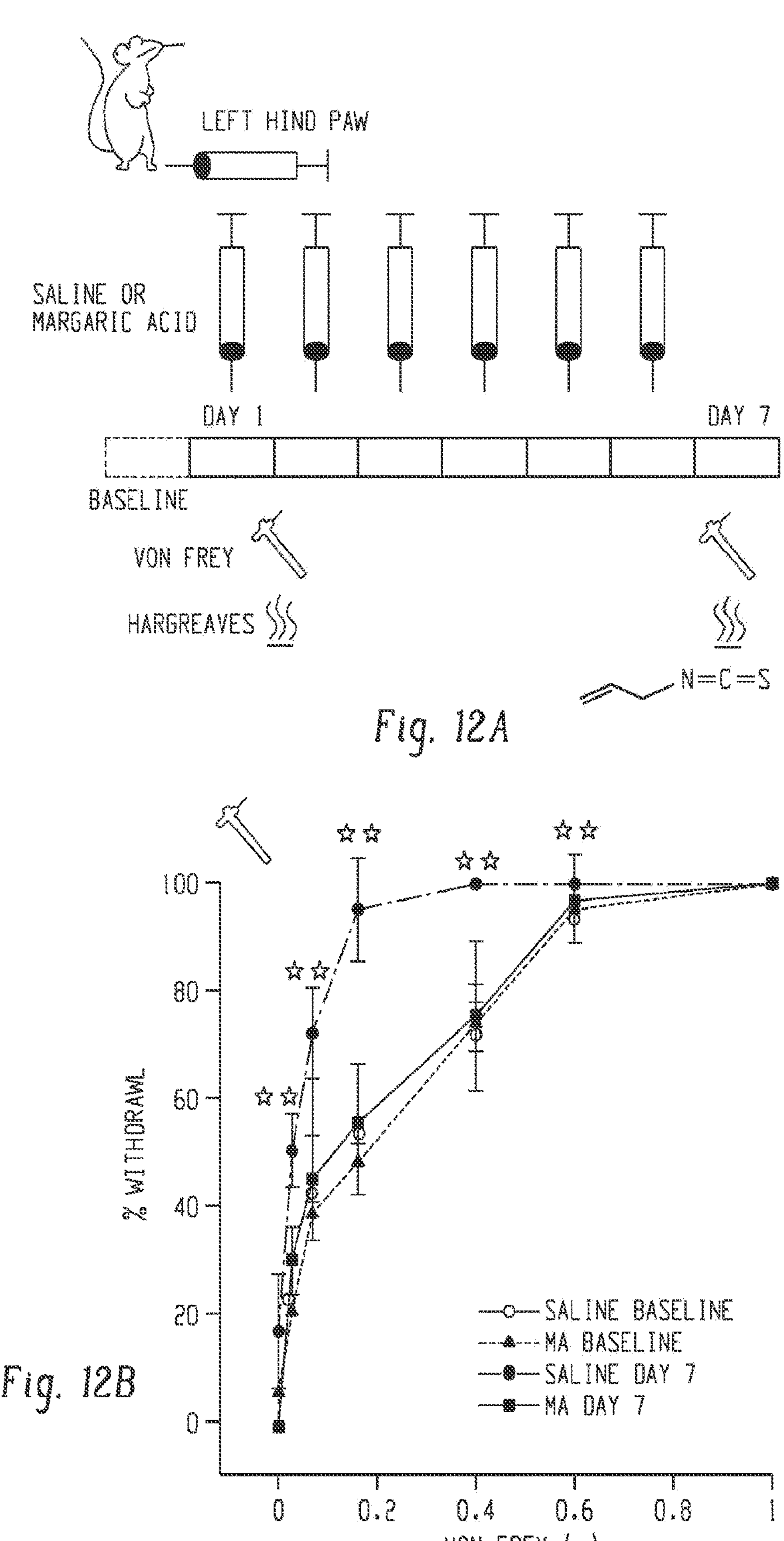
FIG. 12*a-d* shows administration of MA protects against tactile allodynia in mice.

Previous work from our group and others have demonstrated that PIEZO2 is required for mechanical allodynia in both mice and humans. A major prediction from our data is that MA administration would protect against this kind of pain. Acute sub-dermal injection of MA had no effect on baseline touch responses (FIG. 12*a, b*), likely because fatty acids require time to be incorporated and accumulate in membranes in order to modulate PIEZO2 function. Hence, we designed an experiment to examine nociceptive responses after chronic exposure to MA (FIG. 12*a*). Mice injected daily with a small amount of saline into their hind paw showed pronounced hypersensitivity to punctate touch within 7 days (a repeated injury model; FIG. 12*b*).

Figures 12C, 12D:
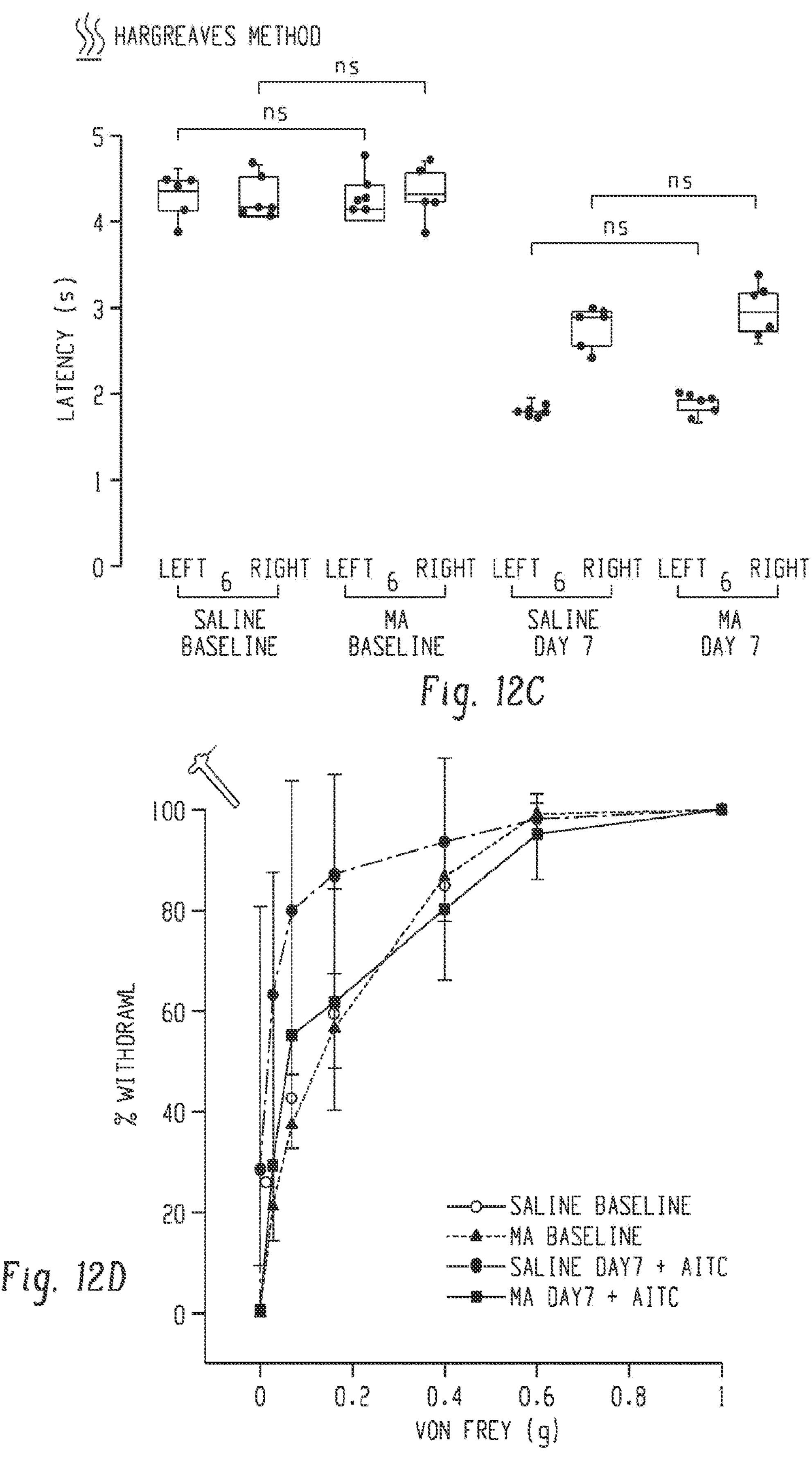

Astoundingly, mice failed to develop this type of heightened withdrawal response when MA was included in the injections (FIG. 12*b*). Importantly, this type of mild injury or daily exposure to MA had no effect on thermal withdrawal latencies as measured by Hargreaves radiant heat test (FIG. 12*c*). Allyl isothiocyanate (AITC), the pungent compound of wasabi and mustard oil, causes pain by activating nociceptors. We topically applied AITC to the mice's left hind paws to induce a heightened neuro-inflammatory pain. Normally, AITC immediately causes mice to withdraw their hind paws from even the lightest von Frey filaments 253 (<0.16 g; FIG. 12*d*). However, mice treated with MA for 7 days responded with sensitivities similar to their basal response from the previous week (FIG. 12*d*). Altogether, these results provide proof of concept that reduction of PIEZO2 function by MA is a feasible pharmacological approach for treating mechanical allodynia.

Figures 13A, 13B, 13C, 13D, 13E:
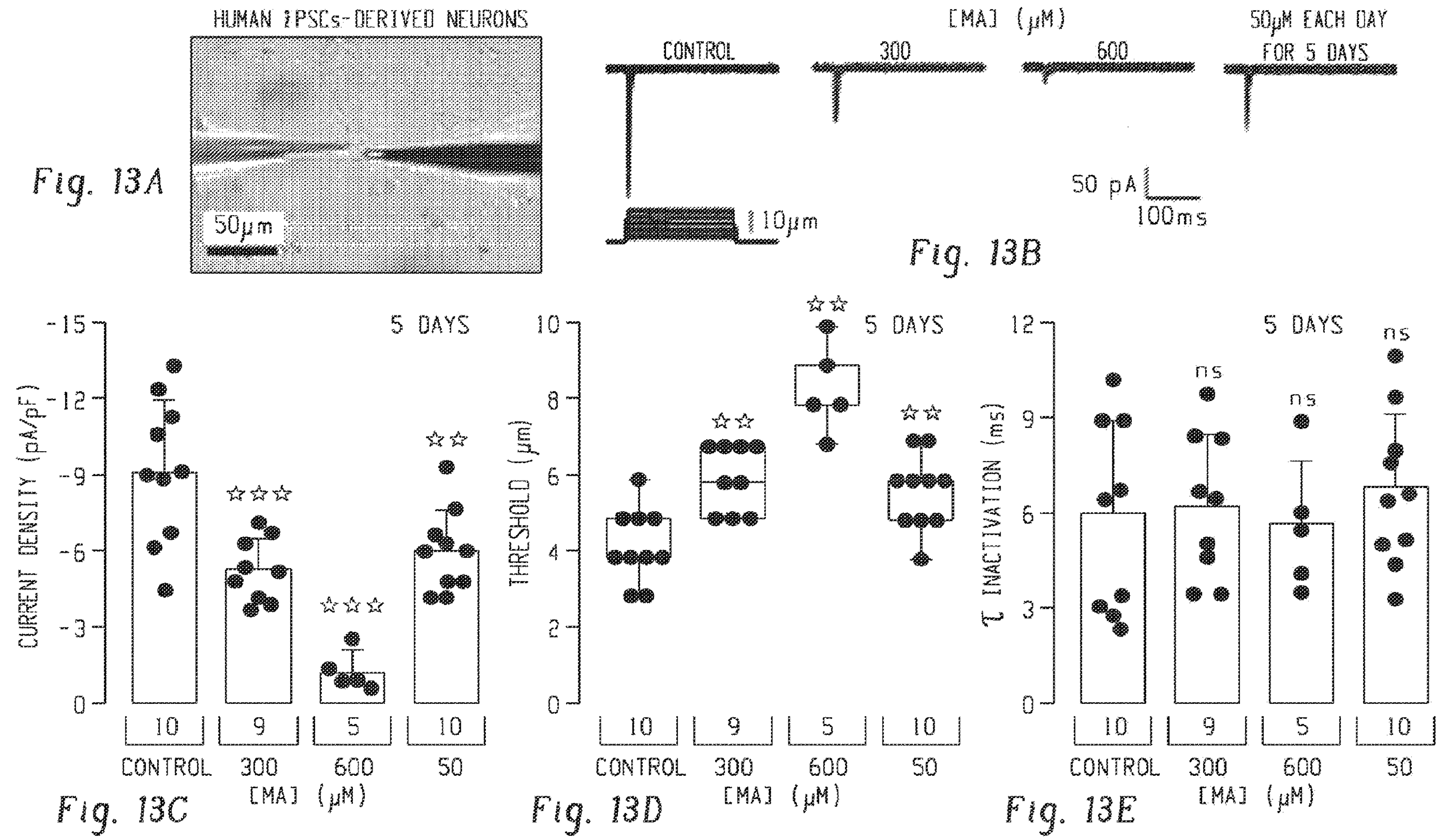
Figure 15A:
Figure 15A:
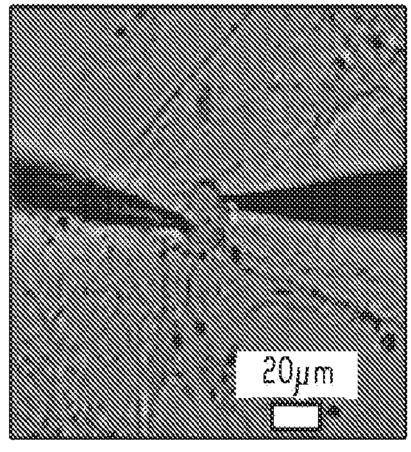
Figure 15B:
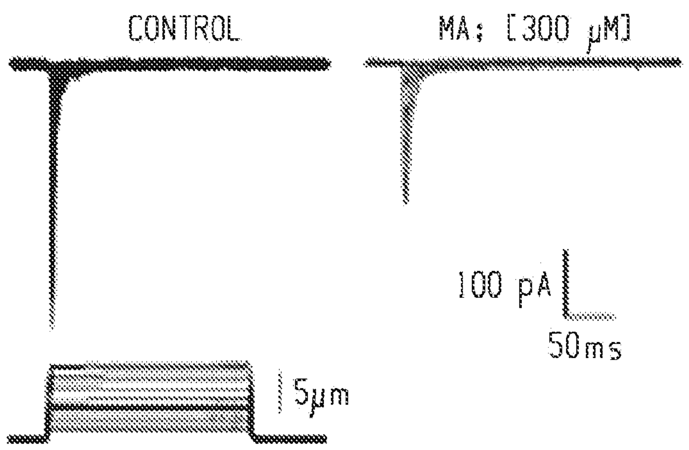
Figure 15C:
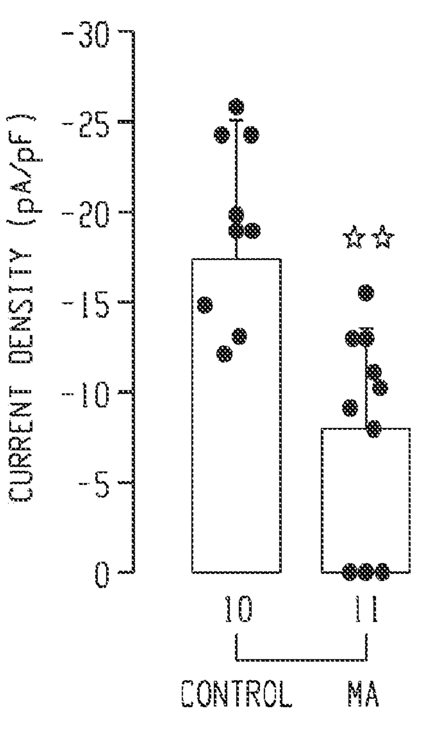
Figure 15D:
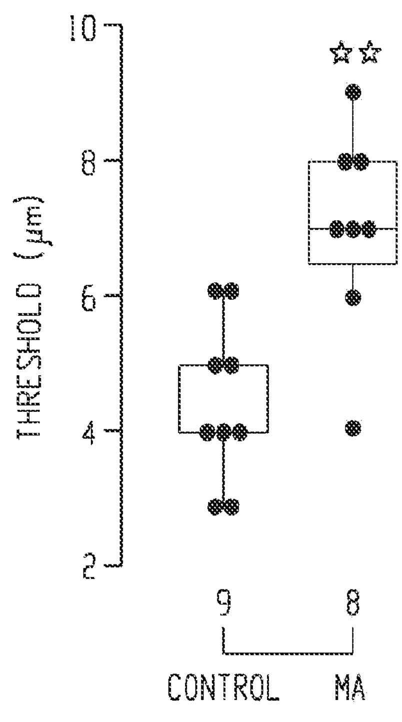

Example 7: Margaric Acid Decreases Mechano-Currents in Human iPSC-Derived Neurons Our previous results demonstrate that enriching the plasma membrane with MA had an inhibitory effect on mouse PIEZO2 function in vitro, ex vivo, and in vivo. These results have a clear potential for translation. Hence, we explicitly tested the effect of MA on human sensory neurons. Recently, we developed a platform to robustly and reproducibly reprogram human induced pluripotent stem cells (iPSCs) into well-characterized neurons that have functional and transcriptional hallmarks indicative of low threshold mechano-receptors (FIG. 13*a*). Notably, these in vitro-derived touch neurons all have mechanically-evoked currents that are entirely dependent on PIEZO2 expression. Overnight incubation of human iPSCs with MA (300 and 600 μM) significantly reduced endogenous PIEZO2 currents (FIG. 13*b-c*). Furthermore, we confirmed these results by measuring mechano-currents of human PIEZO2 transfected in N2A$^{Piezo1-/-}$ cells supplemented with MA (FIG. 14*a-b*). Moreover, supplementing human iPSC270 derived neurons with 50 μM MA each day for 5 days (a strategy analogous to the one used for mice) also significantly decreased PIEZO2 currents (FIG. 13*b-c*). As expected, MA increased the mechanical threshold needed to activate the human channel, without altering the time constant of inactivation, mirroring the results obtained with the murine ortholog (FIG. 13*d-e* and FIG. 14*c-d*). Similar to mouse cultured DRG neurons, MA did not change voltage-activated inward $Na_+$ and outward $K_+$ currents when compared to control human iPSC-derived neurons (FIG. 13*f-h*). These findings indicate that MA specifically affects mechanically-activated currents while keeping intact the electrical excitability of human sensory neurons. As MA is commonly found in foods such as dairy fat, rye, and fish, we speculate that including this fatty acid as a dietary supplement or topical ointment may be a strategy to alleviate mechanical allodynia in humans.

Example 8: MA Decreases Mechano-Activated Currents in Rat DRG Neurons

FIGS. 15 and 16 further show MA decreases mechano-activated currents in rat DRG neurons. PIEZO2 is the essential transduction channel for touch discrimination, vibinfion, and proprioception. Mice and humans lacking Piezo2 experience severe mechanosensory and proprioceptive deficits and fail to develop tactile allodynia. Bradykinin, a proalgesic agent released during inflammation, potentiates PIEZO2 activity. Molecules that decrease PIEZO2 function could ameliorate tactile allodynia. Here, we find that the dietary fatty acid margaric acid (MA) decreases PIEZO2 function in a dose-dependent manner. Chimera analyses demonstrate that the PIEZO2 beam is a key region tuning MA-mediated channel inhibition. MA reduces neuronal action potential firing elicited by mechanical stimuli in mice and rat neurons, PIEZO2 potentiation by bradykinin, and PIEZO2 currents in touch neurons derived from human induced pluripotent stem cells. Finally, we demonstrate that MA ameliorates hypersensitivity to touch after injury in mice. Our findings report a natural product that inhibits PIEZO2 function, reveal a key region for channel inhibition, and provide evidence for new avenues to treat tactile allodynia and other forms of pain.

Example 9: Combination of MA and EPA

Figures 18A, 18B, 18C, 18D:
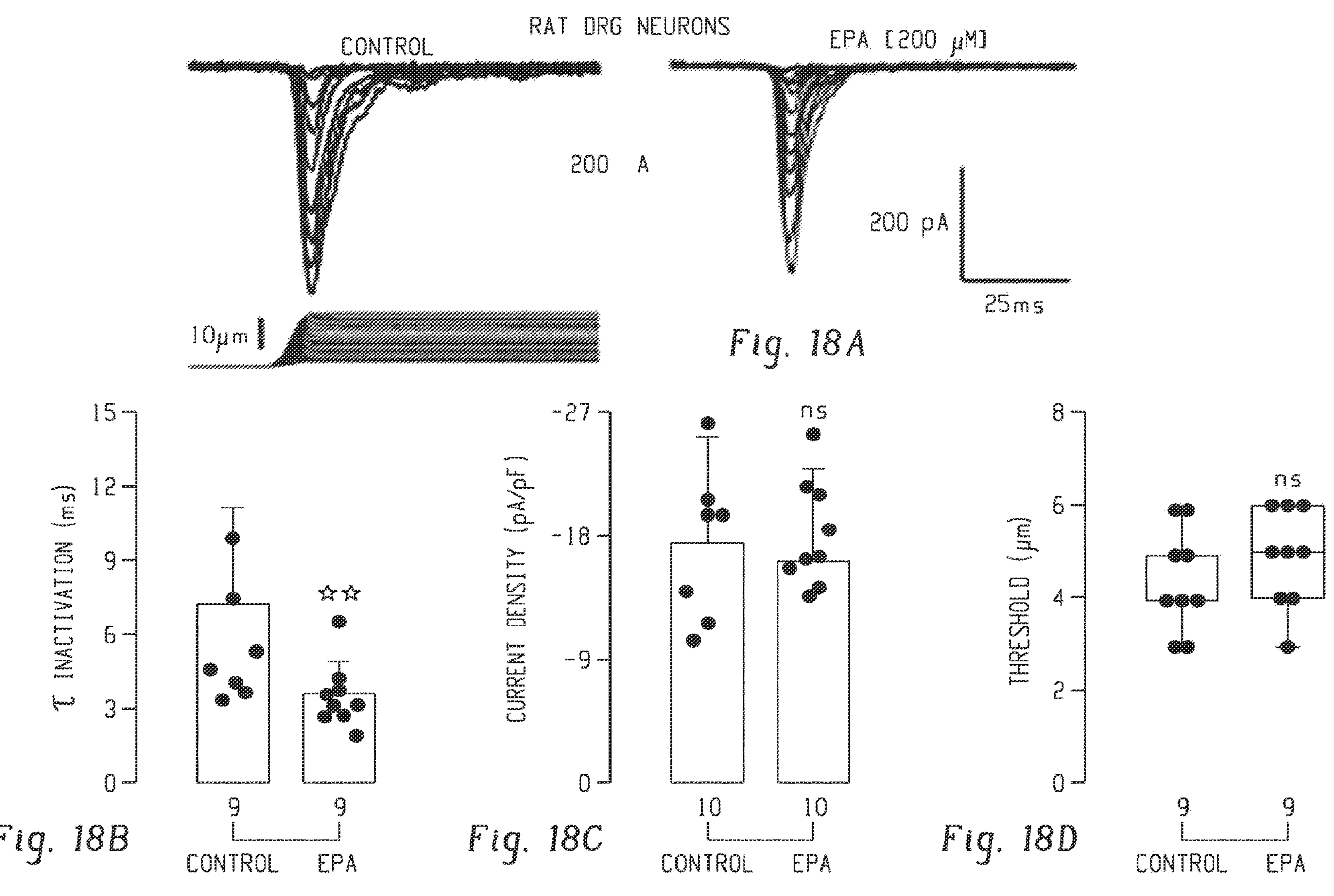
FIGS. 18*a-d* show eicosapentaenoic acid (EPA) supplementation decreases the time constants of inactivation of PIEZO2 in rat DRG neurons.

As shown in FIG. 17, an omega-3 enriched diet decreases the time constants of inactivation of PIEZO2 in mouse DRG neurons. As shown in FIG. 18, eicosapentaenoic acid (EPA) supplementation decreases the time constants of inactivation of PIEZO2 in rat DRG neurons. As shown in FIG. 19, EPA supplementation abrogates the phenotype of PIEZO2 arthrogryposis mutations. As shown in FIG. 20, EPA supplementation decreases the time constants of inactivation of heterologously-expressed mouse PIEZO2 currents in N2A$^{Piezo1-/-}$ cells.

Example 10: MA and EPA have Synergistic Effects on PIEZO2 Function in Mouse DRG Neurons It was previously demonstrated that that MA reduces PIEZO2 currents in mouse and rat dorsal root ganglia neurons, a human Merkel cell carcinoma cell line (MCC13), and human induced pluripotent stem cells (iPSCs)-derived touch receptor neurons. Importantly, several Piezo2-related human diseases originate from an increase in PIEZO2 function due to a decrease in currents inactivation. FIG. 21 demonstrates that combining MA and EPA impaired PIEZO2 function affecting two of its inherent features: 1) reducing currents while increasing the displacement threshold and 2) enhancing its inactivation. As proposed before, individual or combined fatty acids will be used to develop different ointment/lotion formulations to counteract mechanical allodynia.

Example 11: Exemplary Topical Formulations

Tables 1 and 2 provide exemplary MA formulations. The process is provided in Table 3:

TABLE 1

First exemplary formulation

| Date of Preparation Ingredient Purpose | Monday, Jan. 25, 2021 Ingredient Name | Active Theoretical % (w/w), ±5% | Actual % (w/w), ±5% |
|---|---|---|---|
| API-1 | Heptadecanoic acid (MA) | 0.5 | 0.52% |
| API-2 | Eicosapentaenoic acid (EPA) | 0.5 | 0.52% |
| Main Solvent | Sesame Oil | 25 | 26.37% |
| Co-Solvent | Paraffin Oil | 25 | 25.02% |
| Viscosity Agent | Castor Oil | QS to 100 | 47.57% |
| | Total | 100.00 | |

TABLE 2

Second exemplary fomulaiton

| Date of Preparation Ingredient Purpose | Monday, Jan. 25, 2021 Ingredient Name | Placebo Theoretical % (w/w), ±5% | Actual % (w/w), ±5% |
|---|---|---|---|
| API-1 | Heptadecanoic acid (MA) | 0 | 0.00% |
| API-2 | Eicosapentaenoic acid (EPA) | 0 | 0.00% |
| Main Solvent | Sesame Oil | 25 | 25.20% |
| Co-Solvent | Paraffin Oil | 25 | 24.72% |
| Viscosity Agent | Castor Oil | QS to 100 | 50.08% |
| | Total | 100.00 | |

TABLE 3

| Processing |
|---|
| 1. Set up a water bath with minimum 60° C. |
| 2. Weigh APIs and heat in the water bath. Ensure API melted before next step. |
| 3. Weigh and add Sesame Oil. Vortex to form a uniform mixture. Keep heating. |
| 4. Weigh and add Paraffin Oil. Vortex to form a uniform mixture. Keep heating. |
| 5. Weigh and add Castor Oil. Vortex to form a uniform mixture. Keep heating. |
| 6. Stop heating after 5 minutes. Let the mixture cool down in room temperature. |
| 7. Store in room temperature (25° C.) until usage |

DISCUSSION

Mechanosensory ion channels are essential as they allow us to detect innocuous, pleasurable, alarming or painful stimuli. PIEZO2 has emerged as the principle molecular detector for specific aspects of gentle touch (vibration sensing and tactile discrimination) via its expression in specialized epithelial cells (Merkel cells) and peripheral sensory neurons. Importantly, PIEZO2 is also essential for the experience of touch-evoked pain after injury or under chronic inflammation, a common condition known as tactile allodynia that remains difficult to treat. Specifically, proalgesic agents (such as bradykinin) produced in response to tissue injury potentiate PIEZO2 response. In the ideal scenario, new treatment approaches will be developed to specifically counteract this type of pain without impairing normal touch function. In the current study, we demonstrated that application of margaric acid, a natural product found in several sources of food such as dairy and mutton fat, rye, and fish, effectively reduces Piezo2 function.

Previously, we showed that MA can be efficiently enriched in various cell types and as a consequence alter the activation profile of PIEZO1 channels by increasing the plasma membrane structural order and rigidity. Interestingly, previous work suggests that PIEZO1 and PIEZO2 have distinct gating mechanisms. While both are likely to be sensitive to membrane tension, only PIEZO2 function depends on an intact cytoskeleton. Whether PIEZO2 activation also relies on the mechanical properties of the plasma membrane is less understood. Our data indicate that PIEZO2 activation is impaired by membrane rigidity and that the beam domain and the cytoskeleton counteract the effect of the membrane tension. This highlights that the beam is a key region for tuning MA-mediated channel inhibition. Putting our data in larger context, we favor the idea that PIEZO2 works as part of a force-bearing center. In this model, PIEZO2 function is tightly controlled by a platform comprising the plasma membrane (fatty acid tails and polar head groups), stomatin-like proteins, cytoskeleton elements (actin and microtubules), and extracellular tethers (e.g., focal adhesions).

How selective is MA for mechanosensing? Our data show that MA reduces the ability of DRG neurons to fire action potentials upon mechanical stimulation without affecting the membrane potential, current-elicited action potentials, and voltage-activated inward $Na_+$ and outward $K_+$ currents. Likewise, MA reduces PIEZO2 mechanical activation while leaving other ionic currents intact in iPSC-derived neurons. Moreover, sub-cutaneous injections of MA did not affect the ability of mice to sense thermal stimuli. These results strongly support that this dietary fatty acid specifically reduces neuronal mechanical excitability. As such, MA seems to have many properties preferable over other identified mechanoreceptor antagonists such as the tarantula peptide GsMTx-4 that failed to inhibit mechano-currents from DRG neurons. In addition, it has been shown that the conopeptide analog NMB-1 only inhibits the intermediate and slowly inactivating mechanosensitive currents, but not the rapid ones. Importantly, unlike peptide toxins, MA is able to inhibit all mechanosensitive currents of mouse and rat DRG neurons and of human iPSCs derived neurons.

With the recent discovery that PIEZO2 is required for tactile allodynia in mice and humans, this channel has emerged as a promising target to treat inflammatory conditions. Our data shows that MA is able to counteract PIEZO2 potentiation evoked by bradykinin by reducing the mechano-currents to non-inflammatory levels. Hence, MA seems to present a possible approach to decreasing mechanical hypersensitivity after inflammation. Notably, under our behavioral conditions, MA selectively decreases tactile allodynia without noticeable effects on baseline touch sensitivity. Current experimental and clinical studies favor treatments targeting peripheral sensory receptors while avoiding systemic delivery. Thanks to its high hydrophobicity, MA is a candidate for the development of topical lotion and/or cream treatments to help attenuate inflammatory pain.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

What is claimed is:

1. A method of treating pain, comprising
administering to a subject in need of treatment for pain a pharmaceutical composition comprising a therapeutically effective amount of margaric acid.

2. The method of claim 1, wherein the pharmaceutical composition is a topical, transdermal, oral, transmucosal, or parenteral composition.

3. The method of claim 1, wherein the pharmaceutical composition is a topical or transdermal composition for delivery through the skin.

4. The method of claim 3, wherein the topical or transdermal composition is a liquid, gel, lotion, cream ointment, paste, or a topical patch.

5. The method of claim 3, wherein the topical or transdermal dosage of margaric acid is 0.1 to 20 mg/kg of margaric acid.

6. The method of claim 3, wherein the topical formulation is a lotion comprising margaric acid in an amount of 0.2-10 wt % of the total weight of the formulation.

7. The method of claim 1, wherein the pain is chronic or acute.

8. The method of claim 1, wherein the pain is mild or severe.

9. The method of claim 1, wherein the pain is inflammatory pain, pain due to nerve injury, neuropathic pain, chronic pain, intractable cancer pain, complex regional pain syndrome, surgical or post-surgical pain, dental pain, pain resulting from dermal injury, lower back pain, headaches, migraine, or hyperalgesia.

10. The method of claim 9, wherein the pain is neuropathic pain.

11. The method of claim 10, wherein the neuropathic pain is allodynia.

12. The method of claim 11, wherein the allodynia is tactile allodynia, mechanical allodynia or thermal allodynia.

13. The method of claim 12, wherein the subject is suffering from fibromyalgia, chronic inflammation, migraines, trigeminal neuralgia, postherpetic neuralgia, peripheral neuropathy, diabetic neuropathic pain, chronic fatigue syndrome, or complex regional pain syndrome.

14. The method of claim 9, wherein the pain is inflammatory pain.

15. The method of claim 14, wherein the inflammatory pain inflammatory joint pain, inflammatory musculoskeletal pain, pain due to injury, arthritis pain, and complex regional pain syndrome.

16. The method of claim 1, wherein the pharmaceutical composition further comprises eicosapentaenoic acid.

17. The method of claim 1, wherein the pharmaceutical composition is a topical composition for instillation into the eye.

18. The method of claim 2, wherein the topical pharmaceutical composition comprises margaric acid at 0.01% to 10% by weight, 0.2-10% by weight, or 0.5-25% by weight.

19. The method of claim 2, wherein the topical pharmaceutical composition is administered in the form of drops.

20. The method of claim 2, wherein the topical pharmaceutical composition is administered intraocularly.

21. A method of treating pain, comprising instillation into the eye of a subject in need of treatment for pain a topical pharmaceutical composition comprising a therapeutically effective amount of margaric acid.

22. The method of claim 21, wherein the topical pharmaceutical composition comprises margaric acid at 0.01% to 10% by weight, 0.2-10% by weight, or 0.5-25% by weight.

23. The method of claim 21, wherein the topical pharmaceutical composition is administered in the form of drops.

24. The method of claim 1, wherein the pharmaceutical composition is a topical composition.

* * * * *